US010471025B2

(12) United States Patent
Afonso et al.

(10) Patent No.: US 10,471,025 B2
(45) Date of Patent: Nov. 12, 2019

(54) COMPOSITIONS FOR USE IN TREATING PARKINSON'S DISEASE AND RELATED DISORDERS

(71) Applicants: Technophage, Investigação E Desenvolvimento Em Biotecnologia, SA, Lisbon (PT); Lusomedicamenta, S.A., Barcarena (PT); Laboratorio Medinfar-Produtos Farmacêuticos, S.A., Algés (PT)

(72) Inventors: Nuno Afonso, Lisbon (PT); Sara Sousa, Lisbon (PT); Rita Vaz, Torres Vedras (PT); Diana Chapela, Tomar (PT); Sofia Côrte-Real, Cruz Quebrada (PT)

(73) Assignees: TECHNOPHAGE, INVESTIGACAO E DESENVOLVIMENTO EM BIOTECNOLOGIA, SA; LUSOMEDICAMENTA, SA; LABORATORIO MEDINFAR PRODUTOS FARMACEUTICOS, SA

( * ) Notice: Subject to any disclaimer, the term of this patent is extended or adjusted under 35 U.S.C. 154(b) by 0 days.

(21) Appl. No.: 15/568,655

(22) PCT Filed: May 25, 2016

(86) PCT No.: PCT/PT2016/050010
§ 371 (c)(1),
(2) Date: Oct. 23, 2017

(87) PCT Pub. No.: WO2016/190766
PCT Pub. Date: Dec. 1, 2016

(65) Prior Publication Data
US 2018/0147160 A1    May 31, 2018

Related U.S. Application Data

(60) Provisional application No. 62/166,531, filed on May 26, 2015.

(51) Int. Cl.
| | | |
|---|---|---|
| *A61K 31/12* | (2006.01) | |
| *A61K 31/137* | (2006.01) | |
| *A61K 31/138* | (2006.01) | |
| *A61K 31/198* | (2006.01) | |

(Continued)

(52) U.S. Cl.
CPC ............ *A61K 31/137* (2013.01); *A61K 31/12* (2013.01); *A61K 31/138* (2013.01); *A61K 31/198* (2013.01); *A61K 31/513* (2013.01); *A61P 25/16* (2018.01)

(58) Field of Classification Search
CPC .. A61K 31/137; A61K 31/513; A61K 31/198; A61K 31/138; A61K 31/12; A61P 25/16
See application file for complete search history.

(56) References Cited

U.S. PATENT DOCUMENTS

2014/0037729 A1* 2/2014 Hopp ................... A61K 9/0034
424/468

FOREIGN PATENT DOCUMENTS

| WO | WO 2009/067703 | 5/2009 |
| WO | WO 2012/089738 | 7/2012 |
| WO | WO 2012/136351 | 10/2012 |

OTHER PUBLICATIONS

Encarnacion et al., "Levodopa-Induced Dyskinesias in Parkinson's Disease: Etiology, Impact on Quality of Life, and Treatments," European Neurology, vol. 60, No. 2, pp. 57-66, 2008.

(Continued)

*Primary Examiner* — Sudhakar Katakam
(74) *Attorney, Agent, or Firm* — King & Spalding LLP; Peg Brivanlou; Nicole Fortune

(57) ABSTRACT

The present invention relates to methods of treating and managing Parkinson's disease and related disorders. The methods especially find use in managing motor symptoms, including gait problems, particularly during advanced stages when effectiveness of standard medications wear off or side effects become problematic, as seen in Parkinson's disease, other disorders treated with dopaminergic agents, and other conditions associated with motor problems, such as aging or stroke. The treatment also may include disease-modifying effects, neuroprotection of, or neurorescue effects on neuronal cells in patients with Parkinson's disease and other neurodegenerative disorders. In particular, the invention relates to method of administering pharmaceutical compositions comprising effective amounts of tapentadol or a pharmaceutically acceptable salt or derivative thereof or, in other embodiments, stavudine or nabumetone, or a derivative thereof, for treating symptoms associated with Parkinson's disease, either as individual active agents, in combination with each other, or in combination with agents known to treat Parkinson's disease, such as the dopaminergic agent levodopa. The invention also relates to methods of preparing pharmaceutical compositions comprising effective amounts of tapentadol, stavudine, or nabumetone, or a derivative thereof, or further in combination with a dopaminergic agent, or derivative thereof, as well as to methods of using the pharmaceutical compositions in treating Parkinson's disease, related disorders, other conditions treated with dopaminergic agents, and other conditions with gait problems, for example by oral administration of the compositions.

23 Claims, 38 Drawing Sheets

(51) Int. Cl.
    *A61K 31/513*    (2006.01)
    *A61P 25/16*    (2006.01)

(56) References Cited

OTHER PUBLICATIONS

Wade et al., "Tapentadol Hydrochloride: A Centrally Acting Oral Analgesic," Clinical Therapeutics, vol. 31, No. 12, pp. 2804-2818, 2009.
Brodell DW, Stanford NT, Jacobson CE, et al.; *BMJ Open* Dec. 11, 2012; Carbidopa/levodopa dose elevation and safety concerns in Parkinson's patients: a cross-sectional and cohort design.

* cited by examiner

Figures 1A-B

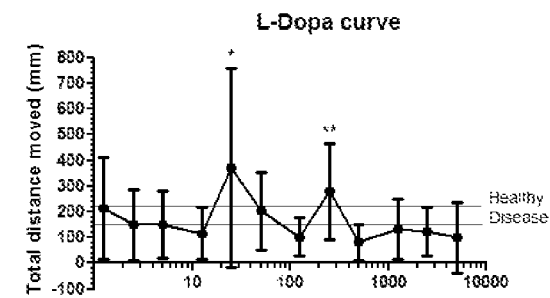
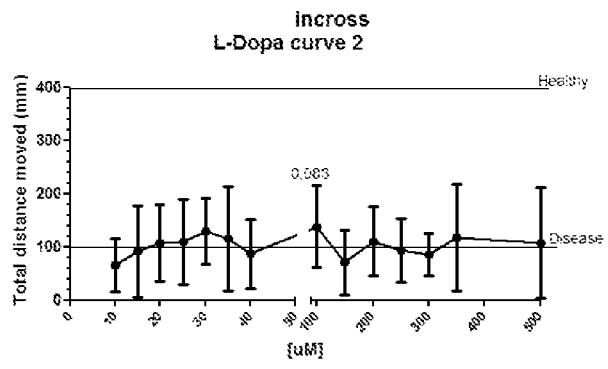
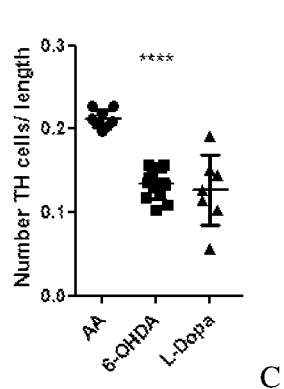
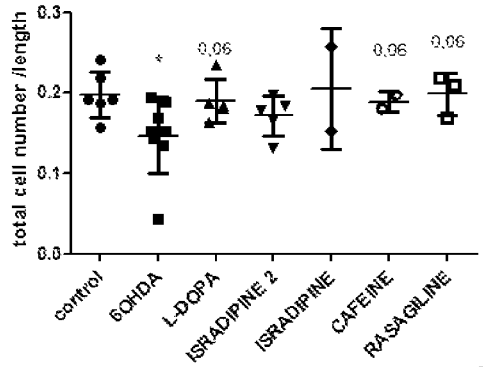
Figures 3A-D

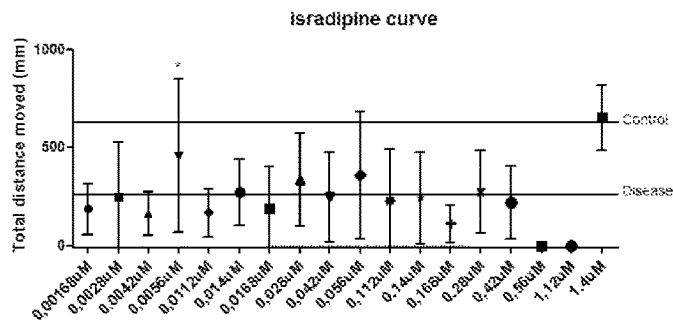
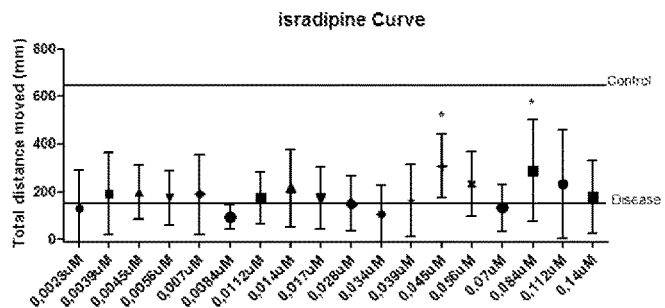
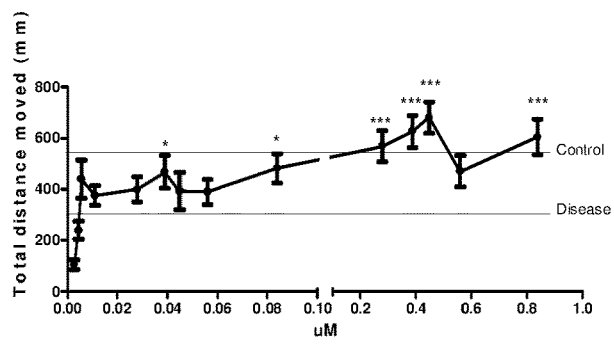
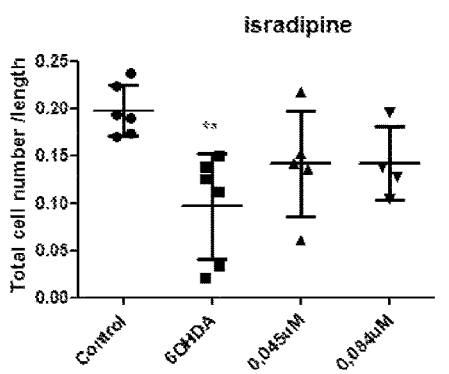
Figures 4A-E

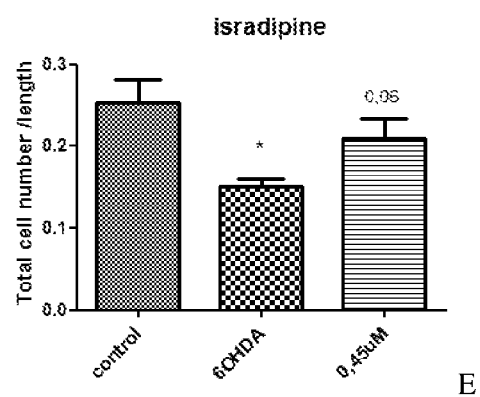
Figures 4A-E (Cont'd)

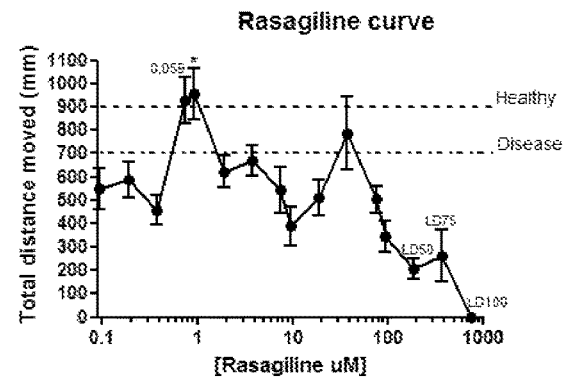
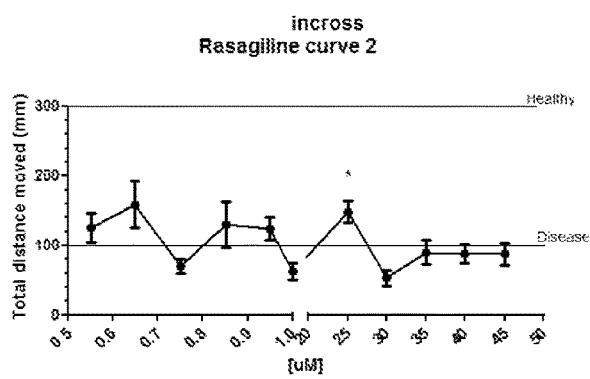
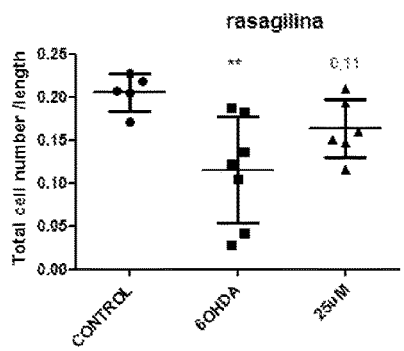
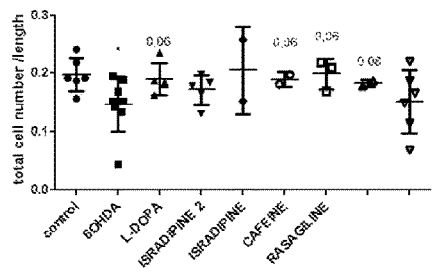
Figures 5A-D

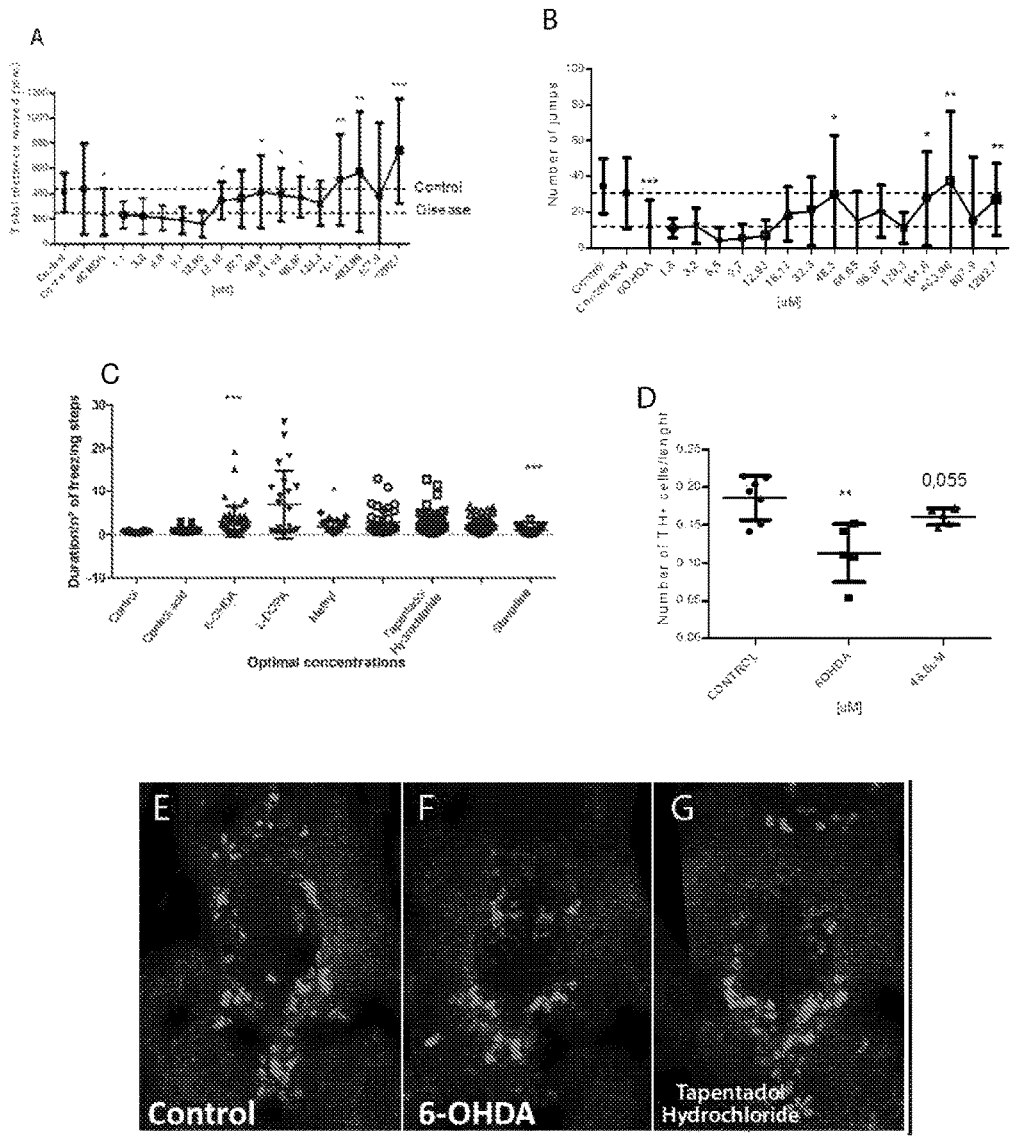
Figures 6A-G

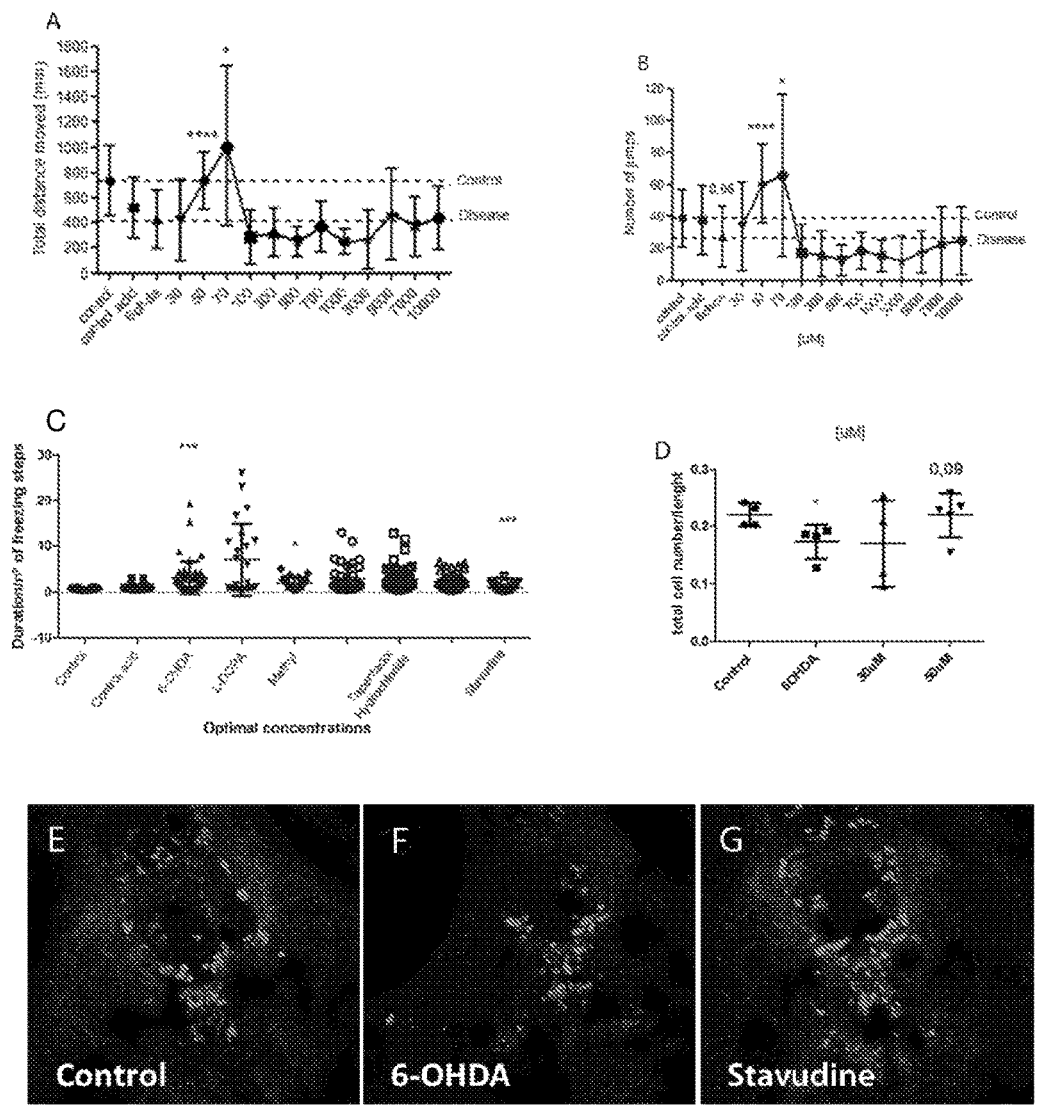
Figures 7A-G

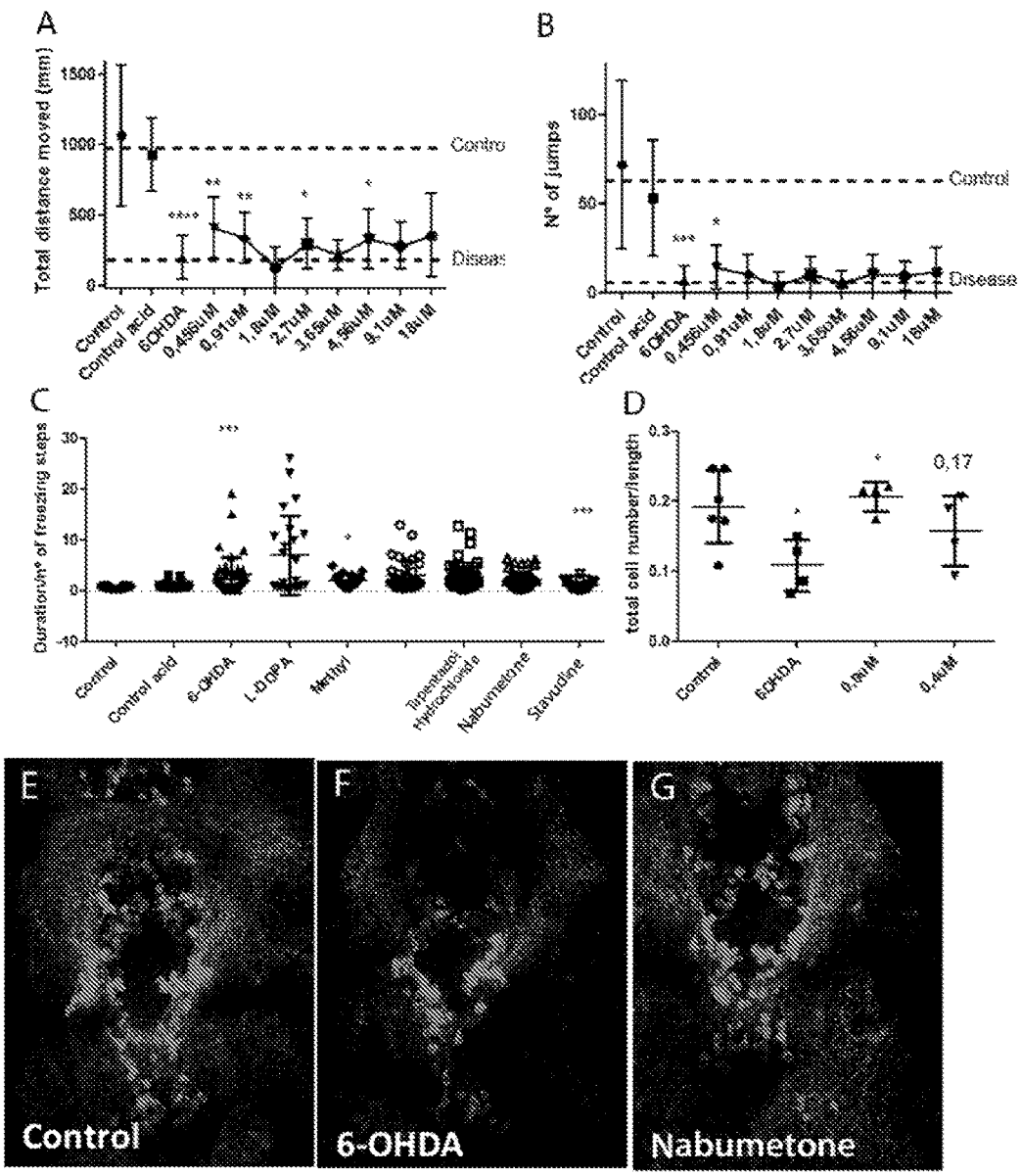
Figures 8A-G

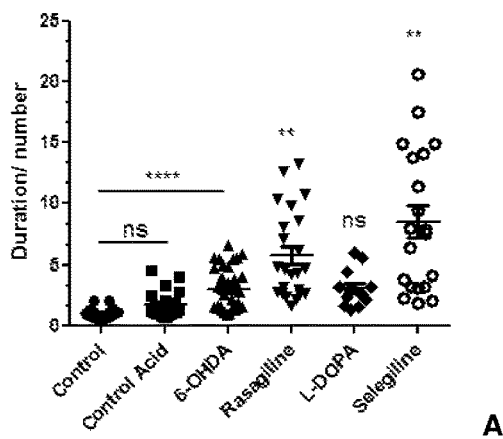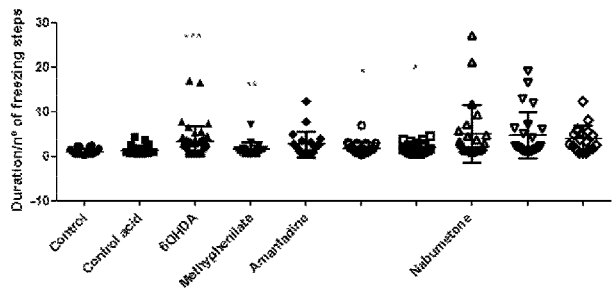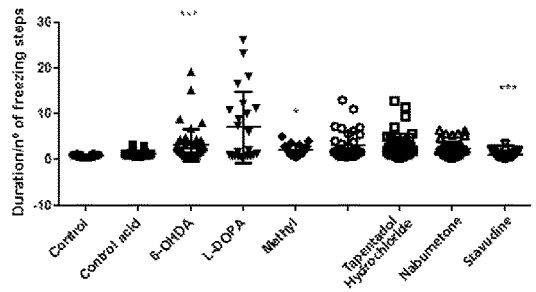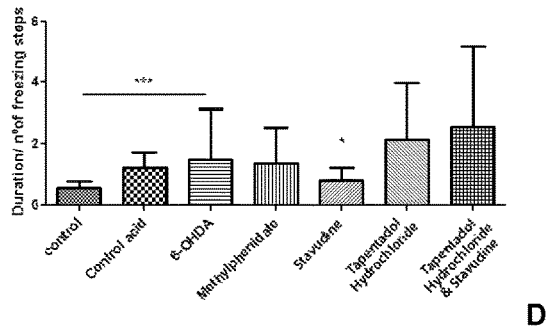
Figures 9A-D

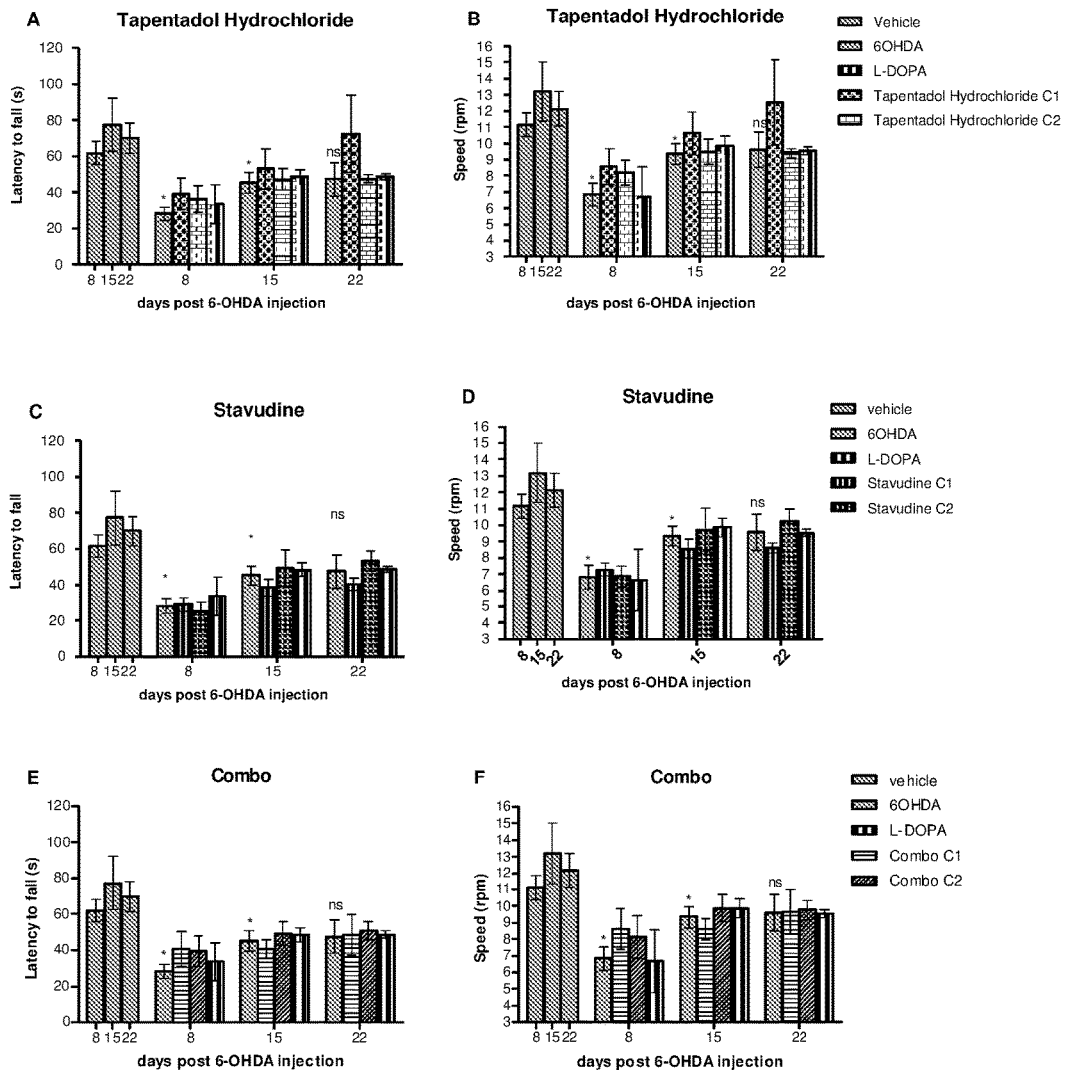
Figures 12A-F

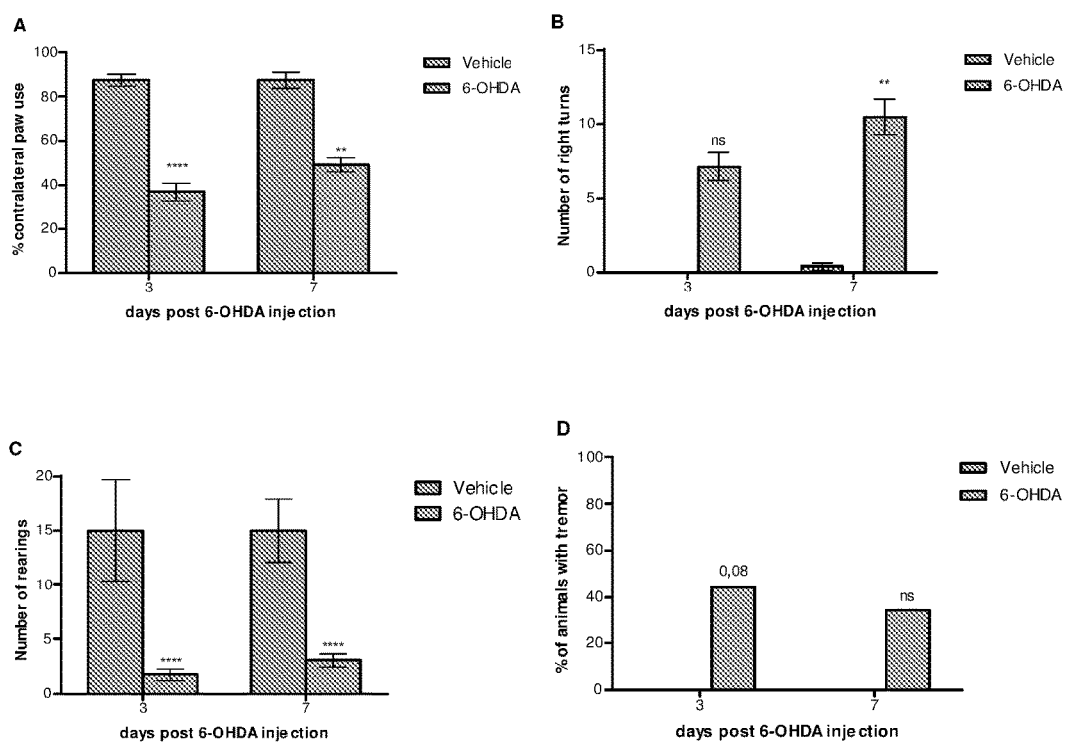
Figures 13A-D

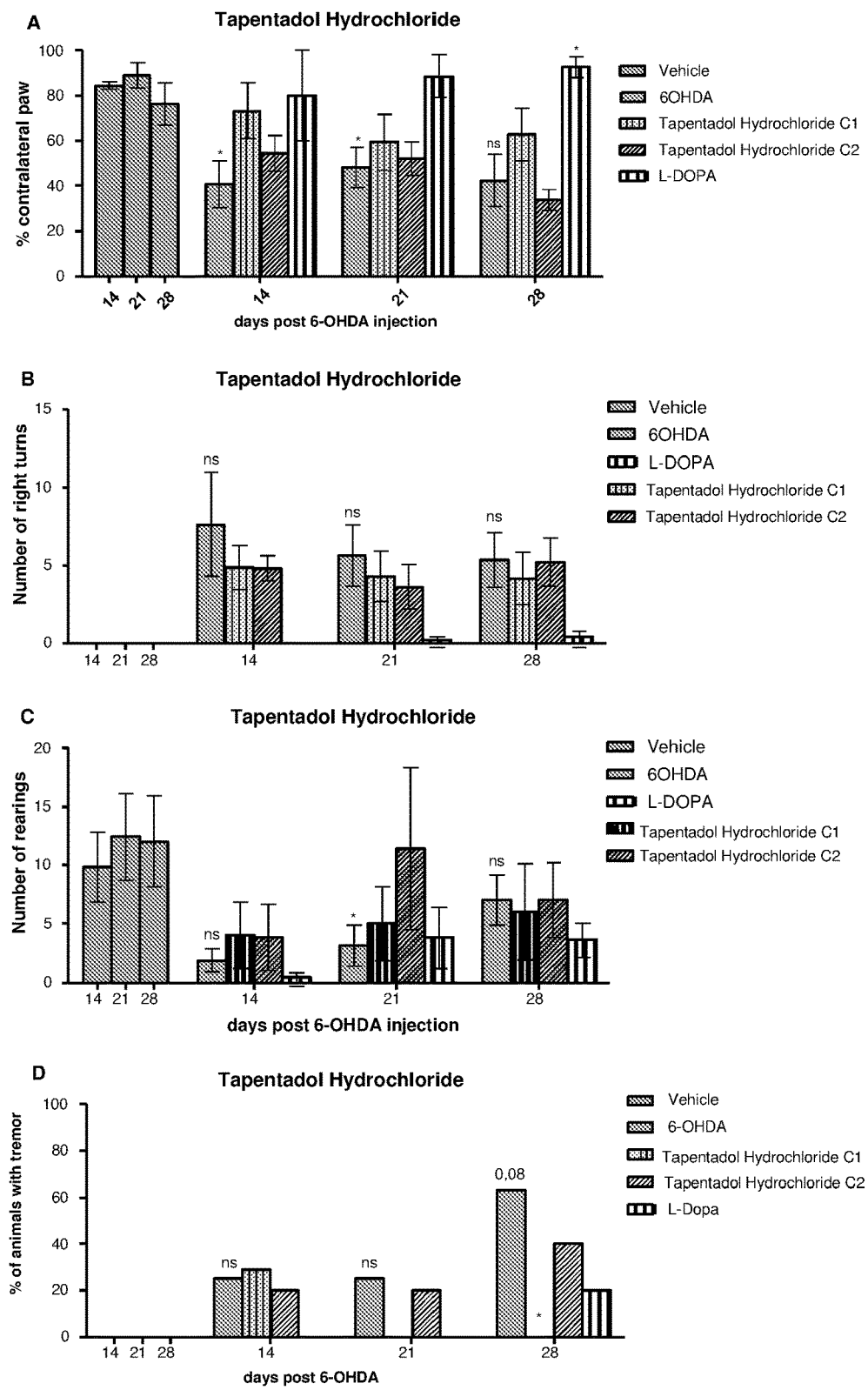
Figures 14A-D

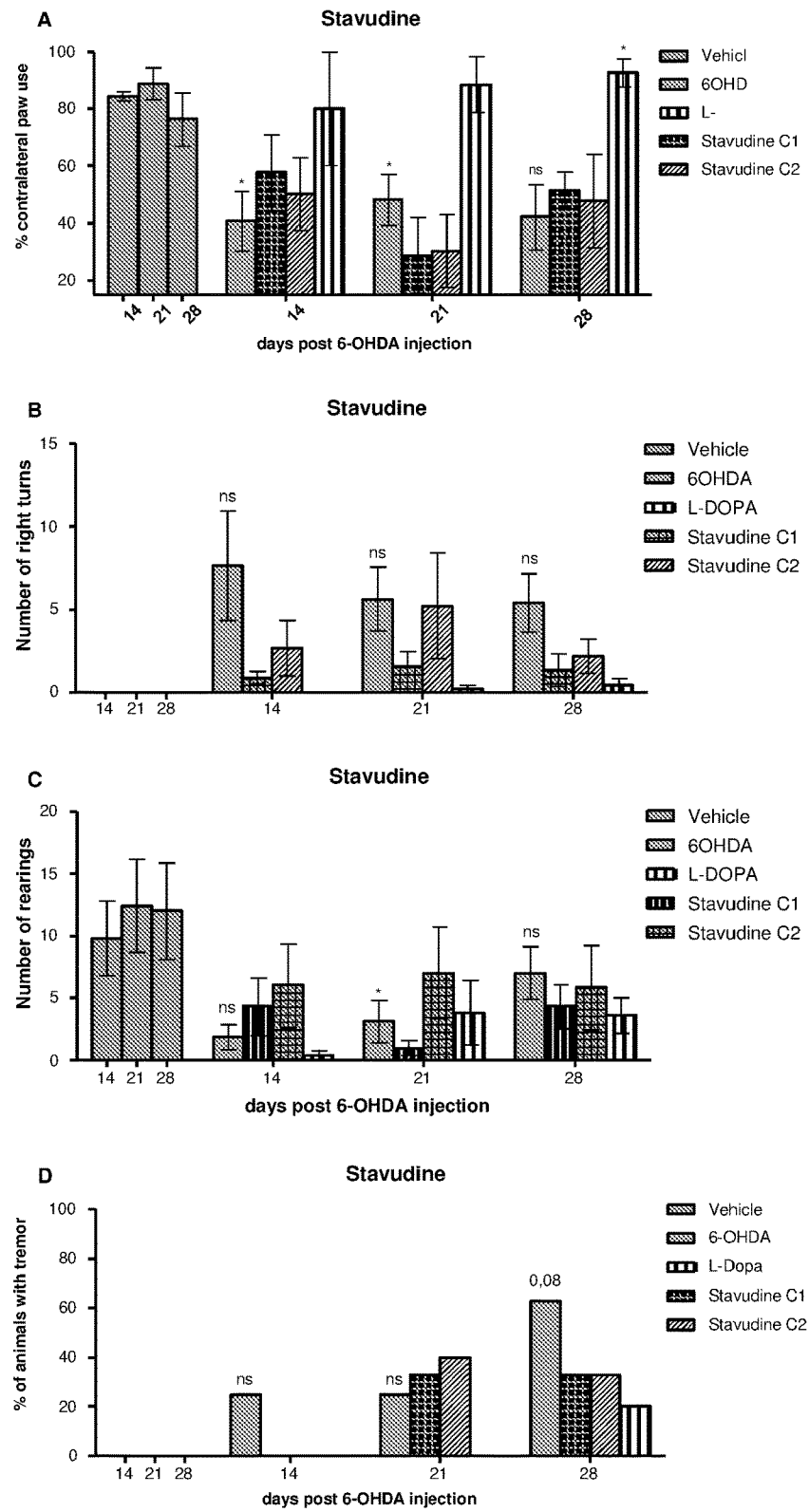
Figures 15A-D

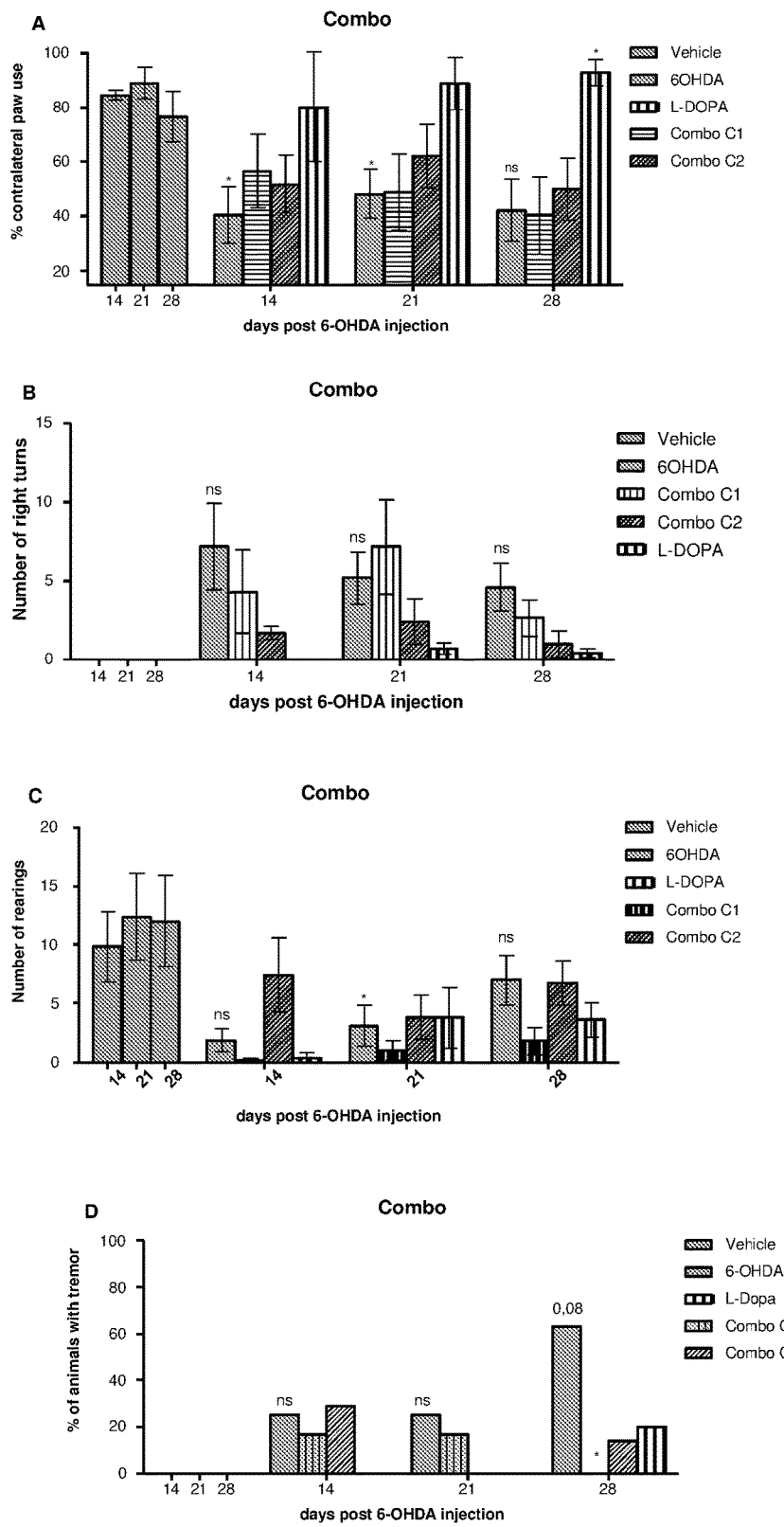
Figures 16A-D

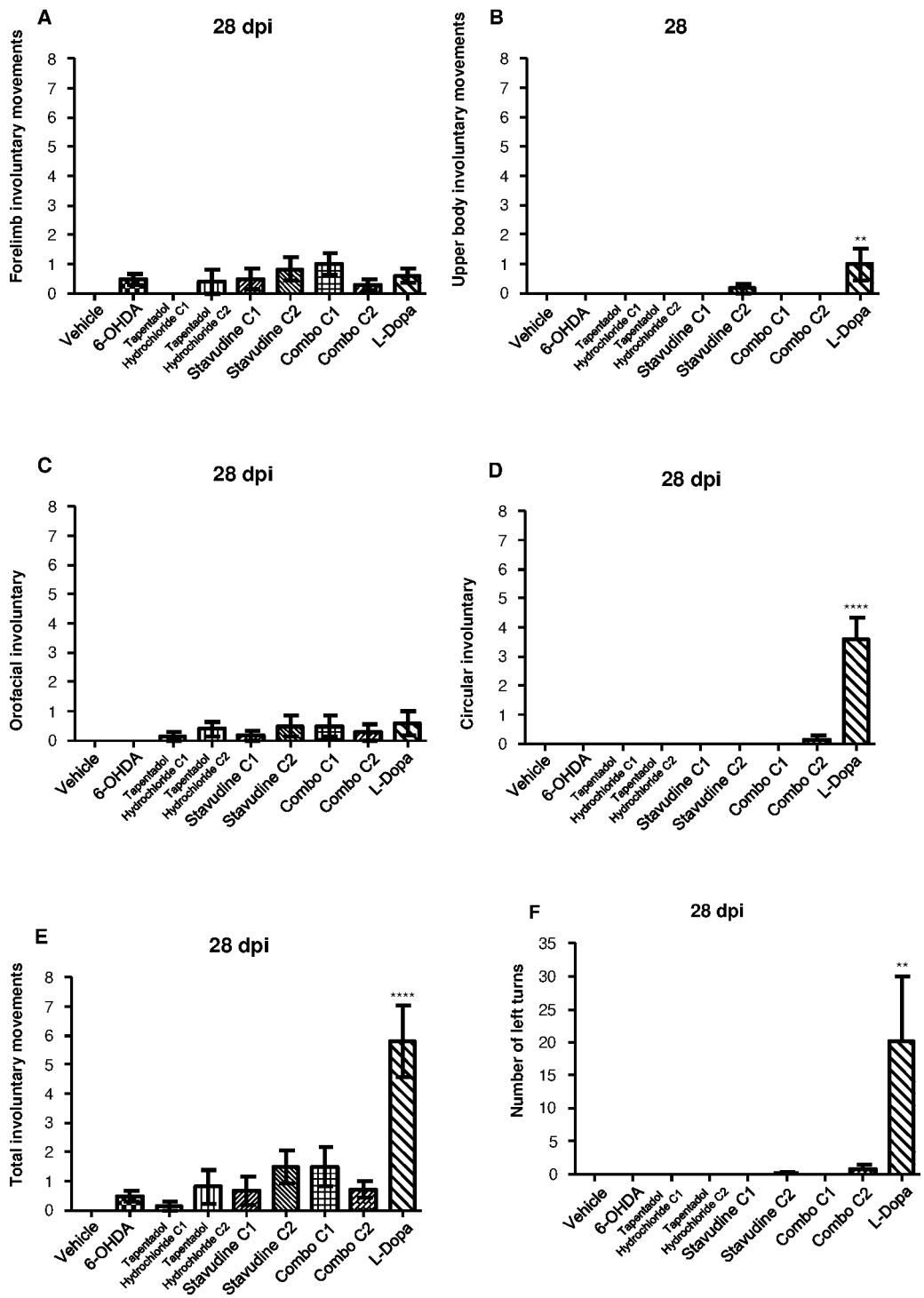
Figures 17A-F

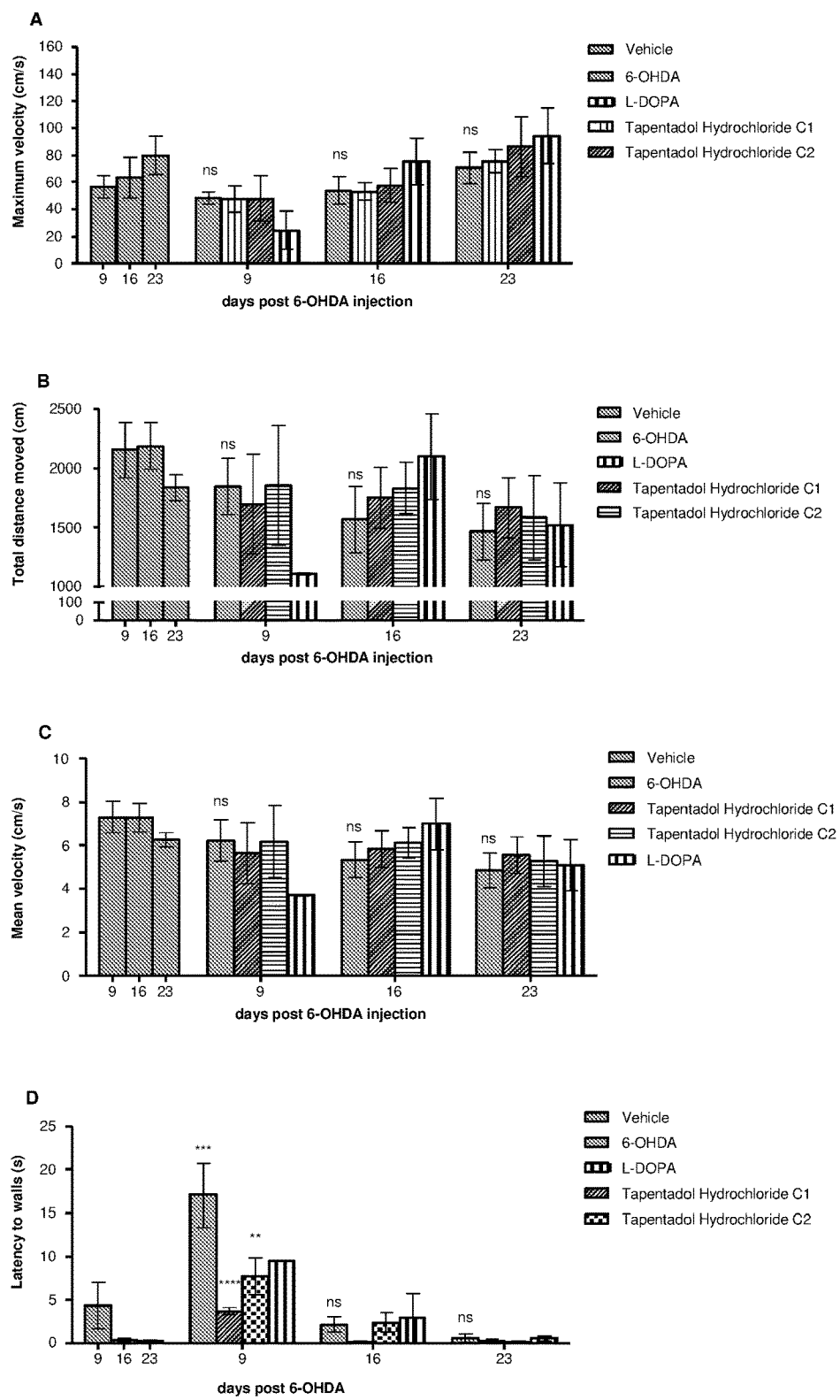
Figures 18A-D

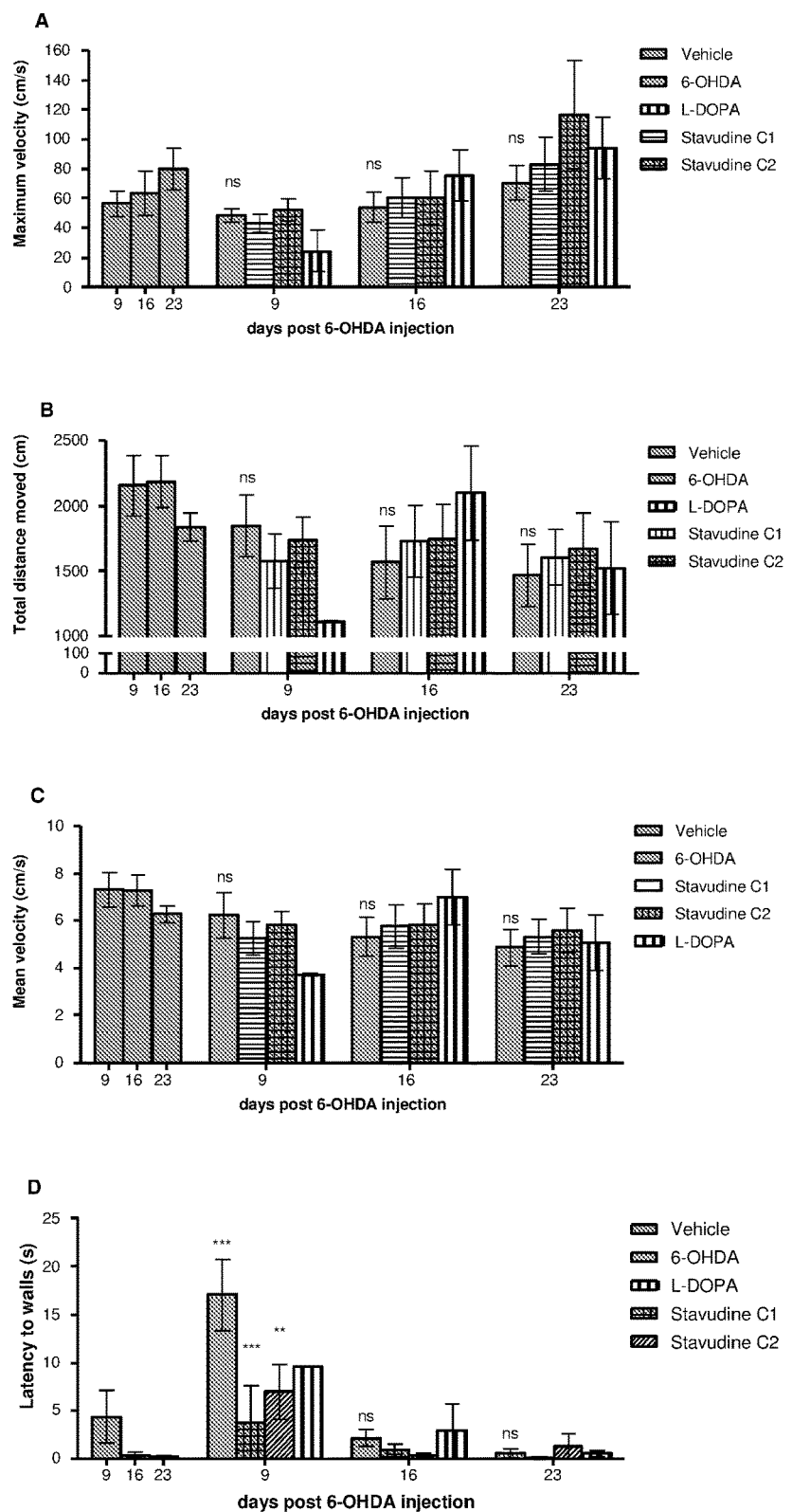
Figures 19A-D

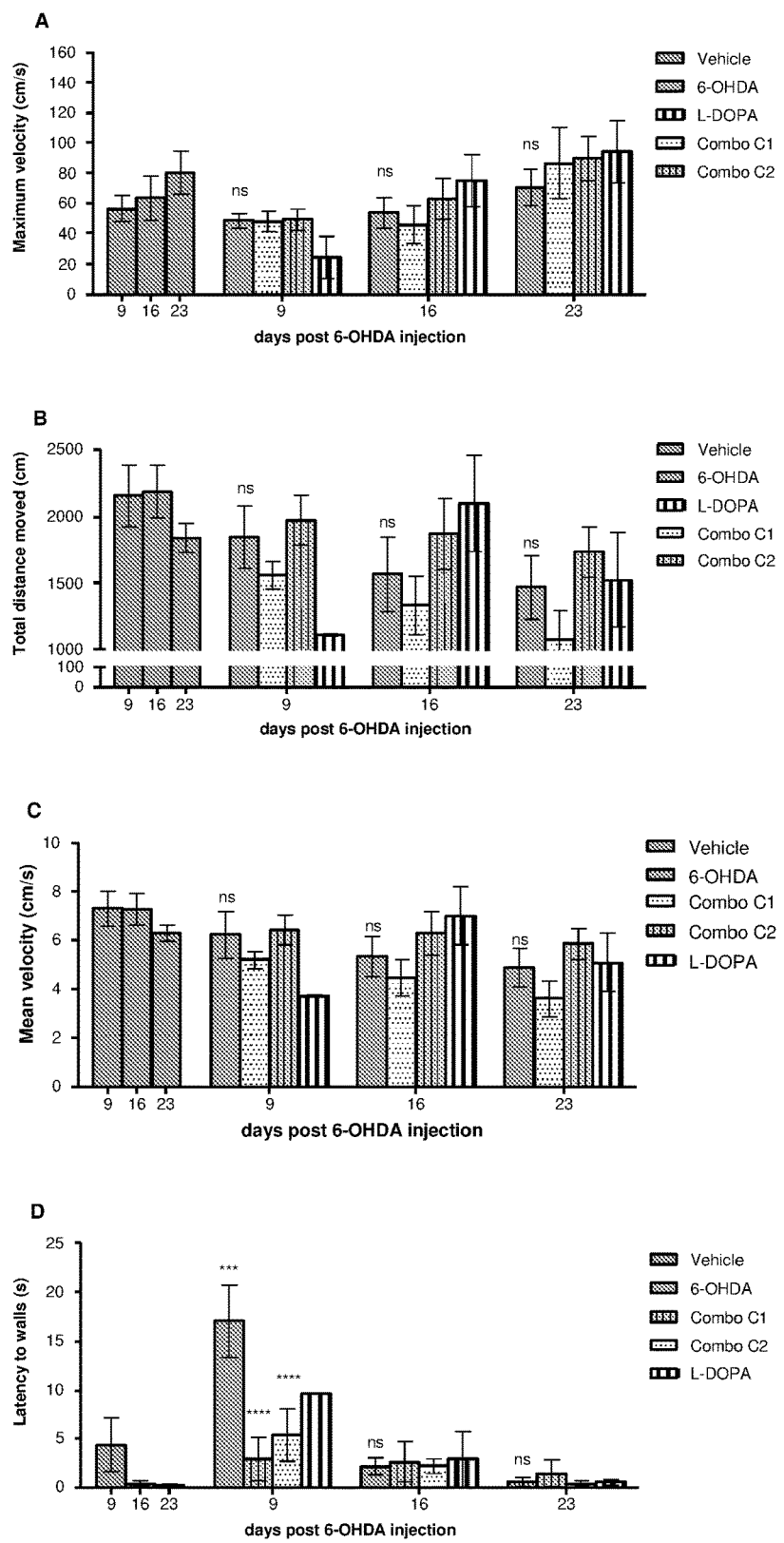
Figures 20A-D

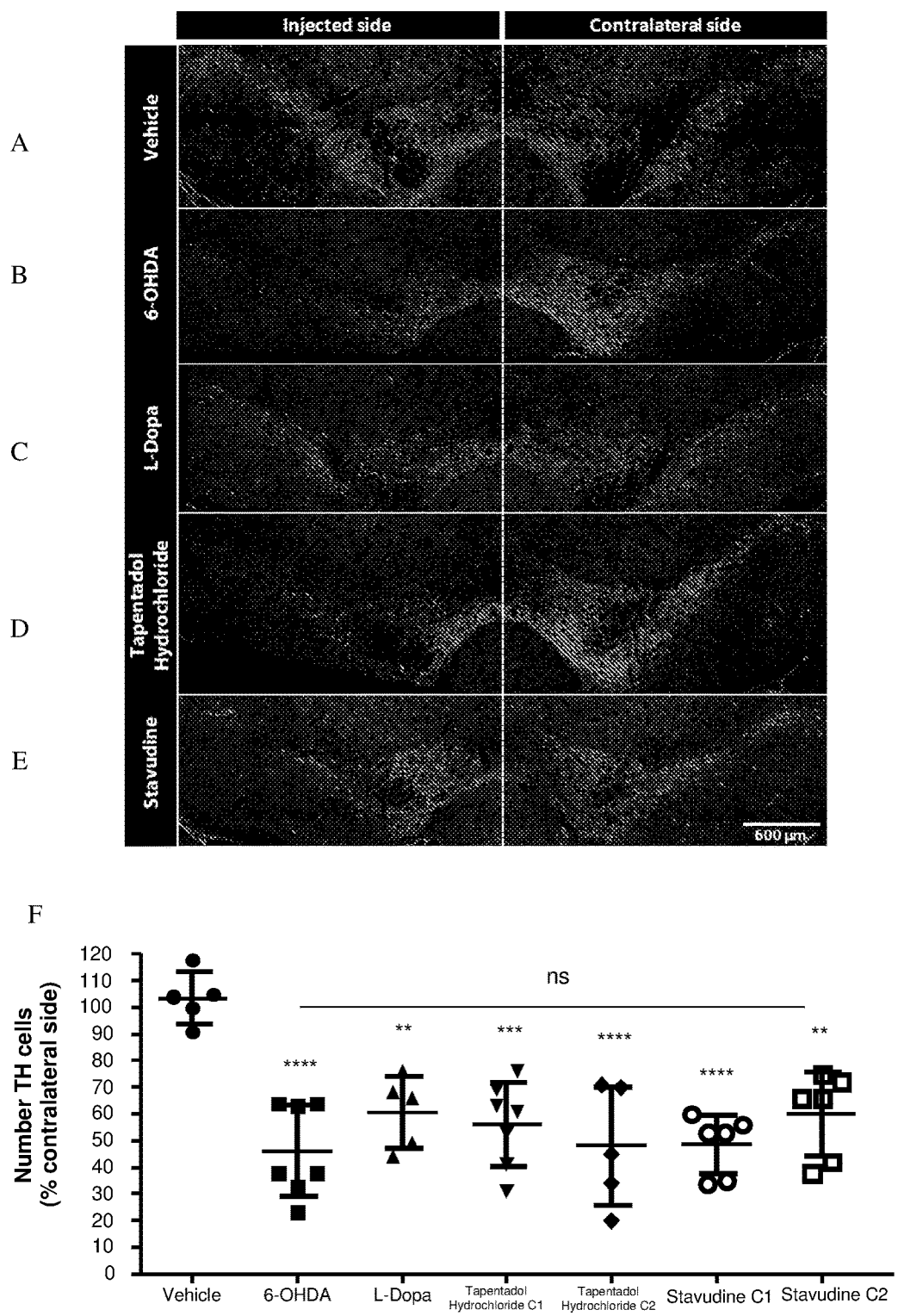
Figures 21A-F

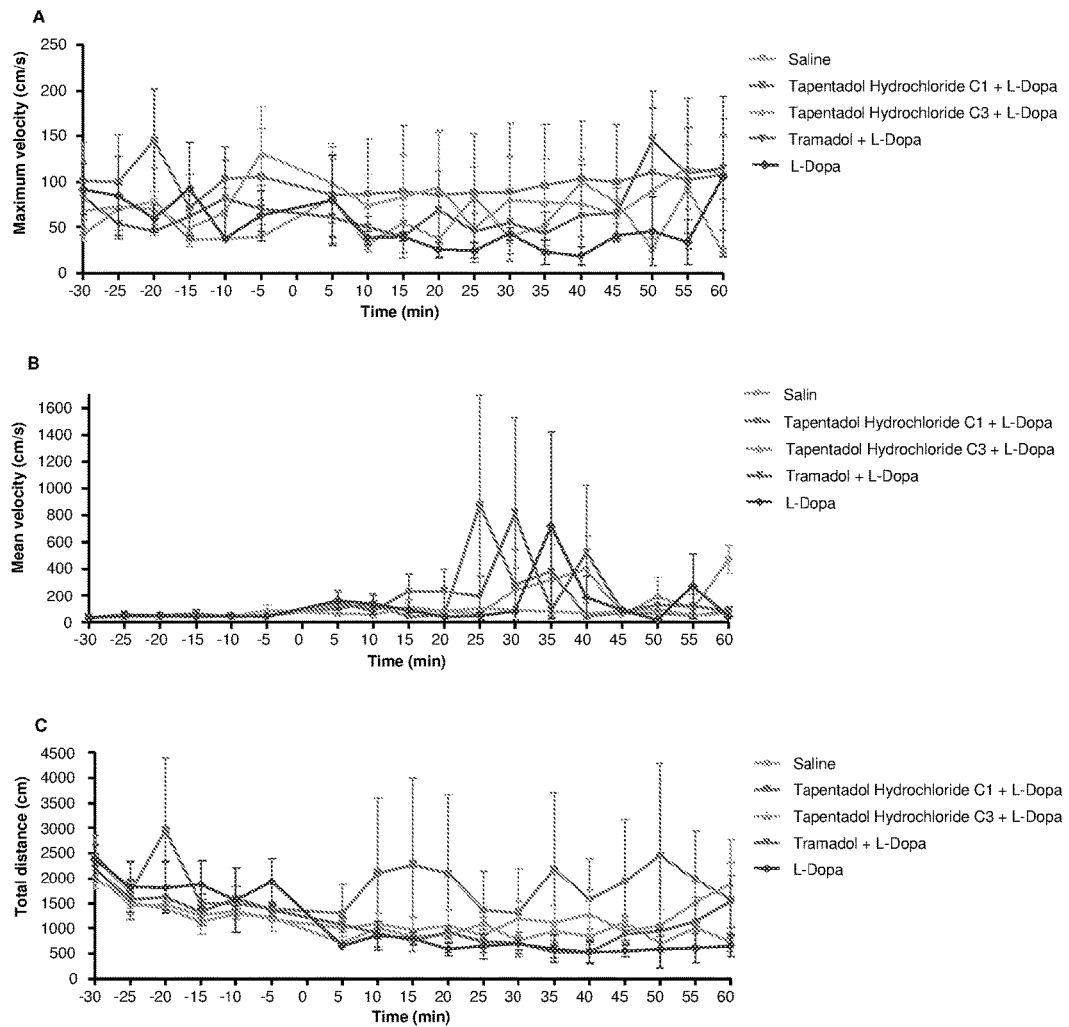
Figures 22A-F

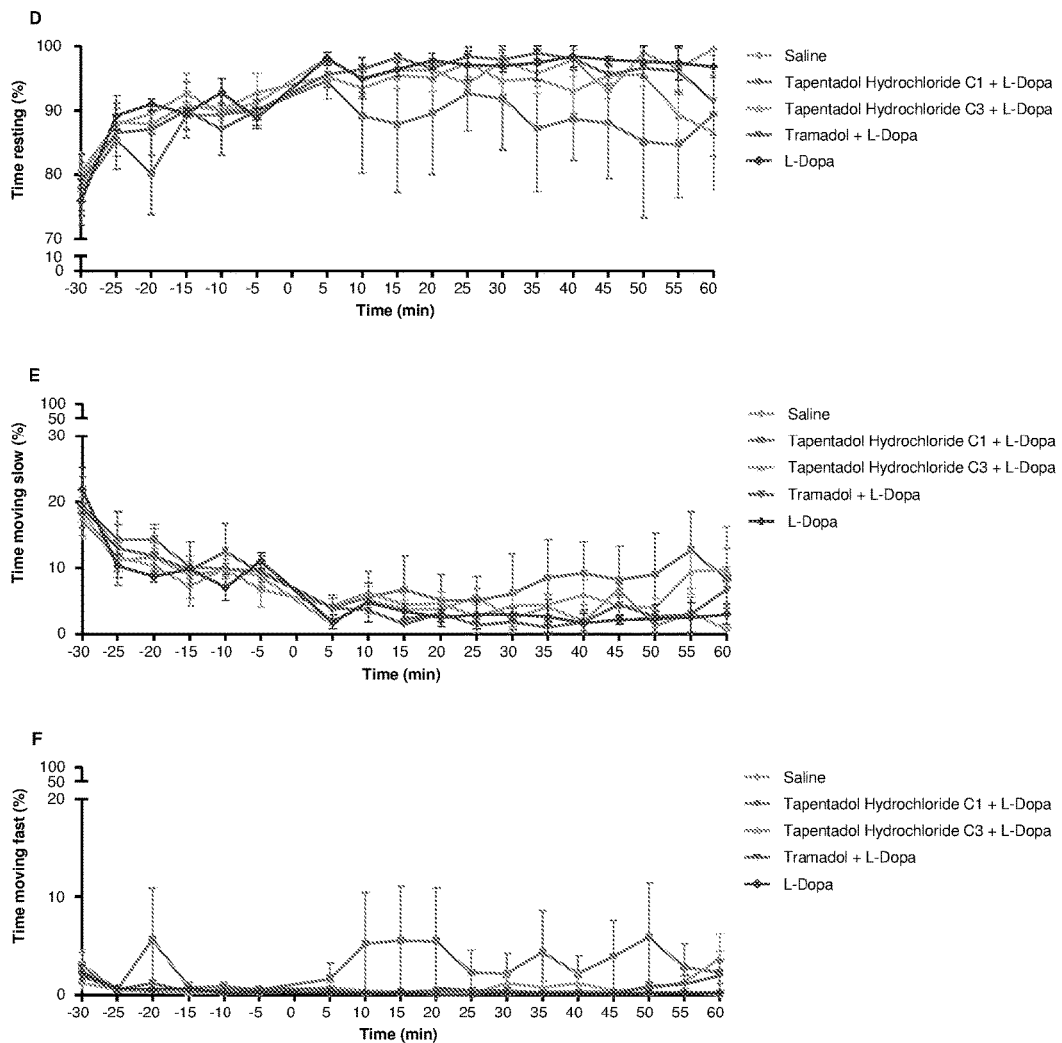
Figures 22A-F (Cont'd)

A
21 dpi – Tapentadol Hydrochloride & L-Dopa
L-Dopa 6 mg/kg
Tapentadol Hydrochloride 3 mg/kg
Tapentadol Hydrochloride 5 mg/kg
B
29 dpi – Tapentadol Hydrochloride & L-Dopa
L-Dopa 18 mg/kg
Tapentadol Hydrochloride 8 mg/kg
Tapentadol Hydrochloride 15 mg/kg
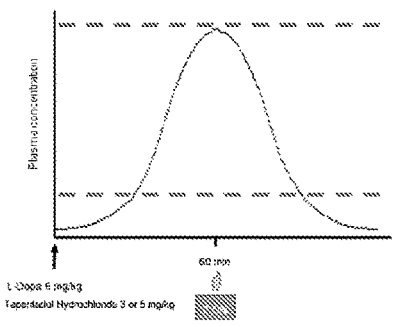
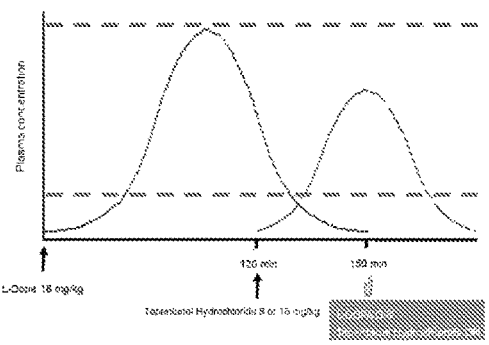
Figure 24A-B

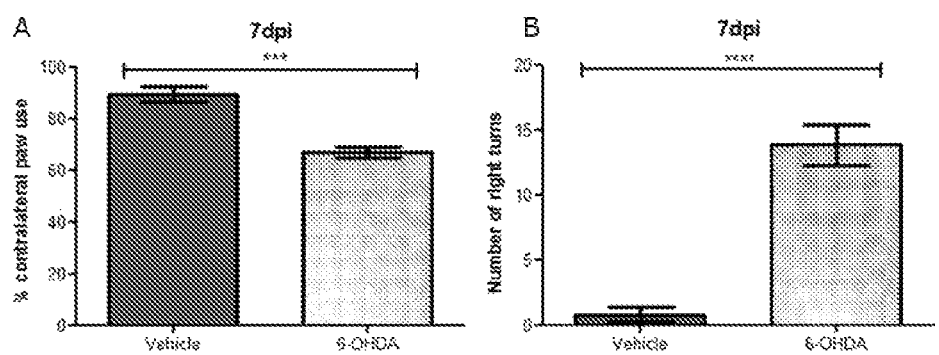
Figures 25A-B

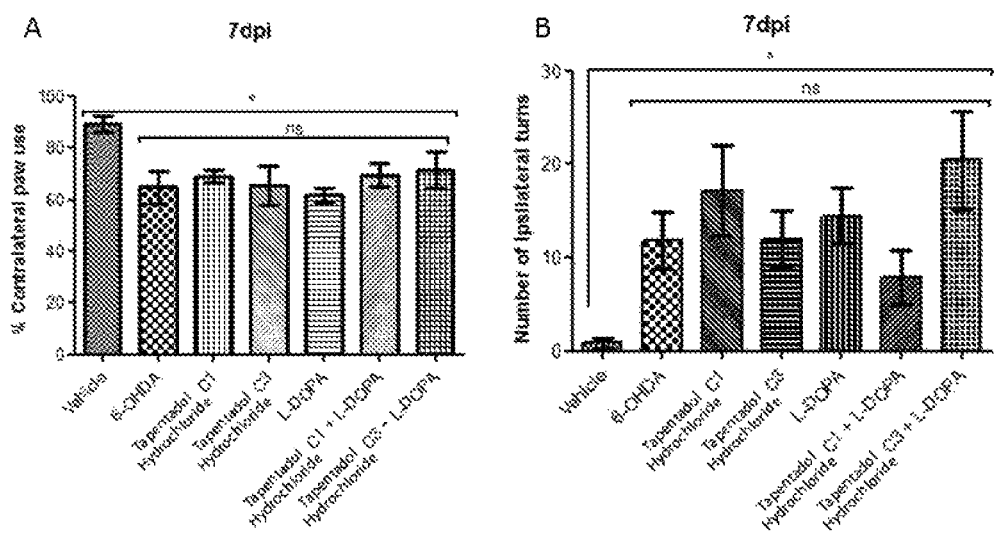
Figures 26A-B

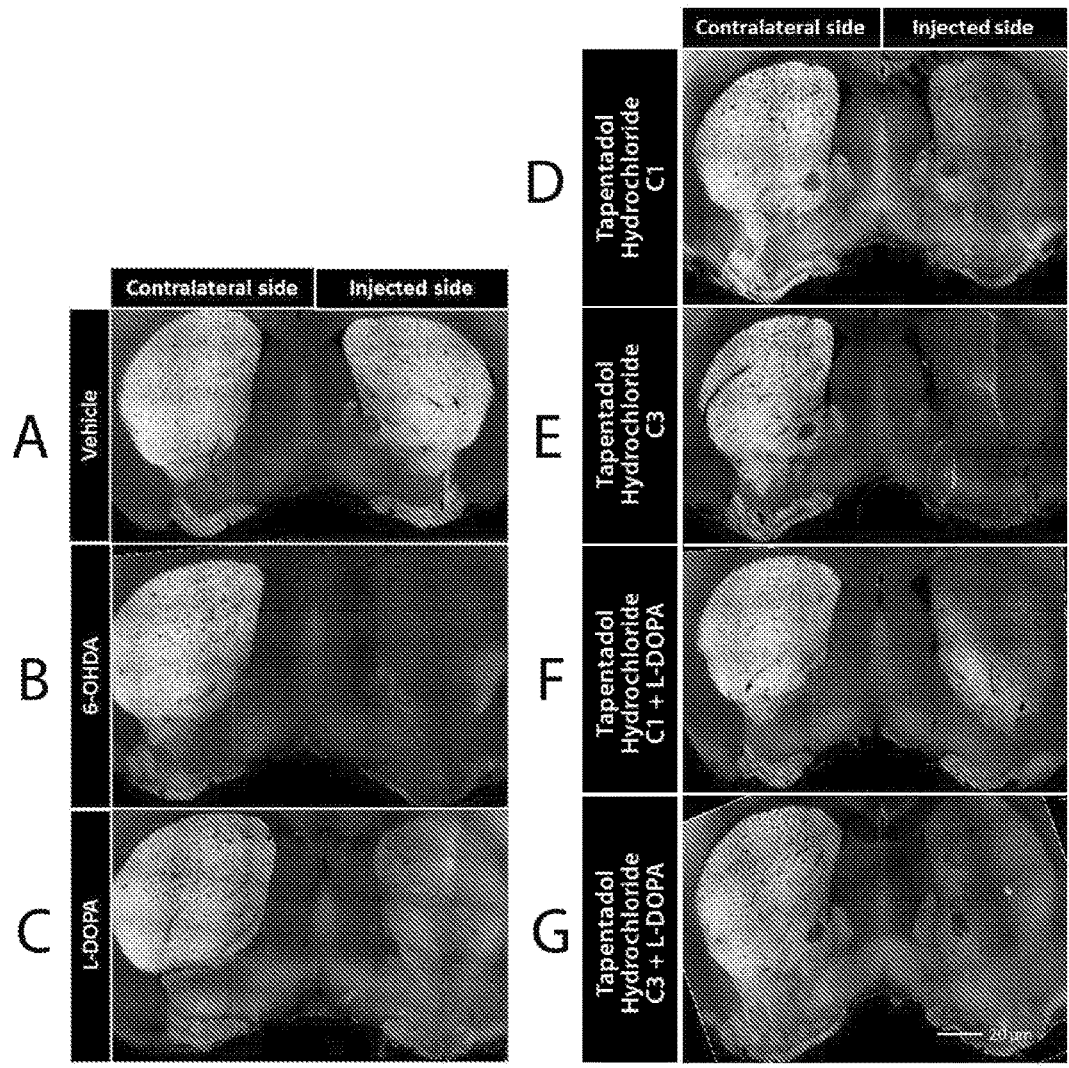
Figures 27A-G

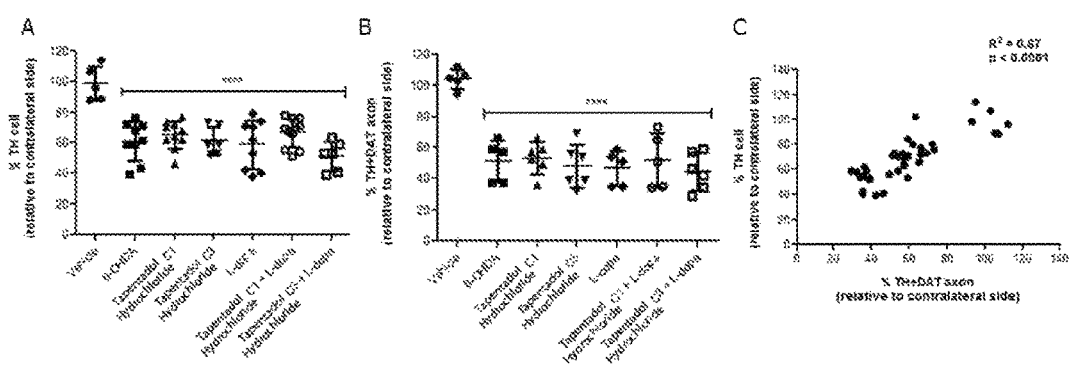
Figures 28A-C

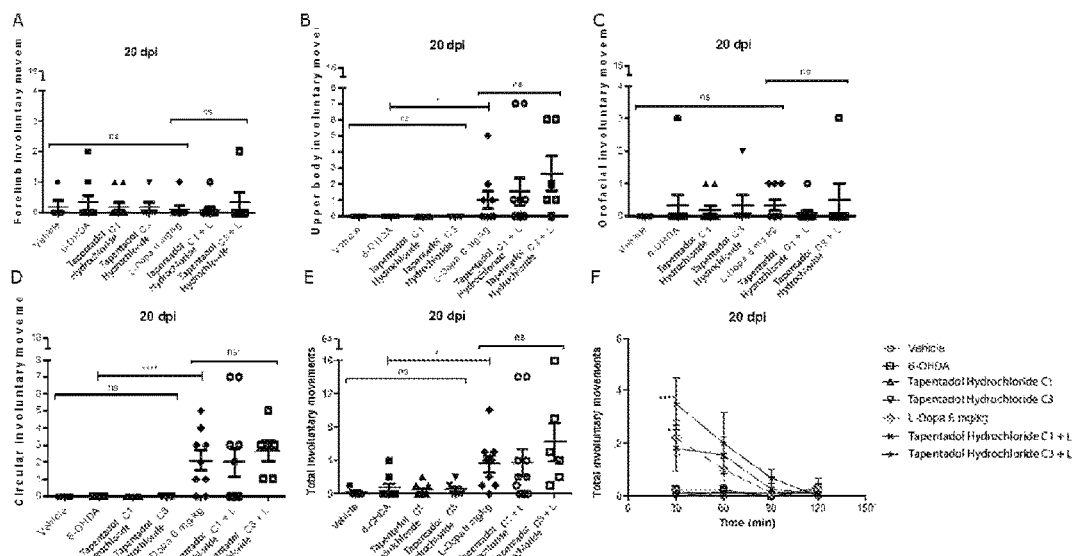
Figures 29A-F

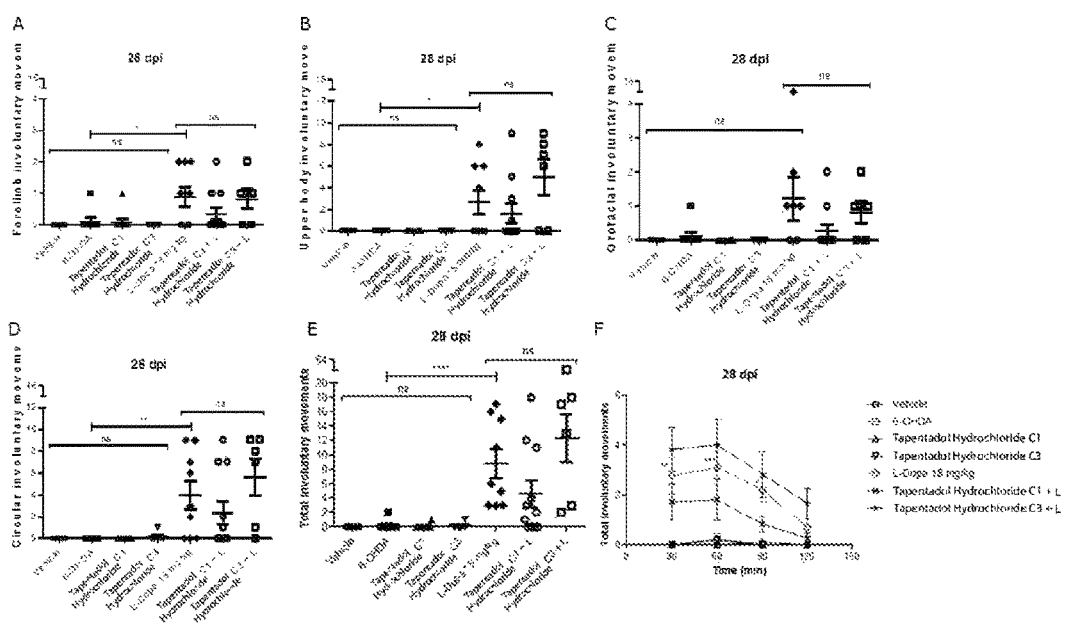
Figures 30A-F

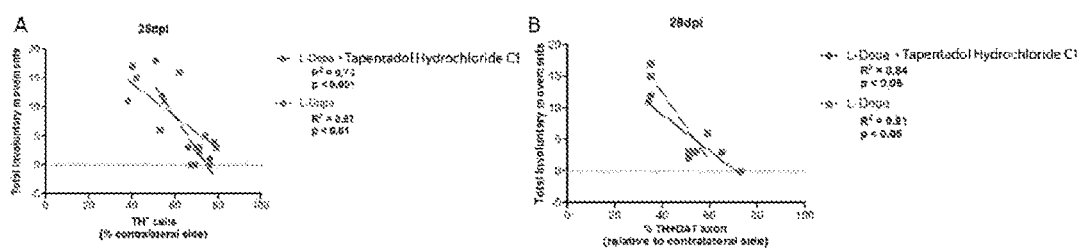
Figures 31A-B

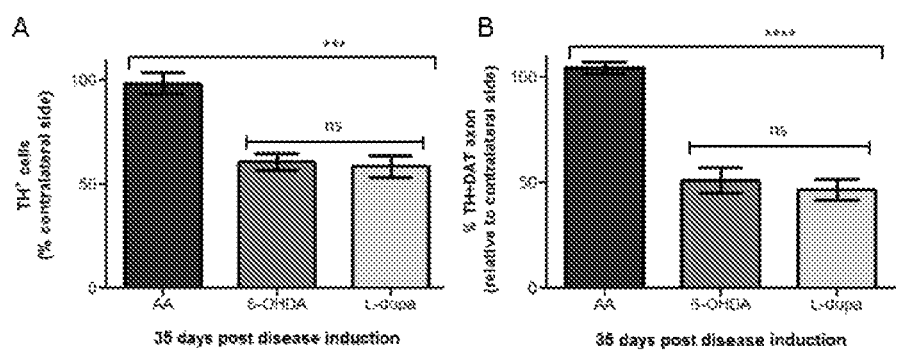
Figures 32A-B

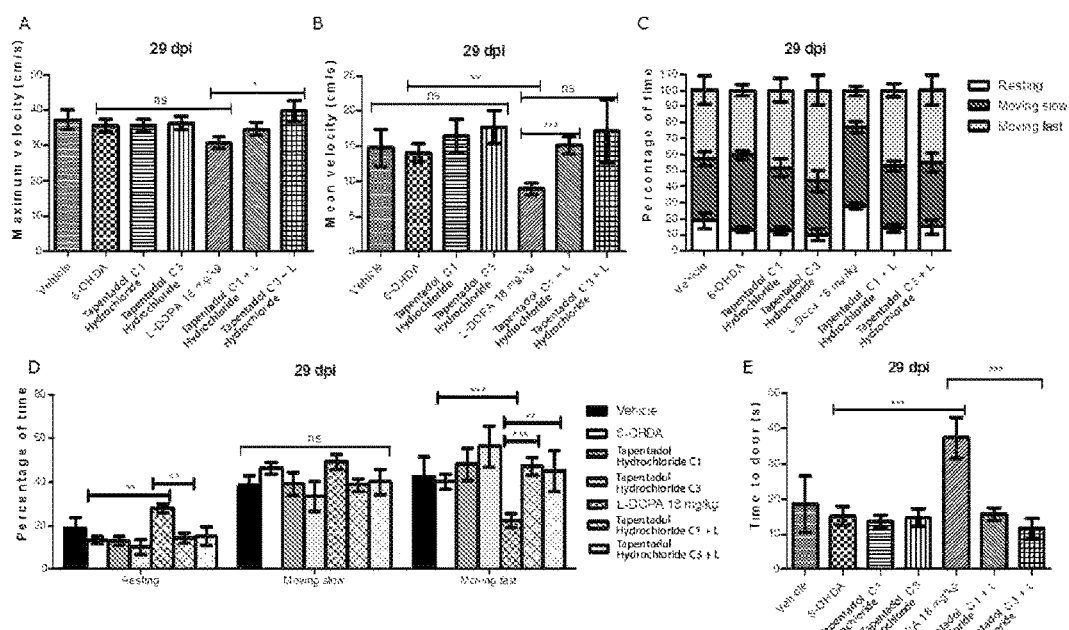
Figures 33A-E

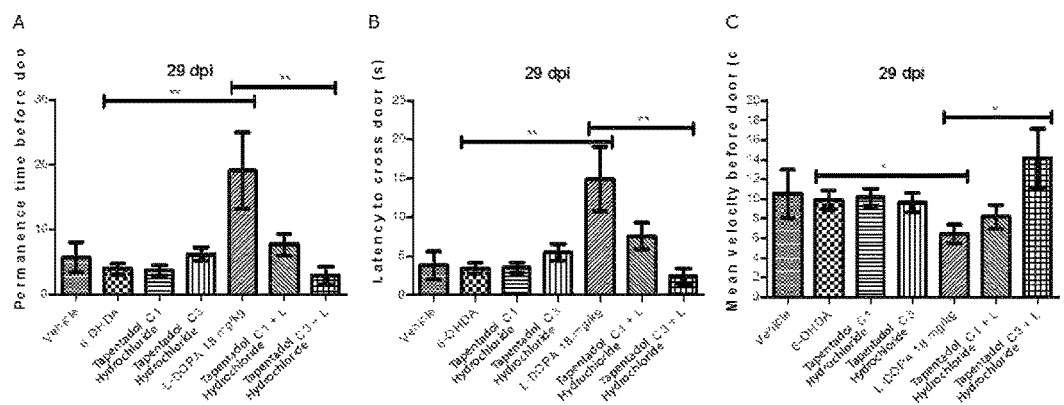
Figures 34A-C

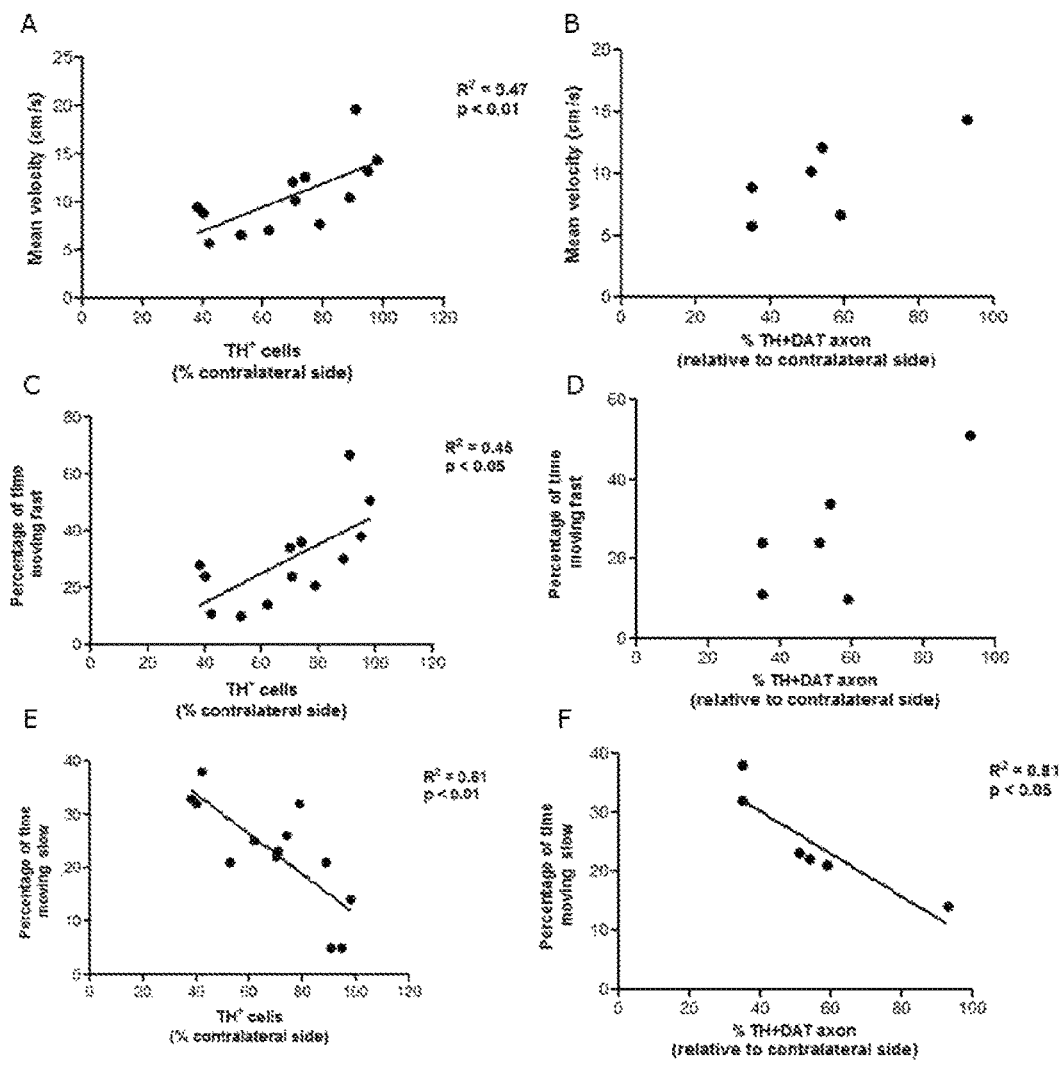
Figures 35A-L

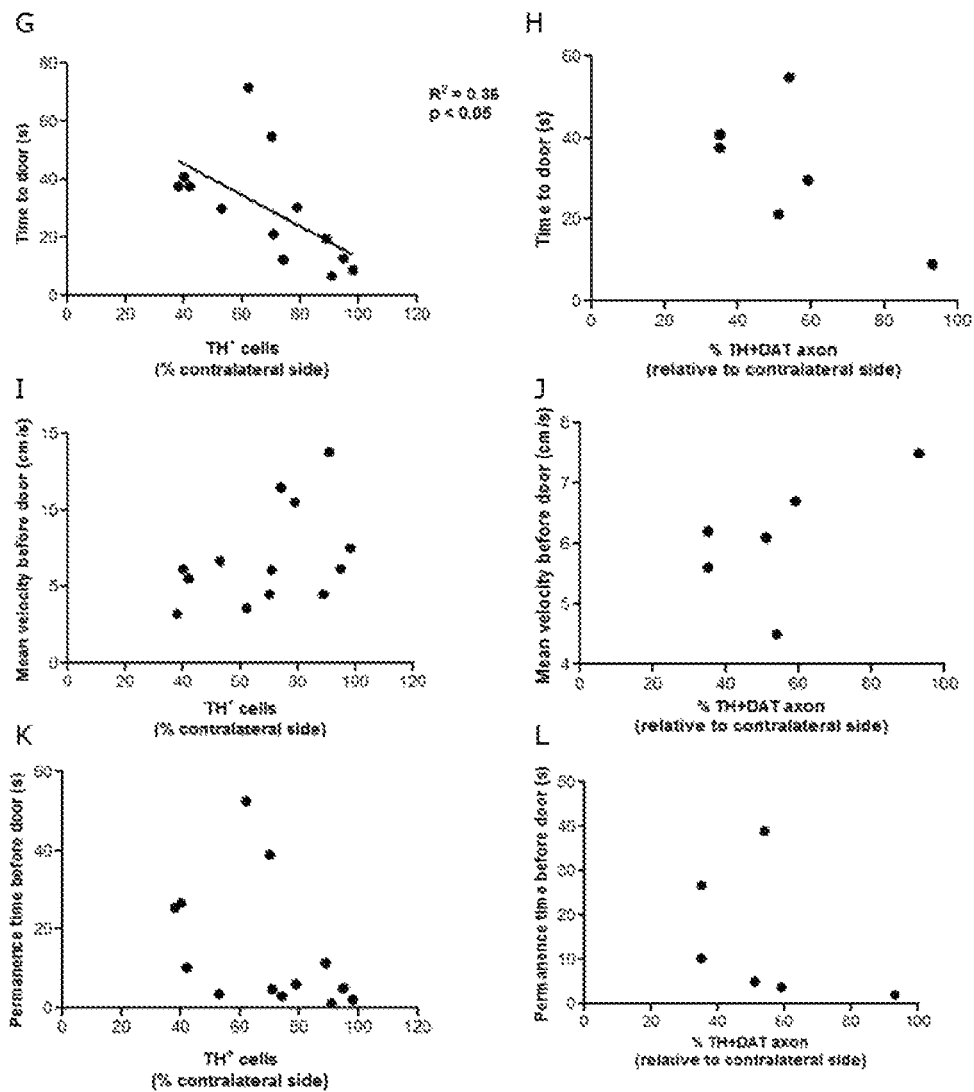
Figures 35A-L (Cont'd)

COMPOSITIONS FOR USE IN TREATING PARKINSON'S DISEASE AND RELATED DISORDERS

FIELD OF THE INVENTION

The present invention relates to methods of treating and managing Parkinson's disease and related disorders. The methods especially find use in managing motor symptoms, including gait problems, particularly during advanced stages when effectiveness of standard medications wear off or side effects become problematic, as seen in Parkinson's disease, other disorders treated with dopaminergic agents, and other conditions associated with motor problems, such as aging or stroke. The treatment also may include disease-modifying effects, neuroprotection of, or neurorescue effects on neuronal cells in patients with Parkinson's disease and other neurodegenerative disorders. In particular, the invention relates to methods of administering pharmaceutical compositions comprising effective amounts of tapentadol or a pharmaceutically acceptable salt or derivative thereof or, in other embodiments, stavudine or nabumetone or a derivative thereof, for treating symptoms associated with Parkinson's disease, either as individual active agents, in combination with each other, or in combination with agents known to treat Parkinson's disease, such as the dopaminergic agent levodopa. The invention also relates to methods of preparing pharmaceutical compositions comprising effective amounts of tapentadol, stavudine, or nabumetone, or a derivative thereof, further in combination with a dopaminergic agent, or derivative thereof, as well as to methods of using the pharmaceutical compositions in treating Parkinson's disease, related disorders, other conditions treated with dopaminergic agents, and other conditions with gait problems, for example by oral administration of the compositions.

BACKGROUND

Parkinson's Disease (PD) is a common neurodegenerative disease, that is characterized neuropathologically by the degeneration of heterogeneous populations of neural cells (mainly dopaminergic neurons in substantia nigra) involving different neurotransmitter systems and different regions of the nervous system. The degeneration of the pigmented neurons in the pars compacta of the substantia nigra accounts for most of the distinctive motor symptoms. Neuropathological diagnosis requires the presence of eosinophilic cytoplasmatic inclusions, that is, Lewy bodies, or aggregations of misfolded synuclein in the remaining neural cells and other brain regions.

Clinical diagnosis of PD requires bradykinesia (motor impairment) and at least one of the following: resting tremor, muscular rigidity, and postural reflex impairment, which are considered the core symptoms of the disease. Misclassifications, especially in early-stage PD, occur frequently. However, around 75% of PD diagnoses will be correct, where 2 out of the 4 core symptoms are present and other neurological signs or symptoms are absent. In addition, Magnetic Resonance Imaging may be helpful for excluding other Parkinsonian syndromes. Nonetheless, in 15%-25% of the clinical diagnosis, PD cannot be confirmed histopathologically and there is an urgent need for biomarkers for PD diagnosis.

There also remains an urgent need for better treatments, for example, therapeutics that halt further neurodegeneration and delay disease progression. Nonetheless, the mechanisms responsible for the dopaminergic cell loss in PD are unknown. Moreover, no pharmacotherapy currently exists that shows a relevant delay in disease progression, as current pharmacological intervention in PD involves addressing the symptoms of PD. In particular, there remains a need for therapeutics with a pharmacology to improve PD's impaired dopaminergic neurotransmission. Patients with early stages of PD may start, depending on the clinical context, with a dopamine-agonist or a dopamine precursor, such as L-Dopa. In general, a patient with early stages PD starts treatment with dopamine-agonists; if symptoms are insufficiently controlled, L-Dopa is added during the course of the disease. In advanced PD, most patients receive both L-Dopa and a dopamine-agonist.

Nonetheless, the effectiveness of L-Dopa decreases over time and non-responsive periods to this therapeutic approach increase during advanced stages of the disease. In particular, L-Dopa control of motor symptoms decreases as its efficacy wears off, and symptoms do not improve until the next dose is taken. Motor symptoms oscillate between OFF periods (medication withdrawal), which are times of decreased mobility and re-emergence of symptoms; and ON periods (after L-dopa intake), which are periods when the medication works and symptoms are controlled. With disease progression, these motor fluctuations become difficult to predict and can be dramatic in advanced PD, for patients taking high L-Dopa doses. During OFF periods, patients suffer highly impaired mobility and reduced quality of life. For example, patients taking L-Dopa for a long time and/or in high doses experience 'OFF_ periods in L-Dopa efficacy and need therapeutic alternatives that do not further exacerbate the developing side effects.

Most of the treatments that are used as alternatives or adjuncts to L-Dopa aim to increase ON periods but none, however, whether taken alone or in combination with others, has been able to eliminate wearing off completely. The lack of alternative therapeutic options for these periods, together with an aggravation of the symptoms, are major concerns.

Studies of non-motor manifestations in patients with PD have shown that long-term L-Dopa treatment may promote the development of not only motor fluctuations, but also mood fluctuations, and significant mood changes have been found to be associated with ON/OFF phenomena in PD patients. Specific tests for anxiety and for a depressive state would provide a better and specific assessment of non-motor manifestations.

Moreover, an adverse side effect of L-Dopa is the development of motor complications during the course of the disease, following chronic use of L-Dopa. Unfortunately, however, the mechanisms leading to these motor complications are not fully understood. Most likely, the effect of L-Dopa is modified as a consequence of the continuing loss of dopaminergic cells as there is no evidence that L-Dopa itself has a deleterious effect on the PD patients disease progression. L-Dopa dose-limiting factors are believed to be the cause of involuntary movements (dyskinesias, dystonia, choreaathetosis), psychiatric side effects (e.g. hallucinations, delusions, psychosis), and autonomic side effects (e.g. orthostatic hypotension).

Current dopamine-agonists act directly on the dopamine receptors. Nonetheless, compared to L-Dopa, dopamine-agonists are relatively less effective and have a higher incidence of psychiatric and autonomic side effects. Other drug categories, such as monoamine oxidase inhibitors, catecholamine-O-methyl transferase inhibitors, anticholinergics, and glutamate modulators may represent alternative or, more often, adjunctive treatments to L-Dopa and dopamine-agonists.

There also remains an unmet need in PD regarding the symptom of 'freezing of gait_, both from the clinician's and the patient's point of view. This is often a dramatic symptom, common in advanced PD, that highly impairs mobility, causes falls, and reduces quality of life. For these reasons, freezing of gait is an important clinical problem to be addressed. Nonetheless, the pathogenesis of freezing of gait is not understood and empirical treatments show poor efficacy. Non-pharmacological interventions include deep brain structures stimulation and neuronal grafts, which both have limited application. Deep brain structures stimulation is limited to highly selected patient groups; neuronal grafts mainly are investigational.

Accordingly, there remains a need in the art for therapeutics useful in treating and managing PD and related disorders, in particular, a need for therapeutics that help manage motor and non-motor symptoms during OFF periods, after chronic L-Dopa administration, and attendant motor side effects, such as problems with gait, as well as managing other conditions with associated gait problems. In particular, there remains an unmet need during advanced stages of PD, when the effectiveness of L-Dopa wears off and side effects become problematic, especially motor symptoms. There also remains an unmet need to reduce OFF periods, to make them more predictable, and to be able to continue treatment with low L-Dopa doses. Approaches that address these needs with few side effects and low risk of toxicity, even after chronic use, especially are needed. The instant invention addresses these and other needs.

SUMMARY OF THE INVENTION

The present invention provides improved methods of treating, preventing, or ameliorating the symptoms of a neurological disorder, particularly a neurodegenerative disease, more specifically Parkinson's disease. In particular, the methods address the increased side effects, reduction in efficacy, and increase in 'OFF period_ frequency in patients suffering from Parkinson's and chronically administered a dopaminergic agent, such as L-Dopa.

One aspect of the invention relates to methods comprising administration of an effective amount of tapentadol, or a pharmaceutically effective salt thereof or derivative thereof, to a patient suffering from Parkinson's to treat, prevent, or ameliorate the symptoms of Parkinson's disease. The invention also relates to an effective amount of tapentadol, or a pharmaceutically effective salt or derivative thereof, for use in treating, managing, or preventing symptoms of a neurological disorder, such as Parkinson's, a related disorder, or other condition where a dopaminergic agent, such as L-Dopa, is chronically administered.

In preferred embodiments, the method comprises administering an effective dose of tapentadol to a Parkinsonian patient to manage motor and/or non-motor symptoms during OFF periods of L-Dopa treatment, more preferably where the motor symptom is selected from dyskinesia, dystonia, chorea, athetosis, motor fluctuation, and postural abnormality; and/or where the non-motor symptom is selected from speech impairment, autonomic dysfunction, orthostatic hypotension, mood swings, anxiety, depression, cognitive impairment, psychosis, hallucinations, and delusions. In particularly preferred embodiments, administration of tapentadol reduces or eliminates OFF periods, smoothing out motor fluctuations between ON/OFF periods, otherwise seen in advanced Parkinson's disease.

In some embodiments, methods of the invention comprise administration of tapentadol in combination with a dopaminergic agent, such as L-Dopa, or administration to a patient who has or is taking L-Dopa or who has become refractory to L-Dopa. In particular embodiments, the methods comprise administering the same, similar, or higher amounts of tapentadol compared with doses currently in use. In some embodiments, the tapentadol component is tapentadol hydrochloride. In some embodiments, the tapentadol component is the tapentadol derivative tramadol.

Another aspect of the invention relates to pharmaceutical compositions comprising tapentadol, a pharmaceutically effective salt or derivative thereof, in combination with an agent known to treat Parkinson's disease or a related disorder or a derivative of said agent, preferably where the agent is a dopaminergic agent, such as L-Dopa or a derivative thereof. In particular embodiments, the pharmaceutical compositions comprise the same, similar, or higher amounts of tapentadol compared with doses currently in use; and/or the tapentadol component is tapentadol hydrochloride. In some embodiments, the pharmaceutical composition does not comprise tramadol. In some embodiments, the invention relates to methods of making such pharmaceutical compositions, e.g., by mixing with a pharmaceutically acceptable carrier. In a particular embodiment, the pharmaceutical compositions are formulated for oral administration, e.g., in tablets, capsules, powders, or solutions, preferably tablets or capsules formulated for immediate release of the tapentadol component.

Still another aspect of the invention relates to methods comprising administration of an effective amount of stavudine and/or nabumetone, or a pharmaceutically effective salt or derivative of either, to a patient suffering from a neurological disorder, particularly neurodegenerative disease, such as Parkinson's, to treat, prevent, or ameliorate the symptoms of the disease or disorder. The invention also relates to use of an effective amount of stavudine and/or nabumetone, or a pharmaceutically effective salt or derivative of either, for treating, managing, or preventing symptoms of the neurological disorder. In particular embodiments, stavudine and/or nabumetone, or the pharmaceutically effective salt or derivative of either, may be administered in combination with tapentadol, or a pharmaceutically effective salt or derivative thereof, and/or in combination with L-Dopa.

Yet another aspect of the invention relates to pharmaceutical compositions comprising stavudine and/or nabumetone, or a pharmaceutically effective salt or derivative of either, in combination with a dopaminergic agent, such as L-Dopa or a derivative thereof. In some embodiments, the pharmaceutical compositions further comprise a tapentadol component. In some embodiments, the invention relates to methods of making such pharmaceutical compositions, e.g., by mixing with a pharmaceutically acceptable carrier.

BRIEF DESCRIPTION OF THE FIGURES

FIGS. 3A-3D: L-Dopa dose response curves, showing effective concentrations for long range (FIG. 3A) and small range (FIG. 3B) phenotype recovery; as well as the lack of ability to recover affected neurons where the disease is induced strongly (sig ****) (FIG. 3C), but neuroprotective effects where the disease is less severe (sig *) (FIG. 3D), where 'sig_ indicates statistical significance with a t-student test; * indicates p<0.05; *** indicates p<0.001).

FIGS. 4A-4E: Isradipine dose response curves, showing effective concentrations in terms of total distance moved for long range (FIG. 4A) and small range (FIGS. 4B-4C) phenotype recovery, as well as ability to recover affected neurons in terms of total cell neurons (FIGS. 4D-4E).

FIGS. 5A-5D: Rasagiline dose response curves, showing effective concentrations for long range (FIG. 5A) and small range (FIG. 5B) phenotype recovery; as well as ability to recover affected neurons (FIGS. 5C-5D).

FIGS. 6A-6G: Tapentadol dose response curves, showing effective concentration for phenotype recovery of locomotor behavior of 6-OHDA-treated zebrafish larvae, based on total distance moved (FIG. 6A) and number of jumps (FIG. 6B), as well as duration of freezing steps (FIG. 6C) and number of dopaminergic neurons positive for Tyrosine hydroxylase (Th) in the control (non-6-OHDA), disease state (6-OHDA), and 6-OHDA larvae treated with 48.5 μM of tapentadol (FIG. 6D); along with representative immunohistochemistry Z-projections in control larvae (FIG. 6E), 6-OHDA larvae (FIG. 6F), and tapentadol treated-larvae (FIG. 6G).

FIGS. 7A-7G: Stavudine dose response curves, showing effective concentration for phenotype recovery of locomotor behavior of 6-OHDA-treated zebrafish larvae, based on total distance moved (FIG. 7A) and number of jumps (FIG. 7B), as well as duration of freezing steps (FIG. 7C) and number of dopaminergic neurons positive for Tyrosine hydroxylase (Th) in the control (non-6-OHDA), disease state (6-OHDA), and 6-OHDA larvae treated with 30 and 50 μM of stavudine (FIG. 7D); along with representative immunohistochemistry Z-projections in control larvae (FIG. 7E), 6-OHDA larvae (FIG. 7F), and stavudine treated-larvae (FIG. 7G).

FIGS. 8A-8G: Nabumetone dose response curves, showing effective concentration for phenotype recovery of locomotor behavior of 6-OHDA-treated zebrafish larvae, based on total distance moved (FIG. 8A) and number of jumps (FIG. 8B), as well as duration of freezing steps (FIG. 8C) and number of dopaminergic neurons positive for Tyrosine hydroxylase (Th) in the control (non-6-OHDA), disease state (6-OHDA), and 6-OHDA larvae treated with 0.456 and 0.91 μM nabumetone (FIG. 8D); along with representative immunohistochemistry Z-projections in control larvae (FIG. 8E), 6-OHDA larvae (FIG. 8F), and nabumetone treated-larvae (FIG. 8G).

FIGS. 9A-9D: Recovery of freezing of gait results using control molecules (FIG. 9A), candidate molecules (FIGS. 9B-9C), and combinations thereof (FIG. 9D).

FIGS. 12A-12F: Rotarod test results in 6-OHDA-treated mice, following treatment with L-Dopa or tapentadol hydrochloride, at 2 different concentrations, based on latency to fall (FIG. 12A) and speed (FIG. 12B); following treatment with L-Dopa or stavudine, at 2 different concentrations, based on latency to fall (FIG. 12C) and speed (FIG. 12D); and following treatment with a L-Dopa or combination of tapentadol hydrochloride and stavudine, based on latency to fall (FIG. 12E) and speed (FIG. 12F).

FIGS. 13A-13D: Cylinder test results in 6-OHDA-treated mice, before initiation of treatment, based on evaluating percentage of contralateral paw use (FIG. 13A), number of right turns (FIG. 13B), number of rearings (FIG. 13C), and percentage of animals with tremor (FIG. 13D) per group.

FIGS. 14A-14D: Cylinder test results in 6-OHDA-treated mice, following treatment with L-Dopa or tapentadol hydrochloride at 2 different concentrations, based on evaluating percentage of contralateral paw use (FIG. 14A), number of right turns (FIG. 14B), number of rearings (FIG. 14C), and percentage of animals with tremor (FIG. 14D) per group.

FIGS. 15A-15D: Cylinder test results in 6-OHDA-treated mice, following treatment with L-Dopa or stavudine, at two different concentrations, based on evaluating percentage of contralateral paw use (FIG. 15A), number of right turns (FIG. 15B), number of rearings (FIG. 15C), and percentage of animals with tremor (FIG. 15D) per group.

FIGS. 16A-16D: Cylinder test results in 6-OHDA-treated mice, following treatment with L-Dopa or a combination of tapentadol hydrochloride and stavudine, each at two different concentrations, based on evaluating percentage of contralateral paw use (FIG. 16A), number of right turns (FIG. 16B), number of rearings (FIG. 16C), and percentage of animals with tremor (FIG. 16D) per group.

FIGS. 17A-17F: Abnormal involuntary movements results, evaluated 28 days post injection of L-Dopa, tapentadol hydrochloride at two different concentrations, stavudine at two different concentrations, or a combination thereof, based on evaluating forelimb involuntary movements (FIG. 17A), upper body involuntary movements (FIG. 17B), orofacial involuntary movements (FIG. 17C), circular involuntary movements (FIG. 17D), total involuntary movements (FIG. 17E), and number of left turns (FIG. 17F).

FIGS. 18A-18D: Open field test results following administration of L-Dopa or tapentadol hydrochloride, at two different concentrations, based on evaluating maximum velocity (FIG. 18A), total distance moved (FIG. 18B), mean velocity (FIG. 18C), and latency to first reach the walls (FIG. 18D).

FIGS. 19A-19D: Open field test results following administration of L-Dopa or stavudine, at two different concentrations, based on evaluating maximum velocity (FIG. 19A), total distance moved (FIG. 19B), mean velocity (FIG. 19C), and latency to first reach the walls (FIG. 19D).

FIGS. 20A-20D: Open field test results following administration of L-Dopa or a combination of tapentadol hydrochloride and stavudine, each at two different concentrations, based on evaluating maximum velocity (FIG. 20A), total distance moved (FIG. 20B), mean velocity (FIG. 20C), and latency to first reach the walls (FIG. 20D).

FIGS. 21A-21F: Cell loss induced by unilateral intracranial injection of 6-OHDA, evaluated by TH-positive cell counts in the ipsilateral (left) and contralateral (right) side of injection, in terms of microscope images of TH-stained sections of the substantia nigra pars compacta from a healthy control mouse (FIG. 21A) and disease induced mice that are not treated (FIG. 21B) or that are treated with L-Dopa (FIG. 21C), tapentadol hydrochloride (FIG. 21D), or stavudine (FIG. 21E), as well as in terms of the percentage of TH-positive cells in the ipsilateral versus contralateral side of injection in each of these groups (FIG. 21F).

FIGS. 22A-22F: Open field test results in toxicity assay of tapentadol hydrochloride or tramadol, each in combination with L-Dopa, based on evaluating the six parameters maximum velocity (FIG. 22A), mean velocity (FIG. 22B), total distance moved (FIG. 22C), time spent resting (FIG. 22D), time spent moving slow (FIG. 22E), and time spent moving fast (FIG. 22F).

FIGS. 24A-24B: Gait test plan for testing efficacy of tapentadol hydrochloride administered with L-Dopa during ON period (FIG. 24A) and administered at higher doses during L-Dopa OFF period (FIG. 24B).

FIGS. 25A-25B: Cylinder test results for vehicle and 6-OHDA treated mice, based on evaluating percentage of contralateral paw use (FIG. 25A) and number of right turns (FIG. 25B).

FIGS. 26A-26B: Cylinder test results for different therapeutic groups, namely, 6-OHDA, L-Dopa, tapentadol hydrochloride at concentration C1, tapentadol hydrochloride at C1+L-Dopa, tapentadol hydrochloride at concentration C3, and tapentadol hydrochloride at C3+L-Dopa treated mice, in terms of evaluating percentage of contralateral paw use (FIG. 26A) and number of right turns (FIG. 26B).

FIGS. 27A-27G: Microscope images of Tyrosine hydroxylase-stained (red) and Dopamine transporter-stained (DAT in green) sections of the striatum from healthy control mice (FIG. 27A), 6-OHDA disease induced mice (FIG. 27B), and disease-induced groups treated with L-Dopa (FIG. 27C), tapentadol hydrochloride at two different concentrations (FIGS. 27D-27E), and with a combination of L-Dopa and tapentadol hydrochloride at two different concentrations (FIGS. 27F-27G); yellow labelling indicates the co-localization of TH and DAT markers.

FIGS. 28A-28C: Results for cell loss induced by unilateral intracranial injection of 6-OHDA in control mice and different treatment groups, based on TH-positive cell counts in the ipsilateral (left) and contralateral (right) side of injection (FIG. 28A) and by TH-DAT double positive axons in the striatum (FIG. 28B), as well as Pearson˜s correlation between TH-positive cell counts and TH-DAT double positive axons in the striatum (FIG. 28C).

FIGS. 29A-29F: Abnormal involuntary movements results, evaluated 20 days post injection of L-Dopa, in different treatment groups, evaluated in terms of forelimb involuntary movements (FIG. 29A), upper body involuntary movements (FIG. 29B), orofacial involuntary movements (FIG. 29C), circular involuntary movements (FIG. 29D), total involuntary movements (FIG. 29E), and total involuntary movements along the different timepoints (FIG. 29F).

FIGS. 30A-30F: Abnormal involuntary movements results, evaluated 28 days post injection of a higher L-Dopa dose, in different treatment groups, evaluated in terms of forelimb involuntary movements (FIG. 30A), upper body involuntary movements (FIG. 30B), orofacial involuntary movements (FIG. 30C), circular involuntary movements (FIG. 30D), total involuntary movements (FIG. 30E), and total involuntary movements along the different timepoints (FIG. 30F).

FIGS. 31A-31B: Pearson˜s correlation between the number of TH-positive cells (FIG. 31A) or TH-DAT axons (FIG. 31B) with total AIMs in the L-dopa treated groups.

FIGS. 32A-32B: Results for cell loss induced by unilateral intracranial injection of 6-OHDA in control mice and L-Dopa treated 6-OHDA mice, based on TH-positive cell counts in the ipsilateral (left) and contralateral (right) side of injection (FIG. 32A), and by TH-DAT double positive axons in the striatum (FIG. 32B).

FIGS. 33A-33E: Gait test results at 29 days post injection (dpi), showing tapentadol hydrochloride-treated animals˜ behavioral recovery in maximum velocity (FIG. 33A), mean velocity (FIG. 33B), and percentage of time resting or moving fast (FIG. 33C) amongst various treatment groups; and similar results regarding moving slow (FIG. 33D, showing decomposition of the plot in FIG. 33C) and time that the animal took to reach the door (FIG. 33E).

FIGS. 34A-34C: Gait test results at 29 days post injection (dpi), showing behavioral recovery for tapentadol hydrochloride-treated animals in terms of permanence time before the door (FIG. 34A), latency to cross the door (FIG. 34B), and mean velocity before the door (FIG. 34C), compared with various treatment groups.

FIGS. 35A-35L: Behavioral impairment correlations with the degree of cell loss, based on linear regression between mean velocity and nigral TH+ cell loss (FIG. 35A) or striatal axonal denervation (FIG. 35B); linear regression between percent of time moving fast and nigral TH+ cell loss (FIG. 35C) or striatal axonal denervation (FIG. 35D); linear regression between percent of time moving slow and nigral TH+ cell loss (FIG. 35E) or striatal axonal denervation (FIG. 35F); linear regression between time to the door and nigral TH+ cell loss (FIG. 35G) or striatal axonal denervation (FIG. 35H); linear regression between mean velocity before the door and nigral TH+ cell loss (FIG. 35I) or striatal axonal denervation (FIG. 35J); and linear regression between permanence before the door and nigral TH+ cell loss (FIG. 35K) or striatal axonal denervation (FIG. 35L).

DETAILED DESCRIPTION

1. Definitions

Figure 1:
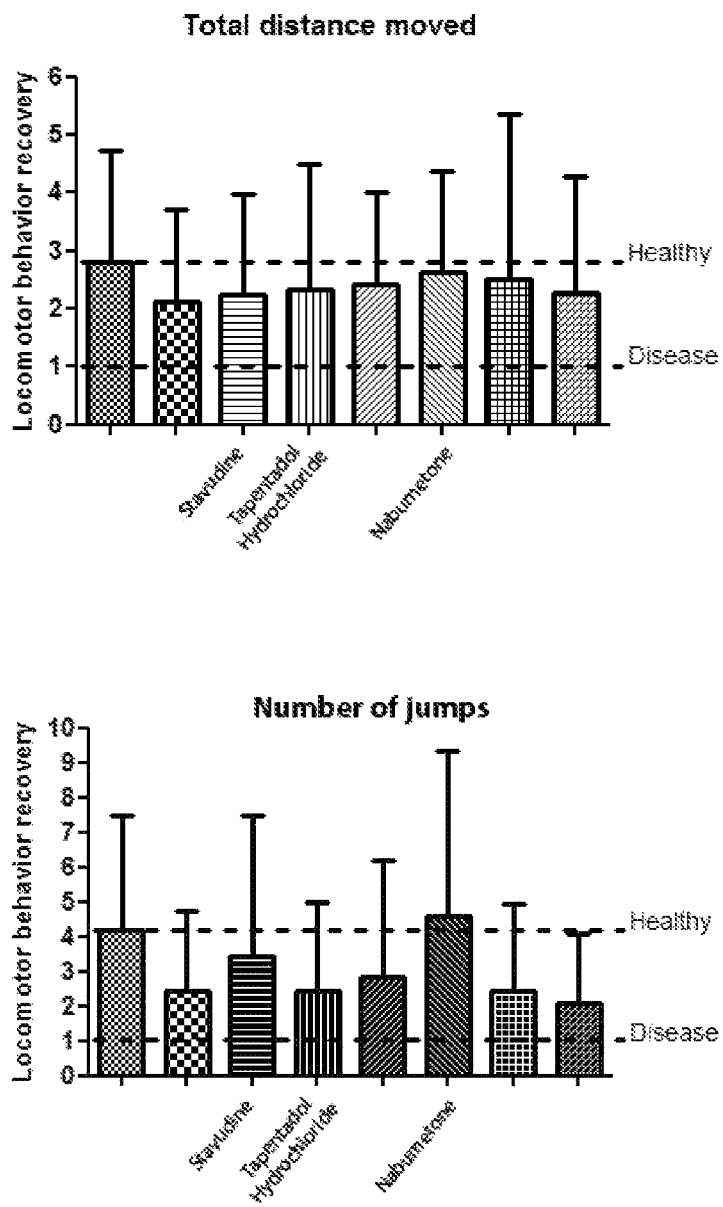
FIGS. 1A-1B: Locomotor behavior rescue results for each of 7 candidate molecules, based on total distance moved (FIG. 1A) and number of jumps (FIG. 1B) in 6-OHDA treated zebrafish larvae.

By 'neurological disease or disorder_ is meant a disease or disorder of the nervous system including, but not limited to, epilepsy, global and focal ischemic and hemorrhagic stroke, head trauma, spinal cord injury, hypoxia-induced nerve cell damage as in cardiac arrest or neonatal distress, and neurodegenerative disease.

By 'neurodegenerative disease_ is meant diseases including, but not limited to, Parkinson˜s Disease, Alzheimer˜s Disease, Huntington˜s Disease, and amyotrophic lateral sclerosis (ALS). Parkinson˜s disease (PD), also referred to as idiopathic or primary parkinsonism, hypokinetic rigid syndrome (HRS), or paralysis agitans, is a degenerative disorder of the central nervous system mainly affecting the motor system. The motor symptoms of the disease are due to death of dopamine-generating cells in the substantia nigra, a region of the midbrain. Early in the disease, the most obvious symptoms are movement-related, such as shaking, rigidity, slowness of movement, and difficulty with walking and gait. Later, thinking and behavioral problems may arise, as well as depression, with dementia commonly occurring in the advanced stages of the disease. Other symptoms include sensory, sleep and emotional problems.

An 'advanced stage_ of PD, or a related disorder, refers to a stage of the disease or disorder characterized by worsening symptoms, worsening side effects, and/or less responsiveness to standard treatments compared to an earlier stage in the disease or disorder. An advanced stage may occur later in the time course of the disease, e.g., 1 year, 2 years, 5 years, 10 years, 15 years or more since initial diagnosis of PD or the related disorder. An advanced stage may correspond to a time following chronic use of L-Dopa (levodopa), e.g., when side effects of levodopa develop and/or worsen; when PD or a related disorder is less responsive to levodopa than it was at an earlier stage; when higher levodopa doses are administered compared to an earlier stage; and/or when there are OFF periods between levodopa doses.

An 'OFF period_, 'OFF time_, or 'OFF episode_ refers to a functional state when a patient with PD or a related disorder has poor response, despite taking a therapeutic, or has a response typical of when no therapeutic had been taken. This period also commonly is referred to as a 'bad time_, 'low time_, 'slow time_ or 'shaking time_, or simply the 'time when the medication doesn't work_. In particular, an 'OFF period_ during L-Dopa therapy in PD, or a related disorder, is a period, time, or episode during which the efficacy of L-Dopa lessens or wears off, leading to re-emergence of one or more symptoms associated with PD, especially re-appearance of motor symptoms, until the next dose of L-Dopa is taken by the patient. OFF periods in PD are characterized by decreased or highly impaired mobility. OFF periods oscillate with 'ON periods_, when L-Dopa is more effective, leading to motor fluctuations that can become unpredictable and dramatic in advanced PD.

An 'ON period_ or 'ON time_ refers to a functional state when a patient with PD or a related disorder experiences the therapeutic benefit of an agent being taken, having a good response. This period also commonly is referred to as the 'good time_ or 'walking time_, or simply the 'time when the medication works_.

A 'motor fluctuation_ is a motor symptom of OFF periods and refers to a variable response to a therapeutic, such as oscillating ON/OFF periods during L-Dopa therapy in PD or a related disorder. Motor fluctuations occur with predictable wearing-off of a therapeutic, or with unpredictable ON/OFF periods, as well as with sudden 'OFF periods_. 'Motor fluctuations_ also commonly are referred to as 'uneven medication effects_ or 'roller-coaster effects_ and reflect the wearing off of therapeutic efficacy between doses.

'Dyskinesia_ refers to involuntary random movement. Dyskinesia is a typical side effect of chronic use of L-Dopa, characteristic of advanced stages of PD, or related disorders, such as when higher doses of L-Dopa are used due to decreasing L-Dopa effectiveness in controlling symptoms of PD or related disorders. Dyskinesia commonly also is called 'irregular jerking_, 'wiggling_, or 'twitching_ and is distinct from tremor characteristic of PD itself.

'Dysotnia_ refers to contorted posture, often associated with a twisting component and also commonly is referred to as a 'spasm_ or 'cramp_, or simply a 'posture_.

'Orthostatic hypotension_ is defined as a drop in systolic blood pressure of greater than or equal to 20 mm Hg or of diastolic blood pressure of greater than or equal to 10 mm Hg, within 3 min of standing or upon head-up tilt (minimum 60 é) on a tilt table.

A 'disorder related to_ Parkinson's disease, or a 'related disorder_, includes any neurological disease or disorder, including any neurodegenerative disease, e.g., as defined herein. A related disorder also may refer to any side effect associated with standard therapeutic agents used in managing Parkinson's, such as the side effects of chronic levodopa use in Parkinson's disease or other disorder where levodopa is administered, or the side effects of use of any other dopaminergic agents.

As used herein, the terms 'subject_, host_, and 'patient_ are used interchangeably. As used herein, a subject is preferably a mammal such as a non-primate (e.g., cows, pigs, horses, cats, dogs, rats, mice etc.) or a primate (e.g., monkey and human), most preferably a human.

As used herein, the term 'oral administration_ (or the like) with respect to the mammal (preferably, human) means that the mammal ingests or is directed to ingest (preferably, for the purpose of treating or preventing a disease, disorder, or condition described herein) one or more pharmaceutical compositions for use in the present invention.

As used herein, the term 'immediate release_ regarding oral formulations, in particular, refers to a composition that, when administered, releases the active agent within a small period of time. Immediate release typically means that about 75% of the active agent is dissolved within 45 minutes of administration. The term 'rapidly dissolving_ typically means that about 85% is dissolved in 30 minutes and 'very rapidly dissolving_ typically means about 85% is dissolved in 15 minutes of administration. Oral formulations for immediate release drug delivery systems are a conventional type of drug delivery system designed to disintegrate and release their pharmaceutically active agent without rate controlling features, such as special coatings or other delay techniques.

As used herein, the term 'therapeutic agent_ refers to any agent which can be used in treating, managing, or ameliorating symptoms associated with Parkinson's disease, or a related disorder, or other condition where a dopaminergic agent, such as L-Dopa, is chronically administered.

As used herein, a 'therapeutically effective amount_ refers to the amount of agent, (e.g., an amount of tapentadol, stavudine, and/or nabumetone for use in the invention) that provides at least one therapeutic benefit in the treatment or management of the target disease or disorder, when administered to a subject suffering therefrom. Further, a therapeutically effective amount with respect to an agent for use in the invention means that amount of agent alone, or when in combination with other therapies, that provides at least one therapeutic benefit in the treatment or management of the disease or disorder.

In the case of Parkinson's disease, the therapeutically effective amount of the therapeutic molecule may reduce the one or more movement-related symptoms, such as shaking, rigidity, slowness of movement, and difficulty with walking and gait; a thinking or behavioral problem, such as anxiety, depression, or dementia; or sensory, sleep, or emotional problems associated with the disease. A therapeutically effective amount also may refer to the amount to reduce a side effect of chronic use of a standard treatment, e.g., the amount to reduce side effects associated with chronic L-Dopa usage.

As used herein, the term 'prophylactic agent_ refers to any agent which can be used in the prevention, delay, or slowing down of the progression of Parkinson's disease, or a related disorder, or other condition where a dopaminergic agent, such as L-Dopa, is chronically administered. As used herein, a 'prophylactically effective amount_ refers to the amount of the prophylactic agent (e.g., an amount of tapentadol, stavudine, and/or nabumetone for use in the invention) that provides at least one prophylactic benefit in the prevention, reduction, or delay of the target disease or disorder, when administered to a subject predisposed thereto.

A prophylactically effective amount also may refer to the amount of agent sufficient to prevent, reduce the incidence of, or delay the occurrence of the target disease or disorder; or slow the progression of the target disease or disorder; the amount sufficient to delay or minimize the onset of the target disease or disorder; or the amount sufficient to prevent or delay the recurrence or spread thereof, or to reduce the incidence thereof. A prophylactically effective amount also may refer to the amount of agent sufficient to prevent or delay the exacerbation of symptoms of a target disease or disorder or the amount of agent sufficient to prevent or delay the exacerbation of side effects of a standard treatment of the target disease or disorder. Further, a prophylactically effective amount with respect to a prophylactic agent for use in the invention means that amount of prophylactic agent alone, or when in combination with other agents, that provides at least one prophylactic benefit in the prevention or delay of the disease or disorder, a symptom thereof or side effect associated with the treatment thereof.

A prophylactic agent for use in the invention can be administered to a subject 'pre-disposed_ to a target disease or disorder, that is, pre-disposed to Parkinson˜s disease, or a related disorder, or other condition where a dopaminergic agent, such as L-Dopa, is chronically administered. A subject that is 'pre-disposed_ to a disease or disorder is one that shows symptoms associated with the development of the disease or disorder, or that has a genetic makeup, environmental exposure, or other risk factor for such a disease or disorder, but where the symptoms are not yet at the level to be diagnosed as the disease or disorder. For example, a patient with a family history of Parkinson˜s disease may qualify as one predisposed thereto.

As used herein a 'dopaminergic agent_ refers to any therapeutic or prophylactic agent that acts to affect dopamine receptors or dopamine release through indirect action, for example, by acting on neurons that synapse onto neurons that release dopamine or express dopamine receptors. Examples include levodopa, which is converted in the brain into dopamine, as well as dopamine agonists that mimic the effects of dopamine.

2. Therapeutic and Prophylactic Methods of Use

The present invention provides improved methods of treating, preventing, or ameliorating the symptoms of a neurological disorder, particularly a neurodegenerative disease, by administering a pharmaceutical composition comprising an active agent, where the active agent is tapentadol, or a pharmaceutically effective salt or derivative thereof. In particular embodiments, the pharmaceutical composition is administered to address increased side effects, reduction in efficacy, and increase in 'OFF period_ frequency and/or duration in patients chronically administered a dopaminergic agent, such as L-Dopa.

One aspect of the present invention relates to therapies which involve administering an effective amount of an active agent described herein (in particular, tapentadol) to a subject in need thereof, for delaying, preventing, treating, and/or managing a neurological disease or disorder, and/or ameliorating one or more symptoms associated therewith and/or one or more side effects associated with treatment thereof. A subject in need thereof includes a subject suffering from the disease or disorder, or a subject pre-disposed thereto, e.g., a subject at risk of developing or having a recurrence of the disease or disorder; and/or at risk of developing or having a side effect due to chronic treatment of the underlying disease or disorder.

The neurological disorder may include any disease or disorder of the nervous system such as, but not limited to, epilepsy, global and focal ischemic and hemorrhagic stroke, head trauma, spinal cord injury, hypoxia-induced nerve cell damage as in cardiac arrest or neonatal distress, and neurodegenerative disease. See, e.g., U.S. Pat. No. 6,071,970, to Mueller et al. describing such diseases and disorders, which is incorporated herein in its entirety. Neurological disorders include neurodegenerative diseases, such as, but not limited to, Parkinson˜s Disease, Alzheimer˜s Disease, Huntington˜s Disease, and amyotrophic lateral sclerosis (ALS). Neurological disorders also include conditions with associated gait problems, including any condition involving impaired movement, such as Parkinson˜s disease, aging, stroke, or restless leg syndrome. See, e.g., WO 2008/079404 (Spherics, Inc.) to Nangia et al., describing such disorders and diseases, which is incorporated herein in its entirety. Also included are other conditions in which side effects develop due to chronic use of dopaminergic agents, such as chronic use of levodopa.

Parkinson˜s disease presents a number of symptoms, changing and often worsening with disease progression. Early in the disease, the most obvious symptoms are movement-related, such as shaking, rigidity, slowness of movement, and difficulty with walking and gait. Later, thinking and behavioral problems may arise, as well as anxiety and depression, with dementia commonly occurring in the advanced stages of the disease. Other symptoms include sensory, sleep and emotional problems.

A motor symptom of importance to patients involves problems with gait. Gait is defined as the pattern of movement of the limbs during locomotion. Parkinsonian gait is characterized by: small shuffling steps, general slowness of movement (bradykinesia), and total loss of movement (akinesia) in extreme cases. General PD patients have a reduced stride length and walking speed (slow little steps), difficulty at initiating steps and at stopping after starting walking, as well as difficulty distributing equally the force through all the foot, postural instability (head and neck forward, with flexion at the knees), accelerating steps (festination), muscle rigidity, and freezing of gait (FoG).

Freezing of Gait (FoG) can be defined as a brief, episodic absence or marked reduction of forward progression of the feet despite the intention to walk. Current treatments rarely reduce freezing once it had developed. In the pipeline, is sublingual apomorphine (Phase II concluded; see, e.g., Cynapsus poster, Hauser, et al. 'Efficacy of Sublingual Apomorphine Film Strip (APL-130277) for the Treatment of OFF Episodes in Patients with Parkinson's Disease_ American Academy of Neurology, Friday, Apr. 15 to Thursday, Apr. 21, 2016; Vancouver, BC, Canada). Freezing as a primary endpoint in clinical trials remains a looming challenge, because the measurements are subjective (FoG questionaries). Indeed, the majority of the studies conducted have been small and uncontrolled.

Further, the pathogenesis of this symptom is not well understood. K nown clinical features and circumstances that precede/precipitate FoG are trying to start to walk, turning, approaching/passing through narrow passages, approaching an object, dual tasking, distractions, crowded places, being under time pressure, stress, and anxiety states. There also are several 'types_ of FoG:

1) Freezing that occurs during ON period of L-Dopa that can be controlled by reducing/adjusting L-Dopa treatment;

2) Freezing that occurs during OFF period of L-Dopa that is more common and responds to treatments that improve ON time but at this time L-Dopa can no longer be administered (12 h interval);

3) Freezing that is induced by L-Dopa; and

4) Freezing that is resistant to L-Dopa (non-responsive).

FoG remains largely untreated under current treatment approaches.

Another concern of importance to patients is problems during advanced or later stages of PD, or a related disorder, due to worsening symptoms, worsening side effects, and/or less responsiveness to standard treatments compared to initial stages of the disease or disorder. Late symptoms became evident as L-Dopa efficacy wears off, leading to OFF periods.

Without being bound to a particular theory, OFF periods may occur because brain dopamine levels fall below a critical threshold to sustain relatively normal motor function, typical of ON periods. OFF periods can be predictable or unpredictable and, in some cases, OFF periods may be preceded by non-motor symptoms, such as pain, tingling, sweating, and anxiety, possibly alerting the patient to the fact that motor symptoms are returning. OFF periods generally are categorized into the following 4 main types, over the course of a day:

(1) Morning OFF periods-occurring after the previous last dose of a dopaminergic agent, such as L-Dopa or other PD medication that was taken the previous evening, and resulting in a delayed response to the first morning dose. Specifically, after a night of sleep, little or no dopaminergic agent remains in the patient˜s brain, leaving only a small reserve of dopaminergic stimulation, and resulting in significant delay in responding to the first morning dose of L-Dopa or other PD medication. This 'morning OFF period_ also is referred to as 'morning akinesia_. This delayed response is unpredictable such that the patient cannot rely on the onset of L-Dopa or other PD medication in the morning. Further, impaired gastric motility and erratic gastric emptying in PD patients may delay or prevent L-Dopa absorption. Morning OFF periods typically are considered the most debilitating OFF periods and can be the most difficult to treat or to convert to ON.

(2) Delayed ON, Partial ON, or Delayed or Partial Drug Failure¯occurring when a patient takes a dose of L-Dopa or other PD medication, but does not achieve ON in the usual time frame. To the patient, it appears that the dose has not worked properly. A Partial ON is characterized by the patient experiencing some improvement in motor function, but not enough to perform daily activities. In contrast, a dose failure is characterized by the patient not experiencing any response to a given dose. A Delayed ON, Partial ON, or dose failure may occur for a number of reasons. For example, oral delivery of L-Dopa requires the drug to be actively absorbed through the gastrointestinal tract into the blood stream. As the gut contains dopaminergic neurons that can become depleted of dopamine, however, when this occurs, the gut may fail to function normally, resulting in delayed, limited, or no absorption of the dose. These OFF episodes are also difficult to convert to ON and typically do not respond to adjunctive PD medications.

(3) End of dose wearing-off OFF periods¯these are the most common type of OFF periods. For example, with PD progression, L-Dopa˜s effect decreases in duration. Eventually, L-Dopa stops being fully effective between doses, which causes a patient to go 'OFF_ ahead of the next L-Dopa dose. These OFF periods occur in a relatively predictable fashion, following each dose of L-Dopa.

(4) Unpredictable OFF periods¯OFF periods occurring without warning and at unexpected times when the patient is in the ON state. The goal of L-Dopa therapy is to maintain a constant blood level of L-Dopa, expected to result in a constant supply of L-Dopa to the brain and, therefore, a constant level of dopamine and dopaminergic stimulation. The brain, however, does not utilize dopamine at a constant rate. Changes in activity level or mood, such as agitation or anxiety, result in an increased use of dopamine. The brain then depletes the reserves of dopamine, and more time is required to re-build that dopamine deficit. As a result, a patient in the ON state can unexpectedly and suddenly turn OFF, during a time when the normal PD medication typically would be effective.

OFF periods can have a tremendous negative impact on patients˜ daily lives, recognized by the patients, caregivers, and clinicians. The potential for unexpected loss of motor function, or the unpredictable onset of benefit, of the PD medication can result in patients avoiding certain social settings and/or hindering performance of simple daily tasks, such as eating, bathing, dressing, etc. Further, a patient˜s varying consumption of dopamine from variable 'daily stresses_, as well as the loss of dopaminergic cells, exacerbates the frequency, duration, and severity of OFF episodes. As the disease progresses, patients are often forced to leave the workforce and become increasingly dependent on caregivers.

The present invention, in some embodiments, provides methods of treatment, prophylaxis, and amelioration of one or more symptoms associated with Parkinson˜s disease, or one or more side effects of L-Dopa administration, a related disorder, a condition associated with gait problems, or other condition treated with a dopaminergic agent, by administering to a subject an effective amount of a pharmaceutical composition described herein. In a particular embodiment, the invention provides methods of treatment, prophylaxis, and amelioration of one or more symptoms associated with OFF periods in Parkinson˜s disease or a related disorder, or one or more side effects associated with long term use of L-Dopa, in particular by administering an effective amount of a tapentadol-containing pharmaceutical composition. In some embodiments, methods comprise administering an effective amount of stavudine, or a pharmaceutically effective salt or derivative thereof, to a patient suffering from Parkinson˜s disease or a related disorder. In some embodiments, methods comprise administering an effective amount of nabumetone, or a pharmaceutically effective salt or derivative thereof, to a patient suffering from Parkinson˜s disease or a related disorder. The effective amount generally determines the dosage selected for formulation and/or the dosage regimen, such as the frequency and mode of administration. Dosage amounts and dosage regimens provided herein are encompassed by the terms therapeutically effective amount and prophylactically effective amount.

In some embodiments, the instant methods reduce the severity, duration, and/or frequency of one or more symptoms typical of OFF periods. For example, the methods may reduce severity of OFF periods, such that the patient experiences less motor fluctuations or fewer side effects during OFF periods. In particular embodiments, for example, the methods may reduce duration of OFF periods by at least about 10%, at least about 20%, at least about 30%, at least about 40%, at least about 50%, at least about 60%, at least about 70%, at least about 80%, or at least about 90% compared with the duration of OFF periods after the same L-Dopa treatment but in the absence of tapentadol treatment. In particular embodiments, for example, the methods may reduce frequency of OFF periods by at least about 10%, at least about 20%, at least about 30%, at least about 40%, at least about 50%, at least about 60%, at least about 70%, at least about 80%, or at least about 90% compared with the frequency of OFF periods after the same L-Dopa treatment but in the absence of tapentadol treatment.

In preferred embodiments, the instant methods reduce the severity, duration, and/or frequency of motor fluctuations, a common motor symptom during OFF periods. Motor fluctuations result from variable responses to the therapeutic being administered, such as L-Dopa, reflecting the wearing off of therapeutic efficacy between doses and resulting in oscillating ON/OFF periods. Motor fluctuations may correspond to predictable wearing-off of a therapeutic, or to unpredictable ON/OFF periods, as described above, as well as to sudden 'OFF periods_. In preferred embodiments, methods of the invention reduce the variability of response to a domaminergic agent, such as L-Dopa, e.g., lengthening ON periods and/or reducing delayed responses, thus reducing oscillations between ON/OFF periods during doses.

In a particularly preferred embodiment, methods of the invention reduce severity, frequency, and/or duration of morning akinesia, reducing the delayed response to a patients morning L-Dopa dose or other PD medication. In some embodiments, methods of the invention reduce severity, frequency, and/or duration of the end of dose wearing-off OFF periods, so that the patient experiences less of a 'roller coaster effect_ between doses. In more preferred embodiments, the methods reduce and/or eliminate unpredictability of OFF periods, reducing the number of such periods experienced between doses and/or reducing the length of time such periods last and/or the extent mobility is impaired during those periods. In most preferred embodiments, OFF periods are prevented, eliminated or nearly eliminated, in that the patient experiences no or little variability in response, steadily maintaining motor function and mobility, e.g., as was the case during earlier stages of the disease.

In preferred embodiments, the instant methods reduce the severity, duration, and/or frequency of dyskinesia, another common motor symptom during OFF periods. Dyskinesia involves involuntary random movement, typically experienced after chronic use of L-Dopa, such as during advanced stages of PD, or related disorders, when effectiveness of the drug wears off and higher doses are needed. In a particularly preferred embodiment, the method reduces how often, how long, and/or to what extent the patient experiences an 'irregular jerking_, wiggling_, or 'twitching_, which otherwise may become severe in advanced Parkinson˜s disease. For example, administration of an effective dose of tapentadol, in accordance with methods herein, may reduce dyskinesia during OFF periods, such that less, preferably far less, dyskinesia occurs and/or, if it occurs, the jerking or twitching lasts shorter and is less severe. In most preferred embodiments, dyskinesia is prevented, eliminated, or nearly eliminated, in that the patient experiences no or little involuntary random movements, e.g., as was the case during earlier stages of the disease.

Levodopa-induced dyskinesia often involves specific hyperkinetic movements, including dystonia, chorea, and athetosis.

In preferred embodiments, the instant methods reduce dysotnia, another common motor symptom during OFF periods. Dysotnia involves involuntary contorted posture, often associated with a twisting component, typically experienced after chronic use of L-Dopa, such as during advanced stages of PD, or related disorders, when effectiveness of the drug wears off and higher doses are needed. In a particularly preferred embodiment, the method reduces how often, how long, and/or to what extent the patient experiences a dysotonic 'spasm_ or 'cramp_, which otherwise may become severe in advanced Parkinson˜s disease. For example, administration of an effective dose of tapentadol, in accordance with methods herein, may reduce dysotnia during OFF periods, such that less, preferably far less, spasms or cramps occur and/or, if they occur, the spasms or cramps last shorter and are less severe. In most preferred embodiments, dysotnia is prevented, eliminated or nearly eliminated, in that the patient experiences no or little spasms, twisting, or cramping, e.g., as was the case during earlier stages of the disease.

In preferred embodiments, the instant methods reduce chorea and/or athetosis. Chorea involves continuous jerky movements in which each movement is sudden and the resulting posture is held for a few seconds. The focus may move from one part of the body to another at random, generally affecting the head, face, or limbs. Athetosis involves sinuous, slow, involuntary writhing movements affecting the fingers, hands, toes, and feet, as well as the arms, legs, neck, and tongue. In a particularly preferred embodiment, the method reduces how often, how long, and/or to what extent the patient experiences the continuous jerky movements of chorea and/or the sinuous slow writhing movements of athetosis. For example, administration of an effective dose of tapentadol, in accordance with methods herein, may reduce chorea and/or athetosis during OFF periods, such that less, preferably far less, continuous jerky movements and/or sinuous writhing movements occur and, if they occur, the movements last shorter and are less severe. In most preferred embodiments, chorea and/or athetosis is prevented, eliminated, or nearly eliminated, in that the patient experiences no continuous jerky movements or sinuous writhing movements, e.g., as was the case during earlier stages of the disease.

In preferred embodiments, the instant methods reduce the severity, duration, and/or frequency of non-motor symptoms, also commonly experienced during OFF periods, such as speech impairment, autonomic dysfunction, orthostatic hypotension, mood swings, anxiety, depression, cognitive impairment, psychosis, hallucinations, and delusions.

In preferred embodiments, the instant methods reduce or alleviate speech impairment. Speech impairment may involve changes in the patient˜s speech, where speech becomes softer, quicker, more monotone, or slurred, or the patient may hesitate before talking. In a particularly preferred embodiment, the method reduces how often, how long, and/or to what extent the patient experiences speech impairment. For example, administration of an effective dose of tapentadol, in accordance with methods herein, may reduce or alleviate speech impairment, such that the patient experiences fewer changes, preferably far fewer changes, in his/her speech and/or, if changes occurs, they are not as dramatic or noticeable. In most preferred embodiments, speech impairment is prevented, eliminated, or nearly eliminated, in that the patient experiences no or little problems speaking, e.g., as was the case during earlier stages of the disease.

In preferred embodiments, the instant methods reduce or alleviate orthostatic hypotension. Over the course of Parkinson˜s, autonomic degeneration impairs the sympathetic response to baroreceptor input. Upon standing, patients with advanced Parkinson˜s may become unable to compensate for venous pooling and reduced venous return, caused by compromised autonomic reflexes, thus experiencing a drop in blood pressure, along with presyncopal symptoms and difficulty maintaining an upright posture. In a particularly preferred embodiment, the method reduces how often, how long, and/or to what extent the patient experiences orthostatic hypotension. For example, administration of an effective dose of tapentadol, in accordance with methods herein, may reduce or alleviate orthostatic hypotension, such that the patient experiences fewer, preferably far fewer, drops in blood pressure upon standing. In most preferred embodiments, orthostatic hypotension is prevented, eliminated, or nearly eliminated, in that the patient experiences no or little problems with falling blood pressure upon changing to an upright position, e.g., as was the case during earlier stages of the disease.

Non-motor symptoms of OFF periods include mood swings. In preferred embodiments, the method of the invention reduces how often, how long, and/or to what extent the patient experiences mood swings. A patient with advanced Parkinson˜s may alternate between feelings of hopelessness, anxiety, and anger. In preferred embodiments of the invention, administration of an effective dose of tapentadol may reduce or alleviate changes in mood, such that the patient experiences fewer, preferably far fewer, swings in temperament. In most preferred embodiments, mood swings are prevented, eliminated or nearly eliminated, in that the patient experiences no or little alternating moods, e.g., as was the case during earlier stages of the disease.

In preferred embodiments, the instant methods reduce or alleviate depression, particularly depression during OFF periods. Depression in Parkinson's patients may be difficult to diagnose, as sharing many symptoms with the underlying disease, including fatigue, loss of interest in normal activities, sleep problems, slowness of movement, lack of facial animation, etc. Depressed patients also may experience feelings of sadness, worthlessness, guilt, or irritability. In preferred embodiments, the instant methods reduce or alleviate depression. In a particularly preferred embodiment, the method reduces how often, how long, and/or to what extent the patient experiences feelings of sadness, worthlessness, guilt, or irritability, and/or reduces fatigue, alleviates loss of interest in normal activities, and improves sleep. For example, administration of an effective dose of tapentadol, in accordance with methods herein, may reduce or alleviate depression, such that the patient experiences fewer, preferably far fewer, bouts of sadness or guilt. In most preferred embodiments, depression is prevented, eliminated or nearly eliminated.

In preferred embodiments, the instant methods reduce or alleviate anxiety, particularly anxiety during OFF periods. Parkinson's patients may experience generalized anxiety, where the patients become so worried that they cannot sleep, or they experience a racing heartbeat, shortness of breath, and sweating. During advanced stages, Parkinson's patients further may experience anxiety when their levodopa or dopamine agonist drugs start wearing off, in some cases leading to extreme anxiety and panic attacks. In preferred embodiments, the instant methods reduce or alleviate anxiety and panic attacks. In a particularly preferred embodiment, the method reduces how often, how long, and/or to what extent the patient experiences worry that causes lack of sleep, racing heartbeat, shortness of breath, and/or sweating. For example, administration of an effective dose of tapentadol, in accordance with methods herein, may reduce or alleviate anxiety, such that the patient experiences fewer, preferably far fewer, bouts of racing heartbeat, shortness of breath, and/or sweating, and/or, if they occur, the anxiety is less acute and/or lasts for a shorter period of time. In most preferred embodiments, anxiety is prevented, eliminated, or nearly eliminated, e.g., in that the patient experiences negligible anxiety and/or no panic attacks, similar to the patients experience during earlier stages of the disease.

Non-motor symptoms of OFF periods include dementia and/or cognitive impairment. In preferred embodiments, the instant methods reduce or alleviate dementia and/or cognitive impairment, in particular dementia and/or cognitive impairment associated with OFF periods. Most people with Parkinson's disease experience mild cognitive changes, such as those affecting attention, memory, mental processing speed, problem-solving, processing of visual information, and recalling the right words from ones vocabulary. In some cases, however, and more often during advanced stages of the disease, dementia may develop, involving severe impairment of memory and thinking, along with confusion, disorientation, and difficulty judging spatial relationships. In a particularly preferred embodiment, methods of the invention delay, reduce, or alleviate dementia and/or cognitive impairment. For example, administration of an effective dose of tapentadol, in accordance with methods herein, may delay, reduce, or alleviate cognitive changes, allowing the patient to better retain attention, memory, mental processing speed, and/or problem-solving abilities. In some preferred embodiments, administration of an effective dose of tapentadol, in accordance with methods herein, may delay, reduce, or alleviate one or more symptoms of dementia, including reducing confusion, disorientation, and/or difficulty judging spatial relationships. In most preferred embodiments, dementia and/or cognitive impairment is prevented, eliminated, or nearly eliminated, e.g., in that the patient experiences no or little problems with severe cognitive impairment and no dementia.

Non-motor symptoms of OFF periods include psychosis, such as hallucinations and delusions. In preferred embodiments, the instant methods reduce or alleviate symptoms of psychosis, such as hallucinations and/or delusions, in particular, hallucinations and delusions associated with OFF periods. In Parkinson's patients, hallucinations often are benign at first, such as involving visions of children or animals around the home. During later stages, however, patients may experience serious psychosis, involving delusions (false or illogical beliefs) and paranoia (such as becoming convinced that others are spying on them). In a particularly preferred embodiment, methods of the invention delay, reduce, or alleviate hallucinations and/or delusions. For example, administration of an effective dose of tapentadol, in accordance with methods herein, may delay, reduce, or alleviate hallucinations and/or delusions, reducing frequency and/or duration of visions or delusions, or making delusions seem less real. In most preferred embodiments, hallucinations and/or delusions are prevented, eliminated, or nearly eliminated, e.g., in that the patient experiences no or little visions and/or no delusions.

Non-motor symptoms of OFF periods include sleep disorders, such as sleep apnea and REM sleep behavior disorder. In preferred embodiments, the instant methods reduce or alleviate sleep disorders, such as sleep apnea and REM sleep behavior disorder, in particular, sleep disorders associated with OFF periods. Sleep apnea involves interrupted breathing episodes during slumber. REM sleep behavior disorder involves 'acting out_ vivid dreams, sometimes leading to punching or kicking bed partners. In a particularly preferred embodiment, methods of the invention delay, reduce, or alleviate sleep disorders. For example, administration of an effective dose of tapentadol, in accordance with methods herein, may delay, reduce, or alleviate sleep apnea and/or REM sleep behavior disorder. In most preferred embodiments, sleep disorders are prevented, eliminated, or nearly eliminated, e.g., in that the patient experiences no or little sleep apnea and/or REM sleep behavior disorders.

In some embodiments, methods of the invention comprise administration of a therapeutically effective amount of a pharmaceutical composition described herein, such as a composition comprising tapentadol or a derivative of tapentadol, or in alternative embodiments, comprising stavudine, a derivative of stavudine, nabumetone, or a derivative of nabumetone. In preferred embodiments, the invention provides methods of treating, preventing, or reducing the incidence of OFF episodes in a subject experiencing or at risk for OFF episodes, particularly a subject in the advanced stages of Parkinson's disease, by administering an effective dose of tapentadol.

In a particular embodiment, methods of the invention comprise administration of an effective amount of tapentadol in combination with L-Dopa, to a patient that has become refractory to L-Dopa or is experiencing side effects of L-Dopa administration, preferably where the L-Dopa dose reduced. For example, the L-Dopa dose may be reduced by 1/10, 1/8, 1/5, 1/4, 1/3, 1/2, or less of the dose that typically would be administered to the patient, at a given stage of Parkinson's, in the absence of tapentadol. Administration during refractory periods can reduce the severity, duration, and/or frequency of one or more symptoms typical of OFF periods, as described above. For example, the methods may reduce severity of OFF periods, such that the patient experiences less motor flucutations or fewer side effects during OFF periods.

A pharmaceutical composition for use in the invention generally will be administered for a time and in an amount effective for obtain a desired therapeutic and/or prophylactic benefit. In preferred embodiments, the effective amounts formulated and/or administered do not cause substantial toxicity, even with chronic use. The data obtained from the cell culture assays and animal studies can be used in formulating a range and/or schedule for dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized.

The dosage and frequency may vary according to factors specific for each patient depending on the specific therapeutic or prophylactic agents administered, the severity and type of disease, the route of administration, as well as age, body weight, response, and the past medical history of the patient, and is decided, in some embodiments, according to the judgment of the practitioner and each patient's circumstances. Suitable doses and regimens can be selected by one skilled in the art by considering such factors and by following, for example, dosages reported in the literature and recommended in the Physician's Desk Reference ($56^{th}$ ed., 2002). Prophylactic and/or therapeutic agents can be administered repeatedly. Several aspects of the procedure may vary such as the temporal regimen of administering the prophylactic or therapeutic agents, and whether such agents are administered separately or as an admixture.

The amount of an agent for use in the invention to provide a therapeutically and/or prophylactically effective dose can be determined by clinical techniques, in view of the disclosures presented herein. For example, effective doses may be extrapolated from dose-response curves derived from in vitro or animal model test systems, such as a neurotoxin 6-OHDA (6-hyroxydopamine) based model, in particular, the 6-OHDA zebrafish and 6-OHDA mice models. Such information can be used to more accurately determine useful doses in humans. Levels in plasma may be measured, for example, by high performance liquid chromatography.

Prophylactic and/or therapeutic agents, as well as combinations thereof, can be tested in suitable animal model systems prior to use in humans, e.g., 6-OHDA mice models. Such animal model systems include, but are not limited to, zebrafish, rats, mice, chicken, cows, monkeys, pigs, dogs, rabbits, etc. Any animal system well-known in the art may be used, such as model systems widely used and well known to the skilled artisan. In some preferred embodiments, animal model systems for Parkinson's disease, a disorder related thereto, or a condition mimicking advanced stages of PD when OFF periods appear, are used that are based on fish, rats, mice, or other small mammals. For example, in a specific embodiment, putative prophylactic and/or therapeutic compositions of tapentadol, stavudine, and/or nabumetone are tested in a 6-OHDA zebrafish or 6-OHDA mouse model system. In another specific embodiment, putative prophylactic and/or therapeutic compositions comprising tapentadol alone, or in combination with L-Dopa, are tested in a 6-OHDA zebrafish or 6-OHDA mouse model system.

Once the prophylactic and/or therapeutic agents have been tested in an animal model, they can be tested in clinical trials to establish their efficacy. Establishing clinical trials will be done in accordance with common methodologies known to one skilled in the art, and the optimal dosages and routes of administration as well as toxicity profiles of agents described herein can be established. For example, a clinical trial can be designed to test a pharmaceutical composition comprising both levodopa and tapentadol for efficacy and toxicity in human patients with Parkinson's disease. In some embodiments, one or more of tapentadol, stavudine, and nabumetone is administered in a dose of about 0.1 mg to about 1,000 mg to treat a Parkinson's disease, a disorder related thereto, condition associated with gait problems, or other condition treated with a dopaminergic agent, or to ameliorate a side effect of chronic treatment of the underlying disease or disorder.

Toxicity and efficacy of the prophylactic and/or therapeutic agents of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

Further, effective doses and dosage regimens can be selected by one skilled in the art, considering the present disclosures regarding certain characteristics of tapentadol, stavudine, and/or nabumetone in the context of Parkinson's disease, a disorder related thereto, a condition associated with gait problems, or managing a side effect of chronic treatment of the underlying disease or disorder. Characteristics of each of tapentadol, stavudine, and nabumetone, as the active agent, and effective amounts thereof, are described below with respect to making and using pharmaceutical compositions for use in Parkinson's disease, a disorder related thereto, condition associated with gait problems, or other condition treated with a dopaminergic agent.

3. Pharmaceutical Compositions for Use in the Present Invention

Pharmaceutical compositions comprising tapentadol or a pharmaceutically effective salt or derivative thereof are described below, as well as pharmaceutical compositions comprising stavudine, nabumetone, or a pharmaceutically effective salt or derivative of either.

Tapentadol-Containing Pharmaceutical Compositions

Tapentadol-containing pharmaceutical compositions for use in the present invention include tapentadol as the active agent for use in treatment, prevention, or amelioration of Parkinson's disease, a related disorder, or a condition associated with a symptom thereof or side effect associated with the treatment thereof. The term 'tapentadol_ or 'tapentadol hydrochloride_ as used herein relates to a compound having the brand names 'PALEX IA÷ (Infarmed; MA Holder: Grænthal, S. A.), NUCY NTA± (FDA; MA Holder: Janssen Pharmaceuticals, Inc.), or TAPAL± (India; MA Holder: MSN Labs), and has been identified by the number '175591-23-8_. Information regarding this therapeutic can be found, for example, through the FDA or from the drug bank listing (http://www.drugbank.ca/drugs/DB06204 (Drugbank, Tapentadol drug entry created on Mar. 19, 2008 10:17; updated on May 23, 2016 02)). The compound is classified as an analgesic, specifically, a ≈-opioid agonist, that currently is indicated for the relief of moderate to severe acute pain in adults, where the pain can only be adequately controlled with opioid analgesics.

Tapentadol has been described as a centrally-acting synthetic analgesic. The exact mechanism of action is unknown. Besides acting as a ≈-opioid receptor (MOR) agonist, preclinical studies have shown that tapentadol also acts as a norepinephrine reuptake inhibitor (NRI). Analgesia in animal models is derived from both of these activities of the compound (see, e.g., Highlights of Prescribing Information for NUCY NTA±, Reference ID: 3400040, Janssen Pharmaceuticals, Inc. 2009, revised 2013). Indeed, tapentadol causes large increases in levels of extracellular norepinephrine (NE) due to a dual mechanism of action involving ≈-opioid receptor (MOR) agonism, as well as noradrenaline reuptake inhibition (see, e.g., http://www.drugbank.ca/drugs/DB06204; Drug Bank, tapentadol drug entry created on Mar. 19, 2008 10:17; updated on May 23, 2016 02:34). For example, tapentadol has been shown to inhibit norepinephrine reuptake in the brains of rats, resulting in increased norepinephrine concentrations. In preclinical models, the analgesic activity due to the I -opioid receptor agonist activity of tapentadol can be antagonized by selective I -opioid antagonists (e.g., naloxone), whereas the norepinephrine reuptake inhibition is sensitive to norepinephrine modulators. Tapentadol exerts its analgesic effects without a pharmacologically active metabolite Tapentadol is designated as 'Class 1_ (high permeability, high solubility) in the Biopharmaceutics Classification System and tapentadol hydrochloride is considered a stable substance (see, e.g., WHO Expert Committee on Drug Dependence 35$^{th}$ Meeting, Hammamet Tunisia, 4-8 Jun. 2012, Agenda item 5.2, Tapentadol Pre-Review Report). For example, a re-test period of 30 months with storage below 25 éC has been approved. In some embodiments, the invention provides methods and compositions comprising tapentadol, which is 1-phenyl-3-dimethlaminopropane and has the structure below, Formula I

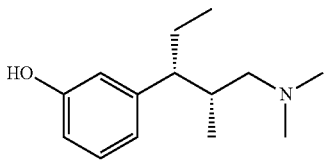

Formula I

See also, e.g., U.S. Pat. No. RE39,593 to Buschmann et al., incorporated herein in its entirety. Tapentadol commonly is isolated as the hydrochloride salt. Other salts and/or forms of tapentadol also are envisioned for use in the invention. For example, a pharmaceutical composition for use in the invention may comprise any polymorphic form of tapentadol, in particular, any freely soluble form within a physiological pH range, including, e.g., a hydrate and/or a solvate form (see also, e.g., tapentadol salts described in US 2011/0071120 A1, incorporated herein in its entirety).

The invention also contemplates other forms of tapentadol hydrochloride, including isomers, other salts, and other derivatives thereof, preferably where the derivative maintains therapeutic or prophylactic activity with respect to Parkinson's disease, a related disorder, a symptom thereof, or a side effect associated with the treatment thereof. Derivatives of tapentadol may include, e.g., tramadol or other structurally-related opioid agonists. In some embodiments, derivatives maintain the dual effects of ≈-opioid agonism and noradrenaline uptake. In further embodiments, the derivatives maintain only one of these two effects, or maintain one to a greater, or substantially greater effect than the other. For example, derivatives of tapentadol are envisioned that maintain effect on noradrenaline re-uptake to a greater extent than ≈-opioid agonism.

In some preferred embodiments, the composition comprises, and/or the methods administer, tapentadol hydrochloride in an amount greater than the lowest dose of tapentadol currently on the market, e.g., 1.5, 2, 2.5, or 3 times the lowest dose on the market, more preferably 2.5 times the lowest dose. In more particularly preferred embodiments, the composition comprises tapentadol hydrochloride as the sole active ingredient in an amount greater than the lowest dose, e.g., 1.5, 2, 2.5, or 3 times the lowest dose, more preferably 2.5 times the lowest dose of tapentadol currently on the market. For comparison, 50 mg every 4 to 6 hours is the lowest dose used in the U.S. Approved doses include 50 mg, 75 mg, and 100 mg, every 46 hours; the maximum approved dose is 700 mg administered on the first day of treatment and 600 mg thereafter. In extended release format, the recommended dose is 50 mg over 12 hours and up to 500 mg/day.

In some embodiments, a pharmaceutical composition of the invention further comprises, or methods of treatment further comprise administration of, methylphenidate; whereas in other embodiments, the composition excludes, or the method of treatment excludes administration of, methyl phenidate (see, e.g., Revuelta, et al. 'A tomoxetine for the treatment of non-levodopa responsive freezing of gait_ MDS 18$^{th}$ International Congress of Parkinson's Disease and Movement Disorders, Stockholm, Sweden Jun. 8-12, 2014; vol. 29, Abstract Supplement). In some embodiments, a pharmaceutical composition, or method of treatment of the invention, further comprises one or more additional opioid agonists, such as tramadol and/or morphine; in other embodiments, the composition or method excludes tramadol, morphine, and/or other opioid agonist (see, e.g., Samadi et al. 'The opioid agonist morphine decreases the dyskinetic response to dopaminergic agents in parkinsonian monkeys_ Neurobiol Dis. 2004, 16(1):246-253).

Effective Amounts of Tapentadol

The tapentadol-containing compositions for use in the present invention provide, or are administered so as to provide, an effective amount of tapentadol. In some embodiments, the tapentadol component is provided in amounts of about 25 mg or less, about 50 mg or less, about 75 mg or less, about 100 mg or less, e.g., in tables for oral administration, each comprising about 25 mg or less, about 50 mg or less, about 75 mg or less, about 100 mg or less, of tapentadol hydrochloride; or the tapentadol component is provided in amounts of about 25 mg or less, about 50 mg or less, about 100 mg or less, about 150 mg or less, about 200 mg or less, about 250 mg or less, e.g., in tablets for extended release, each comprising about 25 mg or less, about 50 mg or less, about 100 mg or less, about 150 mg or less, about 200 mg or less, about 250 mg or less. In some preferred embodiments, the tapentadol component is provided in a solution for oral administration. The tablets may be administered once per day, twice per day, three times per day or, preferably, 4 to 6 times per day.

In some embodiments, the tapentadol component is provided in amounts of about 0.9 mg/kg/day or less, more preferably about 2.8 mg/kg/day or less, or about 5 mg/kg/day, or about 10 mg/kg/day, or about 12 mg/kg/day or about 15 mg/kg/day. For example, amounts of about 1.5, 1.3, 1, 0.9, 0.8, 0.5, or 0.4 mg/kg/day may be administered, more preferably amounts of about 3, 2.9, 2.8, 2.7, 2.5, or 2 mg/kg/day, or anywhere within a range of 0.5 mg/kg/day to 3.0 mg/kg/day, within a range of about 1 mg/kg/day to about 10 mg/kg/day, or a range of about 3 mg/kg/day to 12 mg/kg/day. In some embodiments, tapentadol-containing pharmaceutical compositions provide the daily dose per formulation, e.g., per capsule or tablet, including any of the daily doses listed above, estimating average body weight of the intended patient population. Such doses again represent the same or similar doses compared to those currently in use, or approved for use, e.g., compared to the lowest dose currently on the market, or approved for use; or represent lower doses than those currently in use, or approved for use, e.g., representing about ½0, ¹⁄15, ¹⁄10, ⅛, ⅕, ¼, ⅓, or ½ the lowest dose currently on the market or the highest dose currently on the market. In preferred embodiments, the effective dose of tapentadol is about the same as the lowest dose currently on the market.

In more preferred embodiments, the tapentadol component is provided in amounts of about 75 mg or more, about 100 mg or more, about 110 mg or more, about 125 mg or more, about 135 mg or more, about 150 mg or more, about 175 mg or more, or about 200 mg or more, e.g., in tablets for oral administration, each comprising about 75 mg or more, about 100 mg or more, about 110 mg or more, about 125 mg or more, about 135 mg or more, about 150 mg or more, about 175 mg or more, or about 200 mg or more, of tapentadol hydrochloride, more preferably in immediate release formulations. Such doses represent the same or more than the lowest tapentadol doses currently in use (e.g., the lowest dose used is 50 mg, whereas 700 mg/day is the highest approved dose).

In some embodiments, the tapentadol component is provided as the sole active agent. In some embodiments, the tapentodol component is provided in combination with L-Dopa, e.g., with an amount of L-Dopa typical as a standard L-Dopa dose at either the initial or advanced stages of PD.

In some embodiments, the tapentadol component is provided in amounts producing an effective dose of about 126 mg/day or more, 150 mg/day, 200 mg/day or 250 mg/day. For example, amounts to provide an effective dose of about 100, about 115, about 120, about 125, about 130, about 140, about 150, about 175, about 200, about 225 or about 250 mg/day may be administered.

In some embodiments, tapentadol-containing pharmaceutical compositions provide the daily dose per formulation, e.g., per capsule or tablet, including any of the daily doses listed above, estimating average body weight of the intended patient population. In some embodiments, tapentadol-containing pharmaceutical compositions provide a dose per formulation suitable for co-administration with L-Dopa or other PD medication, e.g., per capsule or tablet, such that a patient may take each formulation together with his/her L-Dopa dose or the dose of another PD medication. For example, patients in advanced stages of PD may take levodopa 2, 3, or 4 times/day and a tapentadol-containing pharmaceutical composition for use in the present invention may provide one-half, one-third, or one-quarter the daily tapentadol dose per formulation, e.g., per capsule or tablet, or per powder packet or container of solution, for administration twice, 3 times, or 4 times a day, preferably at around the same time the patient takes his/her L-Dopa dose.

Tapentadol doses may represent the same or similar doses compared to those currently in use, or approved for use, e.g., compared to the lowest dose currently on the market, or approved for use; or represent higher doses than those currently in use, or approved for use, e.g., representing about 1.1 times, 1.5 times, 2 times, 2.2 times, 2.5 times, 2.8 times, or 3 times the lowest dose currently on the market; or about 1.1 times, 1.5 times, 2 times, 2.2 times, 2.5 times, 2.8 times, or 3 times the highest dose currently on the market. In preferred embodiments, the effective dose of the tapentadol component is about 2.5 times the lowest dose currently on the market.

Other effective doses of tapentadol can be determined in view of the instant disclosures. Considering toxicity, tapentadol shows the following LD50 values upon oral administration: rabbit ~3,200 mg/kg; mouse ~300 mg/kg; rat ~980 mg/kg; where solubility is $7.80 \times 10e-01$ g/L (see, e.g., http://www.drugbank.ca/drugs/DB06204; Drug Bank, tapentadol drug entry created on Mar. 19, 2008 10:17; updated on May 22, 2016 02:34). It is to be noted that tapentadol crosses the blood-brain barrier, such that the concentration of tapentadol inside the blood-brain barrier directly reflects its blood concentration (see, e.g., http://www.hc-sc.gc.ca/dhp-mps/prodpharma/sbd-smd/drug-med/sbd_smd_2011_nucynta_cr_133167-eng.php (Summary basis of Decision (SBD) for NNUCY NTAù CR, Health Canada, Date Modified: Apr. 26, 2011)). Tapentadol also crosses the placenta-blood barrier, but to a lesser extent.

Considering toxicity, with intravenous (IV) administration, the lethal dose for 50% of the population (LD50) was 45 mg/kg in rats and 47 mg/kg in mice. Causes of death were respiratory depression and convulsions. Repeat-dose toxicity results have showed that chronic toxic effects of tapentadol are consistent with exaggerated pharmacological effects on the central nervous system. Hepatic hypertrophy, both macroscopic and microscopic, was present in all animal species that received chronic tapentadol dosing. The enlargement of the liver was probably an adaptive response to the consistent high metabolic load of tapentadol. There was also an increased activity of the hepatic metabolic enzymes studied. In a 52-week dog study with oral dosing, exaggerated pharmacological effects of tapentadol were observed at 30 mg/kg. Convulsions were observed at tapentadol dose ranges slightly higher than human therapeutic doses in rats. Tapentadol is suspected of a proconvulsion effect at 6 mg/kg IV in rats. QT prolongation was observed at 80 and 120 mg/kg dose groups in dogs. This effect was observed to diminish or dissipate overtime.

Considering the concentration-efficacy relationship of tapentadol, the minimum effective plasma concentration of tapentadol for analgesia varies widely among patients, especially among patients who have been previously treated with agonist opioids. Considering the concentration-adverse experience relationship, there is a general relationship between increasing opioid plasma concentration and increasing frequency of adverse experiences such as nausea, vomiting, CNS effects, and respiratory depression (see, e.g., Highlights of Prescribing Information for NUCY NTA÷, Reference ID: 3400040, Janssen Pharmaceuticals, Inc. 2009, revised 2013)).

ADME ('absorption, distribution, metabolism, and excretion_, describing the disposition of a pharmaceutical compound within an organism) also is to be considered in formulating suitable effective doses and dosage regimens using tapentadol. For example, effective doses are determined, in view of the present disclosures and knowledge in the art regarding tapentadol pharmacokinetics (see, e.g., Summary basis of Decision (SBD) for NNUCY NTAù CR, Health Canada, Date Modified: Apr. 26, 2011)).

Considering absorption, following oral administration, tapentadol appeared to be completely absorbed in all animal models studied (dog, mice, and rats); however, bioavailability was low in dogs and rats due to highly efficient hepatic clearance. Further considering absorption (see, e.g., Highlights of Prescribing Information for NUCY NTA+, Reference ID: 3400040, Janssen Pharmaceuticals, Inc. 2009, revised 2013) and http://www.drugbank.ca/drugs/DB06204 (Drug Bank, Tapentadol drug entry created on Mar. 19, 2008 10:17; updated on May 21, 2016 02:34)), the mean absolute bioavailability after single-dose administration (fasting) is approximately 32% due to extensive first-pass metabolism. Maximum serum concentrations of tapentadol are typically observed at around 1.25 hours after dosing. Dose-proportional increases in the Cmax and AUC values of tapentadol have been observed over the 50 to 150 mg dose range. A multiple (every 6 hour) dose study with doses ranging from 75 to 175 mg tapentadol showed a mean accumulation factor of 1.6 for the parent drug and 1.8 for the major metabolite tapentadol-O-glucuronide, which are primarily determined by the dosing interval and apparent half-life of tapentadol and its metabolite. Considering bioavailability, immediate release (IR), 86 mg: 32%; bioavailability, extended release (ER), 86 mg: 32%; Cmax, IR: 64.2 ng/mL; Cmax, ER: 22.5 ng/mL; $T_{max}$, IR: 1.5 hours; $T_{max}$, ER: 5.0 hours. Tapentadol accumulates following multiple repeat doses. Regarding food effect, the AUC and Cmax increased by 25% and 16%, respectively, when tapentadol was administered after a high-fat, high-calorie breakfast and thus may be given with or without food.

Considering distribution, in rats, tapentadol was widely distributed. Following intravenous administration, the volume of distribution (Vz) for tapentadol is 540+/−98 L. The plasma protein binding is low and amounts to approximately 20%. Tapentadol crossed the blood-brain barrier, and crossed the placenta-blood barrier to a lesser amount. The concentration of tapentadol inside the blood-brain barrier directly reflected its blood concentration. Its main metabolite, tapentadol-O-glucuronide, had lower permeability through the blood brain barrier but it did accumulate, suggesting a slower transfer mechanism. Plasma protein binding was low at 15-20% in all species tested including humans. Tapentadol had a higher binding to sepia melanin at 25-50%.

Considering metabolism, tapentadol was extensively metabolized to tapentadol-O-glucuronide via the uridine 5'-diphospho-glucuronosyltransferase (UDP-UGT) systems. The UGT isoenzymes conjugate the parent drug and also many of the non-glucuronidation intermediate metabolites. Oxidation was a minor metabolic pathway. Studies on inhibition and induction of hepatic microsomal drug metabolizing enzymes showed that tapentadol has no effect on the cytochrome P450 (CY P) isoenzymes.

Further considering metabolism and elimination, in humans, about 97% of the parent compound for tapentadol is metabolized. Tapentadol mainly is metabolized via Phase 2 pathways, and only a small amount is metabolized by Phase 1 oxidative pathways. The major pathway of tapentadol metabolism is conjugation with glucuronic acid to produce glucuronides. After oral administration approximately 70% (55% O-glucuronide and 15% sulfate of tapentadol) of the dose is excreted in urine in the conjugated form. A total of 3% of drug was excreted in urine as unchanged drug. Tapentadol is additionally metabolized to N-desmethyl tapentadol (13%) by CY P2C9 and CY P2C19 and to hydroxy tapentadol (2%) by CY P2D6, which are further metabolized by conjugation. Therefore, drug metabolism mediated by cytochrome P450 system is of less importance than phase 2 conjugation. None of the metabolites contribute to the analgesic activity (all metabolites appear to be inactive).

Considering excretion, the conjugated tapentadol was predominantly eliminated via the urine and to a much lesser extent in the feces. Further considering elimination, tapentadol and its metabolites are excreted almost exclusively (99%) via the kidneys. Approximately 70% (55% O-glucuronide and 15% sulfate of tapentadol) is excreted in conjugated form. A total of 3% of drug was excreted in urine as unchanged drug. The elimination half-life is on average 4 hours after oral administration. T he total clearance is 1530+/−177 mL/min.

Regarding ADME and geriatric patients, the mean exposure (AUC) to tapentadol was similar in elderly subjects compared to young adults, with a 16% lower mean Cmax observed in the elderly subject group compared to young adult subjects. For patients with renal impairment, AUC and Cmax of tapentadol were comparable in subjects with varying degrees of renal function (from normal to severely impaired). In contrast, increasing exposure (AUC) to tapentadol-O-glucuronide was observed with increasing degree of renal impairment. In subjects with mild (CLCR=50 to <80 mL/min), moderate (CLCR=30 to <50 mL/min), and severe (CLCR=<30 mL/min) renal impairment, the AUC of tapentadol-O-glucuronide was 1.5-, 2.5-, and 5.5-fold higher compared with normal renal function, respectively.

For patients with hepatic impairment, administration of tapentadol may result in higher exposures and serum levels compared to subjects with normal hepatic function. The ratio of tapentadol pharmacokinetic parameters for the mild hepatic impairment group (Child-Pugh Score 5 to 6) and moderate hepatic impairment group (Child-Pugh Score 7 to 9) in comparison to the normal hepatic function group were 1.7 and 4.2, respectively, for AUC; 1.4 and 2.5, respectively, for Cmax; and 1.2 and 1.4, respectively, for t1/2. The rate of formation of tapentadol-O-glucuronide was lower in subjects with increased liver impairment.

In determining effective doses, clinical studies regarding tapentadol pharmacokinetics also are considered. Regarding absorption, maximum serum concentrations (Cmax) of tapentadol were observed 3-6 hours after administration of tapentadol CR. Dose proportional increases in drug exposure [area under the curve (AUC) values] were observed following administration of controlled release tapentadol (tapentadol CR_) as single doses over a range of 50-250 mg. A single-dose, crossover comparative bioavailability study evaluated the effect of food on the tapentadol CR 250 mg tablet in healthy subjects. Data provided indicate a lack of significant effect of food on the bioavailability of a 250 mg tablet.

With respect to distribution, the volume of distribution results (540 ě98 L) show that tapentadol was widely distributed throughout the body. The plasma protein binding for tapentadol was low at approximately 20%. With respect to metabolism, tapentadol was extensively metabolized in the liver. The major metabolic pathway was glucuronidation with tapentadol-O-glucuronide as the main conjugate. Tapentadol demonstrated no inhibitory activity on the CYP isoenzymes relevant in clinical pharmaceutically metabolism. Tapentadol showed no significant induction of CYP isoenzymes.

With respect to excretion, tapentadol and its metabolites were predominantly excreted via the kidneys. In four healthy men administered a single oral dose of 100 mg radiolabelled tapentadol, the Cmax was at 1.25-1.5 hours; the ratio of conjugated tapentadol/unconjugated tapentadol was 24:1; the exposure to the conjugates was approximately 64% of the total; 95% of the total dose was excreted within 24 hours, 99% via urine. Of the related compounds excreted in the urine, 3% was the parent drug, 69% was in the conjugated form, and 27% were other forms of metabolites. Approximately 1% of the total drug was excreted in the feces. On average, 99.9% of the drug was recovered in 5 days. Intra-individual variability may be corrected for by using dose-titrations to determine other effective amounts of tapentadol for use in the methods of the present invention.

Stavudine-Containing Pharmaceutical Compositions

Stavudine-containing pharmaceutical compositions for use in the present invention include stavudine as the active agent for use in Parkinson˜s disease, a related disorder, or a condition associated with a symptom thereof. The term 'stavudine_ as used herein relates to the compound with brand names 'Actastav (Actavis)_ (Ai Fu Ding, Wujing Medicine); 'Avostav_ (Ranbaxy Laboratories); 'Estavudox_ (Biotoscana); 'Exvihr_ (Biogen); 'Flamistav_ (Flamingo Pharmaceuticals); 'Landstav_ (Landsteiner); 'Lion_ (Filaxis); 'Mai Si Ting_ (Meijisi Pharmaceutical); 'S.T.V._ (Ivax); 'Sazi_ (NEGPF); 'Stadine_ (Stadine); 'Stag_ (Hetero); 'Stamar_ (LKM); 'Stavex_ (Aurobindo); 'Stavir_ (Cipla); 'Stavubergen_ (Paylos); or 'Zerit_ (Bristol-Myers Squibb). Stavudine also has been identified by the number '3056-17-5_. Information regarding this therapeutic can be found, for example, through the FDA, and http://www-.lookchem.com/newsell/search.aspx?key=Stavudine&classid=49&p=1 (Look Chem, Stavudine Organic Chemicals); the EMP; or from the drug bank listing (http://www.drugbank.ca/drugs/DB00649 (Drug Bank, stavudine drug entry created on Jun. 13, 2005 07:24; updated May 23, 2016 03:36).

Stavudine is represented by the structure below, Formula II:

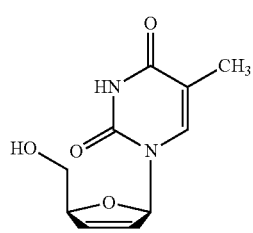

Formula II

The invention also contemplates other forms of stavudine for use in the invention, including isomers, other salts, and other derivatives thereof, preferably where the derivative maintains therapeutic or prophylactic activity with respect to Parkinson˜s disease, a related disorder, or a symptom thereof.

Stavudine is classified as an antiviral, specifically, an antiviral for use in combination with other antiviral medicines to treat adults and children who are infected with human immunodeficiency virus (HIV). Stavudine has been described as inhibiting the activity of HIV-1 reverse transcriptase (RT) both by competing with the natural substrate dGTP and by its incorporation into viral DNA. Accordingly, stavudine has been classified as a nucleoside reverse-transcriptase inhibitor (NRTI), that blocks the activity of reverse transcriptase, an enzyme produced by HIV to allow the virus to infect cells in the body and replicate. By blocking this enzyme, stavudine, e.g., in combination with other antiviral medicines, reduces the amount of HIV in the blood and keeps it at a low level. See, e.g., European Medicines Agency, Science Medicines Health, Zerit (stavudine) last updated on Feb. 11, 2016.

Effective Amounts of Stavudine

The stavudine-containing compositions for use in the present invention provide, or are administered so as to provide, an effective amount of stavudine. In some embodiments, pharmaceutical compositions for use in the invention comprising stavudine are formulated into an oral solution, particularly for administration to children. In preferred embodiments, the oral solution is administered in doses of about 1 mg/mL or less of stavudine. In some embodiments, pharmaceutical compositions comprising stavudine are formulated into a powder for use in preparing an oral solution. In preferred embodiments, packets of about 200 mg powder or less may be used. In some embodiments, pharmaceutical compositions comprising stavudine are formulated into capsules for extended release.

In some embodiments, pharmaceutical compositions comprising stavudine are formulated into capsules for oral administration. In preferred embodiments, the capsules comprise about 15 mg or less, about 20 mg or less, about 30 mg or less, or about 40 mg stavudine or less. Such doses represent less than amounts currently in use, or approved for use, on the market. See, e.g., http://www.drugs.com/pro/stavudine-oral-solution.html (Stavudine Oral Solution, Drugs.com. 2016). By comparison, in adults, a dose of 30 mg every 12 hours is recommended for patients weighing less than 60 kg; and a dose of 40 mg every 12 hours is recommended for patients weighing over 60 kg, as discussed in more detail below.

In some embodiments, the stavudine component is provided in amounts of about 0.9 mg/kg/day or less, more preferably 0.3 mg/kg/day or less. For example, amounts of about 1.5, 1.3, 1, 0.9, 0.8, 0.5, or 0.4 mg/kg/day be administered, more preferably amounts of about 0.5, 0.4, 0.3, or 0.2 mg/kg/day. In some embodiments, stavudine-containing pharmaceutical compositions provide the daily dose per formulation, e.g., per capsule or tablet, or per powder packet or container of solution, including any of the daily doses listed above, estimating average body weight of the intended patient population. Such doses again represent the same or similar doses compared to those currently in use, or approved for use, e.g., compared to the lowest dose currently on the market, or approved for use; or represent lower doses than those currently in use, or approved for use, e.g., representing about 1/20, 1/15, 1/10, 1/8, 1/5, 1/4, 1/3, or 1/2 the lowest dose currently on the market. In preferred embodiments, the effective dose of stavudine is about the same as the lowest dose currently on the market.

Other suitable effective doses and dosage regimens can be selected by one skilled in the art, considering the present disclosures as well as characteristics of stavudine. Regarding its permeability and solubility, certain forms of stavudine have been classified as Class III biopharmaceuticals, having low permeability and high solubility; while its absorption is limited by the permeation rate, the drug is solvated very fast.

Other forms of stavudine have been classified as Class I biopharmaceuticals, having high permeability and high solubility. These compounds are well absorbed and their absorption rate is usually higher than excretion (see, e.g., WHO Prequalification of Medicines Programme, 'General notes on Biopharmaceuticals Classification System (BCS)-based biowaiver applications_ Guidance Document, October 2012).

Regarding posology of stavudine, the dose for use may be calculated based on the age and weight of the patient. For example, adults weighing less than 60 kg and children weighing over 30 kg may take a dose of less than about 30 mg, and adults over 60 kg may take less than about 40 mg. Children over the age of 14 days may receive 1 mg per kilogram body weight or less, unless they weigh more than 30 kg. Babies less than 13 days old may be given less than about 0.5 mg/kg body weight. In adults, recommended doses based on body weight may include less than about 40 mg, twice daily for patients $\hbar$60 kg; less than about 30 mg, twice daily for patients <60 kg. In pediatric patients, recommended doses may include for newborns, from birth to 13 days old, less than about 0.5 mg/kg/dose, e.g., every 12 hours; and for pediatric patients at least 14 days old and weighing less than 30 kg, less than about 1 mg/kg/dose, e.g., every 12 hours; pediatric patients weighing 30 kg or greater may receive a recommended adult dosage.

In some preferred dosage regimens, pharmaceutical compositions comprising stavudine are administered about every 12 hours, without regard to meals. In even more preferred embodiments, pharmaceutical compositions comprising stavudine are used for a short period of time, with a brief total course of treatment.

Toxicity also is to be considered in formulating suitable effective doses and dosage regimens using stavudine. LD50 for stavudine is as follows: for oral administration in rats⁻ 4,000 mg/kg; iv administration in rats⁻1,200 mg/kg (see, e.g., http://www.lookchem.com/newsell/search.aspx?key=Stavudine&classid=49&p=1 (Look Chem, Stavudine Organic Chemicals); rat acute toxicity⁻1,7802 LD50, mol/kg (see, e.g., http://www.drugbank.ca/drugs/DB00649 (Drug Bank, stavudine drug entry created on Jun. 13, 2005 07:24; updated May 23, 2016 03:36); IV administration in dogs⁻1,680 mg/kg; oral administration in dogs⁻ 2,000 mg/kg; iv administration in mice⁻1,000 mg/kg; and oral administration in mice⁻1,000 mg/kg.

ADME also is to be considered in formulating suitable effective doses and dosage regimens using stavudine. Peak plasma concentrations (Cmax) and area under the plasma concentration-time curve (AUC) increased in proportion to dose after both single and multiple doses ranging from 0.03 to 4 mg/kg. Nonetheless, there is no significant accumulation of stavudine with repeated administration every 6, 8, or 12 hours. Considering absorption, oral bioavailability (%) is 86.4 ě 18.2 and human intestinal absorption (p=0.9889). Following oral administration, stavudine is rapidly absorbed, with peak plasma concentrations occurring within 1 hour after dosing. The systemic exposure to stavudine is the same following administration as capsules or solution. Steady-state pharmacokinetic parameters of stavudine, e.g., in HIV-infected adults (ZERIT 40 mg BID Mean ě SD (n=8)) include: AUC (ngǒh/mL) (from 0 to 24 hours) of 2568 ě 454; Cmax (ng/mL) of 536 ě 146; and Cmin (ng/mL) of 8 ě 9.

Considering distribution, volume of distribution (L) following 1-hour IV infusion of stavudine is 46 ě 21; protein binding is negligible; half-life is 0.8-1.5 hours (in adults); and there is crossing of the blood brain barrier (probability=0.9381). Binding of stavudine to serum proteins was negligible over the concentration range of 0.01 to 11.4 I g/mL; and stavudine distributes equally between red blood cells and plasma. Because stavudine is not protein-bound, it is not expected to affect the pharmacokinetics of protein-bound drugs.

Considering metabolism, stavudine is not considered to inhibit major cytochrome P450 isoforms CY P1A2, CY P2C9, CY P2C19, CY P2D6, and CY P3A4, making it is unlikely that clinically significant drug interactions will occur with drugs metabolized through these pathways. Stavudine is phosphorylated intracellularly to stavudine triphosphate, the active substrate for HIV-reverse transcriptase (i.e. prodrug). Further, CY P450 inhibitory: low (p=0.9445).

Regarding hERG inhibition (predictor I), stavudine is a weak inhibitor (p=0.9413). Regarding hERG inhibition (predictor II), stavudine is a non-inhibitor (p=0.9375). hERG (the human Ether-⁻-go-go-Related Gene) is a gene (also known as KCNH2) that codes for a protein known as Kv11.1, the alpha subunit of a potassium ion channel. This ion channel (sometimes simply denoted as 'hERG_) is best known for its contribution to the electrical activity of the heart that coordinates the heart˜s beating (i.e., the hERG channel mediates the repolarizing IKr current in the cardiac action potential). When this channel˜s ability to conduct electrical current across the cell membrane is inhibited or compromised, either by application of drugs or by rare mutations in some families, it can result in a potentially fatal disorder called long QT syndrome; a number of clinically successful drugs in the market have had the tendency to inhibit hERG, and create a concomitant risk of sudden death, as a side-effect, which has made hERG inhibition an important antitarget to be avoided during drug development. See, e.g., Hedley et Al. (2009) 'The genetic basis of long QT and short QT syndromes: a mutation update_ Hum Mutat. 30(11):1486⁻1511.

Considering elimination, in humans, renal elimination accounts for about 40% of the overall clearance regardless of the route of administration. The mean renal clearance was about twice the average endogenous creatinine clearance, indicating active tubular secretion in addition to glomerular filtration. The remaining 60% of the drug is presumably eliminated by endogenous pathways. Healthy subjects receiving 80 mg PO show renal clearance of 272 mL/min. HIV-infected adult and pediatric patients show 594+/−164 mL/min following 1-hour IV infusion. HIV-exposed or -infected pediatric patients (5 weeks˜15 years) show 0.75+/−3.76 mL/min/kg following 1-hour IV infusion. In general, total body clearance (mL/min) following 1-hour IV infusion equals 594 ě 164; apparent oral clearance (mL/min) following single oral dose equals 560 ě 182c (assuming a body weight of 70 kg); renal clearance (mL/min) following 1-hour IV infusion equals 237 ě 98; elimination half-life, IV dose (h) following 1-hour IV infusion equals 1.15 ě 0.35; elimination half-life, oral dose (h) following single oral dose equals 1.6 ě 0.23; and urinary recovery of stavudine (% of dose) following 1-hour IV infusion and over 12-24 hours equals 42 ě 14. See, e.g., http://www.druglib.com/druginfo/zerit/description_pharmacology/(Drug Information Portal, Zerit (Stavudine)—Description and Clinical Pharmacology, DrugLib.com, 2006-2015), regarding pediatric pharmacokinetic parameters, pharmacokinetics in renal impairment, and pharmacokinetics in hepatic impairment.

Considering drug interactions, zidovudine competitively inhibits the intracellular phosphorylation of stavudine. Similar considerations may be made for doxorubicin and ribavirin.

Nabumetone-Containing Pharmaceutical Compositions

Nabumetone-containing pharmaceutical compositions for use in the present invention include nabumetone as the active agent for use in Parkinson's disease, a related disorder, or a condition associated with a symptom thereof. The term 'nabumetone_ as used herein relates to the compound with brand names 'Relafen_, Relifex_, and 'Gambaran._ Information regarding this therapeutic can be found, for example, through the FDA.

In some embodiments, nabumetone is represented by the structure below, Formula III:

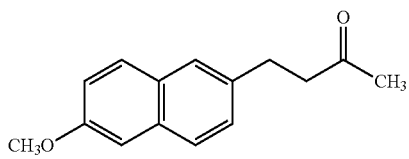

Formula III

The invention also contemplates other forms of nabumetone for use in the invention, including isomers, other salts, and other derivatives thereof, preferably where the derivative maintains therapeutic or prophylactic activity with respect to Parkinson's disease, a related disorder, or a symptom thereof.

The compound is classified as a nonsteroidal anti-inflammatory drug (NSAID) and is used for acute and chronic symptoms of osteoarthritis and rheumatoid arthritis. Nabumetone has been described as a poor COX-2 inhibitor. The parent compound is a prodrug, which undergoes hepatic biotransformation to the active component, 6-methoxy-2-naphthylacetic acid (6MNA), that is a potent inhibitor of prostaglandin synthesis, most likely through binding to the COX-2 and COX-1 receptors. See, e.g., S®nchez-Pernaute, et al. 'Selective COX-2 inhibition prevents progressive dopamine neuron degeneration in a rat model of Parkinson's disease_, 2004, Journal of Neuroinflanimtion 1:6 and Teismann et al. 'COX-2 and neurodegeneration in Parkinson's disease_, 2003, Ann NY Acad Sci. 991:272-277. It also is characterized as a Class II biopharmaceutical.

In some embodiments, pharmaceutical compositions for use in the invention comprising nabumetone do not include one or more to the active agents described in WO 2009/147681 A1 (Pharma Two B Ltd) to Lamensdorf et al.

Effective Amounts of Nabumetone

The nabumetone-containing compositions for use in the present invention provide, or are administered so as to provide, an effective amount of nabumetone. In some embodiments, pharmaceutical compositions comprising nabumetone are formulated as tablets, e.g., tablets for oral administration. In preferred embodiments, the tablets comprise about 500 mg or less, about 600 mg or less, about 700 mg or less, or about 750 mg or less of nabumetone. In some embodiments, the compositions are administered to provide an initial dose of about 1,000 mg or less, preferably orally at bedtime. In some embodiments, the compositions are administered to provide an ongoing dose of about 1,500-2,000 mg or less, preferably orally, in one or two divided doses per day. Such doses represent less than those in use, or approved for use, on the market.

Other suitable effective doses and dosage regimens can be selected by one skilled in the art, considering the present disclosures as well as characteristics of nabumetone. Considering blood brain barrier permeability, nabumetone is permeable.

Regarding pharmacokinetics, steady state plasma concentrations in elderly patients were generally higher than in young healthy subjects and nabumetone is well absorbed from the gastrointestinal tract. It undergoes rapid biotransformation to the principal active metabolite, 6-methoxy-2-naphthylacetic acid (6MNA). Approximately 35% of a 1,000 mg oral dose of nabumetone is converted to 6MNA and 50% is converted into unidentified metabolites which are subsequently excreted in the urine. 6MNA is more than 99% bound to plasma proteins. It is 0.2-0.3% at concentrations typically achieved following administration of 1,000 mg of nabumetone. Following oral administration of dosages of 1,000-2,000 mg to steady state, the mean plasma clearance of 6MNA is 20-30 mL/min and the elimination half-life is approximately 24 hours.

4. Combination Pharmaceutical Compositions

Another aspect of the invention provides pharmaceutical compositions comprising, as well as methods of treatment comprising administering, more than one active agent. In particular embodiments, the invention relates to pharmaceutical compositions comprising both tapentadol, or a pharmaceutically effective salt or derivative thereof, in combination with an agent known to treat Parkinson's disease or a related disorder, and a derivative of an agent known to treat Parkinson's disease or a related disorder. Agents known to treat Parkinson's disease or a related disorder include dopaminergic agents, such as dopamine agonists and levodopa. In particularly preferred embodiments, the pharmaceutical compositions of the invention comprise both a tapentadol component and a dopaminergic agent, such as L-Dopa.

In some embodiments, the pharmaceutical composition comprises tapentadol hydrochloride as the tapentadol component. In preferred embodiments, the tapentadol (e.g., tapentadol hydrochloride) is provided in amounts the same as, similar to, or greater than those found in tapentadol capsules currently available. In more preferred embodiments, the tapentadol is present in an amount greater than the lowest dose of tapentadol currently on the market, e.g., 1.5, 2, 2.5, or 3 times the lowest dose on the market, more preferably 2.5 times the lowest dose. The lowest tapentadol dose in the US, e.g., is 50 mg. Appropriate doses are formulated in combination with an agent known to treat Parkinson's disease or a related disorder, including dopaminergic agents, such as levodopa.

Levodopa is used interchangeably herein with the terms 'L-DOPA_, 'L-Dopa_ and the like, and refers to a precursor of dopamine. This precursor is able to cross the blood-brain barrier, while dopamine itself cannot. In the central nervous system, levodopa is metabolized to dopamine by aromatic L-amino acid decarboxylase, thereby increasing dopamine levels in the brain. In some embodiments, pharmaceutical compositions comprising L-Dopa further comprise a peripheral decarboxylase inhibitor, such as carbidopa or benserazide, and/or a catechol-O-methyl transferase (COMT) inhibitor, such as tolcapone or entacapone, to prevent synthesis of dopamine in peripheral tissue. Levodopa typically is formulated in combination with carbidopa and entacapone. In preferred embodiments, L-Dopa is administered in combination with tapentadol, with or without carbidopa and/or with or without entacapone.

Levodopa currently is used for relieving symptoms of PD, helping to reduce tremor, stiffness, and slowness, and helping to improve muscle control, balance, and walking. Levodopa does not, however, affect freezing, dementia, or problems with involuntary functions, such as constipation, urinary problems, impotence, or pain. Levodopa also does not slow the disease process, but it improves muscle movement and delays severe disability and may be used at all stages of the disease. Nonetheless, the majority of people taking levodopa develop complications caused by long-term levodopa therapy within 5-10 years. Movement problems called dyskinesias are the most common and troublesome complication.

Moreover, after chronic L-Dopa therapy, such as in patients with advanced PD or related disorder, L-Dopa wears off and motor symptoms become unpredictable. Early on in PD, L-Dopa typically is effective, with substantially even results from one dose to the next. Nonetheless, it is fairly common for the effects to gradually weaken, e.g., from about 2 to about 5 years after starting L-Dopa therapy, and sometimes sooner. Almost 50% of PD patients develop symptoms of wearing-off within a few years and almost 90% develop them after 15 years of starting L-Dopa treatment. The symptoms of wearing-off can be treated with products containing active pharmaceutical ingredients that lengthen the effects of levodopa or by supplementing the levodopa with other forms of treatment.

Other agents known to treat Parkinson's disease or a related disorder include, for example, dopamine agonists, such as pramipexole (Mirapex), ropinirole (Requip), rotigotine (given as a patch, Neupro), and apomorphine (Apokyn). Further agents known to treat Parkinson's disease or a related disorder include, for example, monoamine oxidase B (MAO-B) inhibitors, such as selegiline (Eldepryl, Zelapar) and rasagiline (Azilect); catechol O-methyltransferase (COMT) inhibitors, such as Entacapone (Comtan) and tolcapone (Tasmar); anticholinergic medications, such as benztropine (Cogentin) or tri hexyphenidyl; and amantadine.

Rasagiline (Azilect, AGN 1135) is an irreversible inhibitor of monoamine oxidase used as a monotherapy in early PD or as an adjunct therapy in more advanced cases. Recently, the FDA has expanded the indication for AZILECT÷ (rasagiline tablets) from monotherapy and adjunct to levodopa (LD) to now include adjunct to dopamine agonists (DAs). Oral bioavailability of rasagiline is 35%, reaching T(max) after 0.5˜1.0 hours and having a half-life of 1.5-3.5 hours. Rasagiline undergoes extensive hepatic metabolism primarily by cytochrome P450 type 1A2 (CY P1A2). Rasagiline is initiated at 1-mg once-daily dose as monotherapy in early PD patients and at 0.5˜1.0 mg once-daily as adjunctive to levodopa in advanced PD patients.

In addition to or instead of rasagiline, any agent used in neuroprotective therapy may be used in combination with the pharmaceutical compositions of the present invention. A neuroprotective therapy, also called disease-modifying therapy, aims to slow, block, or reverse disease progression and can be defined as those that slow underlying loss of dopamine neurons. This protection can occur before any symptoms manifest based on genetic risk, and also during early- or late-stage PD when other treatments have ceased their impact due to the progression of the disease. Accordingly, neuroprotective therapy seeks to delay the introduction of levodopa or decrease its dosage in order to delay undesirable motor symptoms like dyskinesias. Currently, no proven neuroprotective agents or treatments are available for PD. One of the agents currently under investigation is isradipine.

Isradipine (DynaCirc÷ CR) is one in a class of medications called calcium channel blockers that is already used to treat high blood pressure. As of October 2014, it is in Phase III of CT as a neuroprotective candidate (http://clinicaltrials.gov/show/NCT02168842).

In some embodiments, pharmaceutical compositions of the invention comprise stavudine and/or nabumetone in combination with levodopa, or in combination with levodopa as well as with tapentadol. In some embodiments, the composition comprises tapentadol hydrochloride in an amount the same as or similar to the lowest dose of tapentadol currently on the market, in combination with stavudine in an amount the same as or similar to the lowest dose of stavudine currently on the market, preferably further in combination with levodopa.

Effective Amounts in Combination Pharmaceutical Compositions

The instant invention provides, in some embodiments, combination therapies in therapeutic and/or prophylactic indications for Parkinson's disease, a related disorder, condition associated with gait problems, or other condition treated with a dopaminergic agent, e.g., to ameliorate a side effect of chronic treatment of the underlying disease or disorder with a domaminergic agent. The pharmaceutical compositions for use in the invention may comprise more than one active agent indicated to such diseases, disorders, or conditions. In some embodiments, one or more of the different active agents are co-administered in the same or separate formulations, where the active agents are in effective amounts. There is accumulating evidence that therapeutic agents simultaneously directed to more than one target provide improved or, in some instances, synergistic benefits compared with use of a therapeutic agent directed to only one target or even compared with use of a combination of different therapeutic agents, each directed to a single target, for example, improved efficacy, including with chronic or long term use, reduced side effects, reduction in the amount of the effective dose, or other unpredictable benefits.

In some embodiments, tapentadol is one of a combination of active agents provided in a therapeutically or prophylactically effective amount. In some preferred embodiments, the tapentadol component is provided in amounts of about 126 mg/day or greater in combination with another active agent known to treat Parkinson's disease or a related disorder, or a derivative of an agent known to treat Parkinson's disease or a related disorder, e.g. a dopaminergic agent, such as levodopa. For example, amounts of about 75 mg, about 100 mg, about 110 mg, about 125 mg, about 135 mg, about 150 mg, about 175 mg, or about 200 mg of tapentadol, one, two, three, four, five, or six times per day, may be administered in combination with another active agent, such as a dopaminergic agent for treating Parkinson's disease or related disorder, preferably levodopa. The tapentadol component preferably is tapentadol hydrochloride and/or the pharmaceutical composition preferably is an immediate release formulation.

In other embodiments, the above amounts of tapentadol may be provided as the sole active agent in a given pharmaceutical composition.

In some embodiments, the above amounts of tapentadol are provided in combination with a dopaminergic agent, such as levodopa. Levodopa typically is formulated in combination with carbidopa and entacapone. In preferred embodiments, L-Dopa is administered in combination with tapentadol, with or without carbidopa and/or with or without entacapone. In some embodiments, the levodopa component is provided in amounts typically prescribed for treating Parkinson's disease, preferably amounts typically prescribed during advanced stages of the disease, in combination with a tapentadol component.

For example, during initial stages of PD, levodopa amounts of about 300, 400, 500, 600, 700, 800, 900, or 1,000 mg/day may be administered, preferably divided in half and administered twice a day, more preferably in combination with tapentadol. During advanced PD, amounts of levodopa of about 2,000, 3,000, 4,000, 5,000, 6,000, or 7,000 mg/day may be administered, preferably divided in three or more doses and administered three or more times day, more preferably in combination with tapentadol. In some embodiments, (tapentadol plus levodopa)-containing pharmaceutical compositions provide the daily dose per formulation, e.g., per capsule or tablet, or per powder packet or container of solution, including any of the daily doses for tapentadol and levodopa, listed above, in combination, estimating average body weight of the intended patient population. In some embodiments, (tapentadol plus levodopa)-containing pharmaceutical compositions provide one-half, one-third, or one-quarter the daily dose per formulation of each of the active agents, e.g., per capsule or tablet, or per powder packet or container of solution, for administration twice, three times, or four times a day.

Alternatively, in some embodiments, the tapentadol component is provided in amounts about 25 mg or less, about 50 mg or less, about 75 mg or less, about 100 mg or less, e.g., in tablets for oral administration, each comprising about 25 mg or less, about 50 mg or less, about 75 mg or less, about 100 mg or less, of tapentadol hydrochloride; or the tapentadol component is provided in amounts about 25 mg or less, about 50 mg or less, about 100 mg or less, about 150 mg or less, about 200 mg or less, about 250 mg or less, e.g., in tablets for extended release, each comprising about 25 mg or less, about 50 mg or less, about 100 mg or less, about 150 mg or less, about 200 mg or less, about 250 mg or less. These doses are administered preferably 4 to 6 times per day, or two or three times per day. In some preferred embodiments, the tapentadol component is provided in amounts of about 20 mg/ml or less (1 to 5 ml amounts), e.g., in a solution for oral administration. Such doses represent less than those currently in use, or approved for use.

In some embodiments, stavudine is one of a combination of active agents provided in a therapeutically or prophylactically effective amount. In some embodiments, the stavudine component is provided in an amount of about 1 mg/mL or less of stavudine, e.g., in a solution, such as a solution for children. In some embodiments, the stavudine component is provided in an amount of about 200 mg powder or less, e.g., in packets for use in preparing a solution in water for oral consumption. In some embodiments, the stavudine component is provided in doses of about 15 mg or less, about 20 mg or less, about 30 mg or less, or about 40 mg stavudine or less, e.g., in capsules for oral intake. Such doses represent less than amounts currently in use, or approved for use, on the market. See, e.g., http://www.drugs.com/pro/stavudine-oral-solution.html (Stavudine Oral Solution, Drugs.com. 2016).

In some embodiments, both stavudine and tapentadol are administered in combination, either in the same or separate formulations. In some preferred embodiments, the effective dose of stavudine in combination with tapentadol, or another active, is less than that of stavudine when used as the sole active agent. Similarly, in some preferred embodiments, the effective dose of tapentadol in combination with stavudine, or another active, is less than that of tapentadol when used as the sole active agent. In some embodiments, where tapentadol and stavudine are used in combination, both show therapeutic and/or prophylactic effects at lower doses than when either is used as the sole active.

For example, in some embodiments, the tapentadol component is provided is provided in amounts of about 0.9 mg/kg/day or less, more preferably about 2.8 mg/kg/day or less, or about 5 mg/kg/day or less, or about 10 mg/kg/day or less, or about 12 mg/kg/day or less or about 15 mg/kg/day or less; for example, amounts of about 1.5, 1.3, 1, 0.9, 0.8, 0.5, or 0.4 mg/kg/day may be administered, more preferably amounts of about 3, 2.9, 2.8, 2.7, 2.5, or 2 mg/kg/day, or anywhere within a range of 0.5 mg/kg/day to 3.0 mg/kg/day, within a range of about 1 mg/kg/day to about 10 mg/kg/day, or a range of about 3 mg/kg/day to 12 mg/kg/day may be administered in combination with another active agent, e.g. stavudine. In some embodiments, the stavudine component is provided in amounts of about 0.9 mg/kg/day or less, more preferably 0.3 mg/kg/day or less in combination with another active agent, e.g. tapentadol. For example, amounts of about 1.5, 1.3, 1, 0.9, 0.8, 0.5, or 0.4 mg/kg/day may be administered, more preferably amounts of about 0.5, 0.4, 0.3, or 0.2 mg/kg/day of stavudine may be administered in combination with another active agent, e.g., tapentadol. In some embodiments, (tapentadol plus stavudine)-containing pharmaceutical compositions provide the daily dose per formulation, e.g., per capsule or tablet, or per powder packet or container of solution, including any of the daily doses for tapentadol and stavudine, listed above, in combination, estimating average body weight of the intended patient population.

In a specific embodiment, a pharmaceutical composition comprising a tapentadol component is administered without food at a dose of about 50 mg, 75 mg, or 100 mg, or less, about every 4 to 6 hours. On the first day of dosing, the second dose may be administered as soon as about one hour after the first dose. Subsequent dosing is about 50 mg or less, about 75 mg or less, or about 100 mg or less, about every 4 to 6 hours (see, e.g., Highlights of Prescribing Information for NUCY NTA÷, Reference ID: 3400040, Janssen Pharmaceuticals, Inc. 2009, revised 2013)).

The pharmaceutical compositions described herein, comprising one or more active agents, may themselves be administered alone or in combination with still other prophylactic and/or therapeutic agents. Each prophylactic or therapeutic agent may be administered at the same time, either in the same or separate formulation; or sequentially, in separate formulations, in any order at different points in time; however, if not administered at the same time, they should be administered sufficiently close in time so as to provide the desired therapeutic or prophylactic effect, including any synergistic effect. Each therapeutic agent can be administered separately, in any appropriate form and by any suitable route.

In various embodiments, the different prophylactic and/or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart, or no more than 48 hours apart. In certain embodiments, two or more agents are taken together in the same tablet, capsule, or solution by oral administration.

5. Modes of Adminsitration

Another aspect of the invention relates to delivery of pharmaceutical compositions comprising an active agent described herein. Various delivery systems are known and can be used to administer the agents described herein. Methods of administering the agents include, but are not limited to, oral administration (e.g., in capsules, tables, or solutions for consumption); parenteral administration (e.g., intradermal, intramuscular, intraperitoneal, intravenous, and subcutaneous, including infusion or bolus injection); epidural; and by absorption through epithelial or mucocutaneous or mucosal linings (e.g., intranasal, oral mucosa, rectal, and intestinal mucosa, etc.).

In certain embodiments, the agents described herein are administered orally. For example, the patient may be directed to swallow a capsule or tablet, prepare and drink a solution, or eat a food product comprising tapentadol, stavudine, nabumetone, and/or levodopa, in effective amounts disclosed herein. Where the patient is directed to ingest one or more of the compounds/compositions, such direction may comprise instructions or information that use of the compound/composition may provide a therapeutic and/or prophylactic benefit, e.g., in Parkinson˜s disease, a related disorder, a condition associated with a symptom of Parkinson˜s or a related disorder, or regarding side effects of chronic treatment of the underlying disease or disorder.

For example, such direction may be oral direction, e.g., through oral instruction from, for example, a physician, sales professional or organization, and/or radio, television, or internet media (i.e., advertisement); or written direction, e.g., through written instructions from, for example, a physician or other medical professional (e.g., who has authority to prescribe medication), or a pharmacist, sales professional or organization (e.g., through marketing brochures, pamphlets, or other instructive paraphernalia), written media (e.g., internet, electronic mail, or other computer-related media), and/or packaging associated with the pharmaceutical composition (e.g., a label present on a package containing the composition).

In certain embodiments, the agents described herein are administered intramuscularly, intravenously, or subcutaneously, and may be administered together with other biologically active agents. In a specific embodiment, the pharmaceutical composition is formulated for intravenous or intraperitoneal administration as a sterile product. Administration can be systemic or local.

Treatment of a subject with a therapeutically or prophylactically effective amount of the agents described herein can include a single treatment or can include a series of treatments. For example, pharmaceutical compositions comprising an agent described herein may be administered once a day, twice a day, or three times a day. In some embodiments, the agent may be administered once a day, every other day, once a week, twice a week, once every two weeks, once a month, once every six weeks, once every two months, twice a year, or once per year. In some preferred embodiments, a once daily dose is used and, more preferably, is continued over the course of the disease. In some preferred embodiments, a twice a day dose, three times a day dose, four times a day dose, or a more frequent daily dose, is used, more preferably during the advanced stages of PD or related disease. It will also be appreciated that the effective dosage of certain agents, e.g., the effective dosage of agents described herein may increase or decrease over the course of treatment. For example, tapentadol may first be administered during advanced PD, or may be administered in higher or in increasingly higher amounts, during advanced PD, e.g., when the effects of other treatments begin to wear off and/or when side effects of standard treatments become problematic, such as when OFF periods appear or increase in duration.

In some embodiments, ongoing treatment is indicated, e.g., on a long-term basis, such as in the ongoing treatment and/or management of chronic diseases or disorders like Parkinson˜s. For example, in particular embodiments, an agent described herein is administered over a period of time, e.g., for at least 6 months, at least one year, at least two years, at least five years, at least ten years, at least fifteen years, at least twenty years, or for the rest of the lifetime of a subject in need thereof.

The active agents generally are administered in pharmaceutical compositions, that either are commercially available in doses suitable for use in the present invention, as described herein, or that can be formulated appropriately to provide such doses. The pharmaceutical compositions can be made by any technique known in the art or described herein, as detailed below.

6. Methods of Making Pharmaceutical Compositions and Kits

Another aspect of the present invention involves use of active agents described herein for the preparation of a pharmaceutical composition for treating, reducing, preventing, and/or delaying Parkinson˜s disease, a disorder related thereto, or a symptom thereof, in a subject suffering from, or pre-disposed to, Parkinson˜s disease, a disorder related thereto, or other condition where a dopaminergic agent, such as L-Dopa, is chronically administered. In particular embodiments, the pharmaceutical composition may be formulated using tapentadol, a pharmaceutically effective salt thereof or derivative thereof, in combination with an agent known to treat Parkinson˜s disease or a related disorder, and a derivative of an agent known to treat Parkinson˜s disease or a related disorder (such as a dopaminergic agent like L-Dopa), and mixing with a pharmaceutically acceptable carrier. In some embodiments, the pharmaceutical composition may be formulated using stavudine or a pharmaceutically effective salt or derivative of stavudine and/or nabumetone or a pharmaceutically effective salt or derivative of nabumetone, in combination with an agent known to treat Parkinson˜s disease or related disorder, or derivative thereof. In some embodiments, the pharmaceutical composition may be formulated using tapentadol, a pharmaceutically effective salt or derivative thereof, stavudine, a pharmaceutically effective salt or derivative thereof, and/or nabumetone or a pharmaceutically effective salt or derivative thereof, in combination with an agent known to treat Parkinson˜s disease or related disorder, or derivative thereof.

The pharmaceutically acceptable carrier generally is selected based on the intended mode of administration, as well as the active agents to be delivered. In a specific embodiment, the term 'pharmaceutically acceptable_ means approved by a regulatory agency of the Federal or a state government or listed in the U.S. Pharmacopeia or other generally recognized pharmacopeia for use in animals, and more particularly in humans. The term also may refer to means approved as indicated herein, specifically with respect to the active agent of the pharmaceutical composition. For example, pharmaceutically acceptable carriers for use with tapentadol-containing compositions include carriers already in use, or approved for use, for tapentadol formulations currently on the market.

The term 'carrier_ refers to a diluent, adjuvant (e.g., Freund's complete and incomplete adjuvant), excipient, or vehicle with which the agent is administered. Such pharmaceutical carriers can be sterile liquids, such as water and oils, including those of petroleum, animal, vegetable, or synthetic origin, including, e.g., peanut oil, soybean oil, mineral oil, sesame oil and the like. Water is a common carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Additional examples of pharmaceutically acceptable carriers, excipients, and stabilizers include, but are not limited to, buffers such as phosphate, citrate, and other organic acids; antioxidants including ascorbic acid; low molecular weight polypeptides; proteins, such as serum albumin and gelatin; hydrophilic polymers such as polyvinyl pyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™ as known in the art. The pharmaceutical composition can also include a lubricant, a wetting agent, a sweetener, a flavoring agent, an emulsifier, a suspending agent, and a preservative, in addition to the above ingredients. These compositions can take the form of solutions, suspensions, emulsion, tablets, pills, capsules, powders, sustained-release formulations and the like.

In certain embodiments of the invention, pharmaceutical compositions are provided for use in accordance with the methods of the invention, said pharmaceutical compositions comprising a therapeutically and/or prophylactically effective amount of an agent described herein along with a pharmaceutically acceptable carrier.

In some embodiments, the tapentadol-containing pharmaceutical compositions are provided as tablets or solutions for oral intake. In preferred embodiments, such tablets or solutions also contain the one or more of the following inactive ingredients: croscarmellose sodium, lactose monohydrate, magnesium stearate, microcrystalline cellulose, and povidone. Such tablets or solutions also contain the following inactive ingredients: hypromellose, magnesium stearate, polyethylene glycol, polyvinyl alcohol, talc, silicified microcrystalline cellulose, titanium dioxide, FD&C Blue Number 2 Aluminum Lake, yellow iron oxide (see, e.g., http://www.hc-sc.gc.ca/dhp-mps/prodpharma/sbd-smd/drug-med/sbd_smd_2011_nucynta_cr133167-eng.php (Summary basis of Decision (SBD) for NNUCY NTAù CR, Health Canada, Date Modified: Apr. 26, 2011)). In some embodiments, the tapentadol-containing tablets are film-coated. The film coatings may contain polyvinyl alcohol, titanium dioxide, polyethylene glycol, talc, and the colorant FD&C Yellow #6 aluminum lake. Some film coatings may additionally contain colorant D&C Yellow #10 aluminum lake.

In preferred embodiments, pharmaceutical compositions are formulated as tablets or capsules for immediate release, e.g., where the formulations provide immediate release of one or more of the administered agents and, in particular, tapentadol and levodopa. For immediate release formulations, testing regarding dissolution is an important part of pharmaceutical development for solid oral dosage forms. USP type I and II dissolution apparatus may be used to test dissolution rates. Immediate release typically means that about 75% of the active agent is dissolved within 45 minutes. In dissolution testing, 'rapidly dissolving_ means about 85% is dissolved in 30 minutes; and 'very rapidly dissolving_ means about 85% is dissolved in 15 minutes. The following media may be considered for immediate release products during development studies: pH 6.8 buffer (or simulated intestinal fluid without enzymes); pH 4.5 buffer; pH 1.2 buffer (or simulated gastric fluid without enzymes), or 0.1 M hydrochloric acid; water may be considered as an additional medium.

In one embodiment, the present invention provides an immediate release formulation comprising at least one active agent, preferably tapentadol, along with a gelling polymeric product, such as natural gums and polymers, and optionally a foam forming agent, and at least one pharmaceutically acceptable carrier. In some embodiments, the formulation provides immediate release of the active agent and has an in vitro dissolution profile that is equal to or greater than 75% of the active agent dissolving in 20 minutes after administration, measured by appropriate methods, such as USP type I and II dissolution apparatus. In preferred embodiments, the formulation provides immediate release of the active agent and has an in vitro dissolution profile that is more than 75% of the active agent dissolving within 10 minutes and/or more than 80% of the active agent dissolving within 30 minutes.

In some embodiments, pharmaceutical compositions for use in the invention are formulated for sustained release, e.g., where the formulations provide extended release and thus extended half-life of the administered agent. Common reservoir devices include, for example, membranes, capsules, film-coated capsules, microcapsules, liposomes, and hollow fibers. Monolithic (matrix) device are a second type of diffusion controlled system, wherein the pharmaceutical compositions are dispersed or dissolved in an rate-controlling matrix (e.g., a polymer matrix). Agents described herein can be homogeneously dispersed throughout a rate-controlling matrix and the rate of release is controlled by diffusion through the matrix. Polymers suitable for use in the monolithic matrix device include naturally occurring polymers, synthetic polymers and synthetically modified natural polymers, as well as polymer derivatives.

In preferred embodiments, the agent for use in the invention is substantially purified (i.e., substantially free from substances that limit its effect or produce undesired side-effects). In a specific embodiment, the host or subject is an animal, preferably a mammal such as non-primate (e.g., cows, pigs, horses, cats, dogs, rats, mice, etc.) and a primate (e.g., monkey such as, a cynomolgous monkey and a human). In a preferred embodiment, the host is a human.

The compositions for use in the invention include bulk drug compositions useful in the manufacture of pharmaceutical compositions (e.g., impure or non-sterile compositions) as well as pharmaceutical compositions (i.e., compositions that are suitable for administration to a subject or patient). Bulk drug compositions can be used in the preparation of unit dosage forms, e.g., comprising a prophylactically or therapeutically effective amount of an agent disclosed herein or a combination of those agents and a pharmaceutically acceptable carrier.

The invention provides further kits that can be used in the disclosed methods. In one embodiment, a kit comprises one or more agents for use in the invention, e.g., in one or more containers. In another embodiment, a kit further comprises one or more other prophylactic or therapeutic agents useful for the treatment of Parkinson˜s disease, a disorder related thereto, a condition associated with gait problems, or other conditions treated with dopaminergic agents, in one or more containers. For example, in some embodiments, the invention provides a pharmaceutical pack or kit comprising one or more containers filled with one or more of the ingredients of the pharmaceutical compositions described herein.

In one embodiment, the invention provides a kit comprising two containers, where one contains tapentadol hydrochloride and the other levodopa. In a preferred embodiment, the invention provides a kit comprising multiple containers, where a number of the containers provide tapentadol hydrochloride and others contain provide levodopa, e.g., where the levodopa is contained in amounts to provide in an amount typically taken at one time during advanced stages of PD; and/or where the tapentadol component is contained in amounts to provide a dose of about 126 mg/day or more (such as amounts to provide a daily dose of about 75 mg, about 100 mg, about 115 mg, about 120 mg, about 125 mg, about 130 mg, about 140 mg, about 150 mg, about 175 mg/day, about 200 mg/day, about 250 mg/day or about 300 mg/day), e.g., by dividing the daily dose into three containers, each containing the amount taken at one time, three times a day.

Optionally associated with such container(s) can be a notice in the form prescribed by a governmental agency regulating the manufacture, use or sale of pharmaceuticals or biological products, which notice reflects approval by the agency of manufacture, use, or sale for human administration.

Generally, the ingredients of compositions for us in the invention are supplied either separately or mixed together in unit dosage form, for example, as a dry powder or water-free concentrate in a hermetically sealed container such as an ampoule or sachet indicating the quantity of agent or active agent; or as tablets or capsules. Where the composition is to be administered orally, it can be provided in one or more tablets or capsules, e.g., providing unit doses of each of the one or more active agents for administration. Alternatively, where the composition is administered orally, it may be provided as a powder for adding to water or other beverage, to prepare a solution for drinking. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

EXAMPLES

The following examples evidence the effect of the tapentadol, stavudine, and nabumetone in animal models of Parkinson˜s disease (PD). To model Parkinson˜s disease (PD), a neurotoxin 6-OHDA (6-hyroxydopamine) based method was used in zebrafish and in mice. In this model, 6-OHDA-lesions induce motor manifestations in zebrafish and in mice, such as reduced locomotor ability, and the loss of dopaminergic neurons. Based on the 6-OHDA PD zebrafish model, compounds from a small molecules library were screened for rescue of the parkinsonian phenotype (Example 1, see below). From the panel of 'hits_ identified on the screen, the results obtained were further evaluated in the zebrafish PD model. Efficacy of two of the top selected therapeutic compounds then were tested in a mouse PD model (Example 5, see below).

Further, a mice model was developed to mimic non-responsive (OFF) periods of L-Dopa, allowing investigation of selected compounds in a pre-clinical model. When chronically treated with L-Dopa, mice of this model exhibited aggravated gait impairments and, critically, tapentadol hydrochloride was able to rescue this condition (Example 7, see below).

Example 1—Identification of Compounds that Protect Against PD-Phenotypes

Compounds that rescue the parkinsonian phenotype were screened for, from within a small molecules library. As the screening step was blinded, the compounds initially were named with a code number. Details of the molecules are provided in Table 1, below.

TABLE 1

| Name | CAS Number | Chemical structure | Drugbank code |
| --- | --- | --- | --- |
| STAVUDINE | 3056-17-5 | 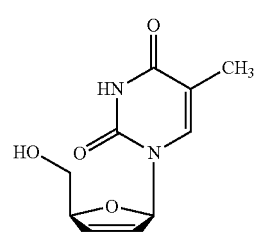 [SMILES: Cc1cn([C@H]2C=C[C@@H](CO)O2)c(=O)[nH]c1=O] | DB00649 |

TABLE 1-continued

| Name | CAS Number | Chemical structure | Drugbank code |
|---|---|---|---|
| TAPENTALDOL HYDROCHLORIDE | 175591-23-8 | 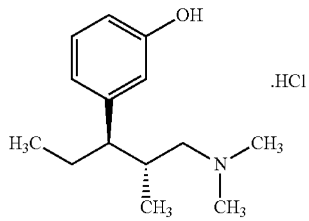 [SMILES: CC[C@@H](c1cccc(O)c1)[C@@H](C)CN(C)C ; ".HCl"] | DB06204 |
| NABUMETONE | 42924-53-8 | 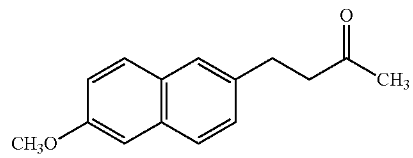 | DB00461 |

Zebrafish is a vertebrate model system that has been widely used in drug discovery in advance of mammalian pre-clinical studies. It allows in vivo phenotypic screening and has the potential to identify novel therapeutic targets since phenotype recovery will reflect the integrated physiology of the entire organism. Briefly, the screen involves the following three noteworthy features:

1) In vivo testing—the screen has several advantages over traditional in vitro cell culture screens, since it integrates all the effects over an entire organism;
2) Phenotypic—the screen is agnostic to the target, so when the target is unknown, the effect can be on-target or off-target;
3) Systemic drug delivery—drug was added to the mounting media to provide for systemic administration to the zebrafish.

In the present study, screening included molecules previously-approved for marketing (directional to previously approved molecule). Specifically, a small molecule library was screened, where the library is composed mainly of FDA-approved therapeutic molecules. Some further may have well-documented pharmacological activities, such as: target/mode of action, toxicity and ADME.

The in vivo screening of small molecules in a zebrafish PD mode identified several promising candidate therapeutics for PD. The screen was based on both the recovery of impaired locomotor behavior and dopaminergic neuronal loss. For some of the candidates, LD50, maximum and minimum effective drug doses, were determined in the disease context of the zebrafish model, using the chemical identified from the library, as obtained from the a manufacturer.

Specifically, the chemicals identified were purchased from a commercial source to confirm the previously obtained results on their efficacy on rescuing PD-phenotypes, in term of locomotor behavior rescue, in the 6OHDA-model (repetition of the behavior and neurorescue assay). Results are shown in FIGS. 1A-1B. The Figure shows locomotor behavior rescue results of 7 candidate molecules for the two parameters—total distance moved (FIG. 1A) and number of jumps (FIG. 1B). Values were normalized for the mean of disease state in each experiment (disease=1). Each plot contains data from 3 independent experiments with a total of 24 larvae. As a control, zebrafish were treated with only the vehicle, ascorbic acid. Based on these, results tapentadol and nabumetone are strong candidates.

Figure 2:
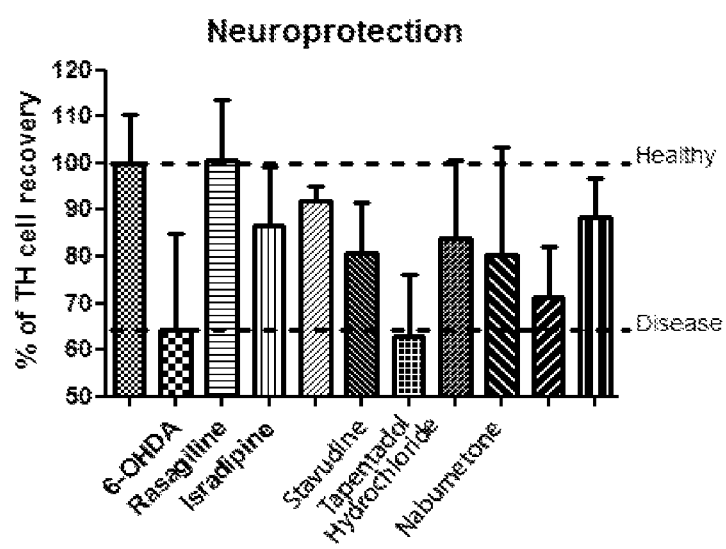
FIG. 2: Percentage of TH-positive neurons rescue for 7 candidate molecules, showing rescue of dopaminergic neurons positive for Tyrosine hydroxylase (TH) in the substancia nigra pars Compacta of 6-OHDA treated zebrafish larvae.

The 7 candidates also were tested in terms of rescue of dopaminergic neurons positive for Tyrosine hydroxylase (Th) in the substancia nigra pars compacta of the test animals. Results are shown in FIG. 2. That is, FIG. 2 shows the percentage of TH-positive neurons rescued for the 7 candidate molecules. Results were normalized for healthy control values (healthy control=100% of neurons). As a control, zebrafish were treated with only the vehicle, ascorbic acid. '6-OHDA_ represents results in zebrafish receiving no treatment.

Example 2—Dose-Response Studies of Candidate and Controls

For each hit compound, a dose-response curve across a range of concentrations was performed to find the minimal and maximal effective concentrations and also the LD50 in this disease context, again using the zebrafish PD model (6-OHDA).

Instead of the typical dose-response curve with one peak concentration—effect increasing with concentration—for most of the cases, a dose-response curve with two concentration peaks was observed—one peak at a low concentration and other at approximately 10 times higher concentration.

For the 7 molecules, a long range curve was performed along a concentration range that comprises large intervals, whereas the small range was performed with concentrations around the lowest concentration peak detected in the long range curve. The results of interest for tested molecules are summarized in Table 2.

TABLE 2

| | LD50 | Optimal dose | Neurorescue |
|---|---|---|---|
| L-Dopa | >5 mM | 250 μM | no |
| Isradipine | 0.42 μM | 0.045 μM | confirmed |
| Rasagiline | 187.5 μM | 25 μM | confirmed P < 0.11 |
| nabumetone | ND | 0.9 μM | confirmed |
| stavudine | >10 mM | 50 μM | confirmed p < 0.09 |
| tapentadol | 8079 μM | 48.5 μM | Confirmed p < 0.055 |

ND = not determined/Not done

Noteworthy, these dose-response curves were done on disease-induced larvae, and the mean of the controls and disease state was plotted. Each concentration result corresponds to the mean of 8 fish and one experiment (ëSD). For these experiments, Tubingen (TU) wild-type zebrafish, a specific strain of wild-type zebrafish, were used.

All the chemicals were prepared in accordance with the maximum solubility and were preferably dissolved in water, in accordance with specifications of the chemical molecules (see Table 3).

FIG. 4B, the small range plot, phenotype recovery did not occur with 0.0056 μM, but around 0.056 μM a new peak appeared at 0.045 μm, as well as another peak at 0.084 μM. Further small range results are provided in FIG. 4C. Results after immunohistochemistry are shown in FIGS. 4D-4E. Of the two concentrations, the optimal concentration was cho-

TABLE 3

| Molecules | Brand | Quantity | Powder storage | Solution storage | Molecular Weight | Solubility | LD50 | Effective human dose | Effective rat dose |
|---|---|---|---|---|---|---|---|---|---|
| L-Dopa | Sigma-Aldrich | 5 G | RT | −80 ℃. | 197.2 g/mol | 3.3 mg/ml in water | 1780 mg/kg (rat, oral) | Initial: 250-500 mg/day, 2× Maintenance 3000-6000 mg/day, 3× or more | |
| Isradipine | Sigma-Aldrich | 5 MG | 4 ℃. | −80 ℃. | 371.39 g/mol | 25 mg/ml in DMSO | 889.85 g/kg (rat) | 2.5-10 mg/day | |
| Rasagiline | Sigma-Aldrich | 10 MG | −20 ℃. | −80 ℃. | 267.34 g/mol | 53 mg/ml in water | 300 mg/kg (rat) | 1 mg/day or 0.017 mg/kg/day | 0.8 mg/kg/day sc |
| Nabumetone | Sigma-Aldrich | 5 G | RT | −80 ℃. | 228.29 g/mol | 50 mg/ml in DMSO | 4290 mg/kg (mouse) or 3880 mg/kg (rat) | 500-750 mg/day, 1-4× | |
| stavudine | Sigma-Aldrich | 10 MG | −20 ℃. | −80 ℃. | 224.21 g/mol | 83 mg/ml in water | 4 g/kg (rat) | 15-40 mg/day, 1-2× | |
| tapentadol | Thonson Technologies | 1 G | | | 257.81 g/mol | | 300-350 mg/Kg (oral, mice) | 50-100 mg every 4-6 h | |

Experiments were conducted using L-dopa, isradipine, and rasagiline as control molecules.

L-Dopa

Results for L-Dopa are shown in FIGS. 3A-3D. Of note, L-Dopa is applied in each well at the time the plate is read because it is rapidly metabolized (30 minutes after application corresponds to the acclimatization period; in the next hour, the effect is measured—1 h 30 minutes of efficacy). As seen in FIG. 3A, in the long range plot, L-Dopa effective concentrations are 25 and 250 μM. As seen in FIG. 3B, in the small range plot, the recovery of the phenotype is milder and the 100 μM concentration shows the best effect. Because of the low stability of the compound, 250 μM was used as the optimal concentration.

As seen in FIG. 3C, at that concentration and with one application, L-Dopa does not induce the recovery of TH+ neurons in accordance with reports in the literature. However, some studies indicate that L-Dopa can have some degree of neuroprotection. Studies using CT scans have suggested that L-dopa was associated with higher demise rates of dopaminergic neurons. These studies have been supported by different imaging studies in PD patients. For instance, CALM-PD trial showed that PD patients who were randomized to L-dopa had a greater rate of dopamine transporter signal loss compared with the placebo group as demonstrated by b-cit single-photon emission computerized tomography. Moreover, in vitro studies suggested that L-dopa may exert an antioxidant or neurotrophic-like effect. In accordance with this data, our results (FIG. 3C) suggest that in a case where the disease is highly induced (sig ****) L-dopa has no ability to recover the affected neurons.

On the other hand, as seen in FIG. 3D, where the disease is less severe (sig *), L-Dopa can be neuroprotective (p=0.06). However, these results should be considered preliminary.

Isradipine

Results for isradipine are shown in FIGS. 4A-4E. As seen in FIG. 4A, the long range plot, isradipine effective concentrations are 0.0056 μM and 0.056 μM to a lesser extent. In sen as the lowest concentration, 0.045 μM, because isradipine is toxic at higher concentrations.

Rasagiline

Results for rasagiline are shown in FIGS. 5A-5D. As seen in FIG. 5A, the long range plot, Rasagiline effective concentrations are around 1 μM and 50 μM. In FIG. 5B, the small range plot, none of these concentrations were reproduced; the only concentration that shows a rescue of the behavior effect was 25 μM. This concentration was chosen to evaluate the neuroprotective effect of rasagiline (FIG. 5C), that was confirmed with p<0.11 with a medium state of disease induced. During the screen, the concentration used was also 25 μM M in 100% DMSO and a neuroprotective effect was observed with p<0.06 (FIG. 5D).

Candidate Molecules

The same analysis was used for the candidate molecules, and the results for tapentadol, stavudine, and nabumetone are discussed below.

Tapentadol

For tapentadol, 48.5 μM was determined to be the optimal concentration based on the results obtained in several behavioral experiments and TH+ cell counts. The therapeutic window was 20-113 μM. Neuroprotective effect was confirmed using the same concentration. LD50 was 8,079 μM. Results are shown in FIGS. 6A-6G.

Specifically, FIG. 6A shows locomotor behavior of 6-OHDA treated zebrafish larvae with tapentadol (n=8 fish). The total distance travelled (mm) was different between the larvae treated with 48.5 μM tapentadol (*=p<0.05) and the disease control (6-OHDA-treated) with a mean distance travelled of ~200 mm. FIG. 6B shows, for the number of jumps, 56.25 μM tapentadol was validated as recovering the 6-OHDA induced behavior. FIG. 6B shows that duration of freezing periods was not recovered with the 48.5 μM concentration of tapentadol; L-Dopa treatment also elicited no recovery of this phenotype, when compared with the 6-OHDA treated larvae (disease induction p<0.01). The positive control used was methylphenidate.

FIGS. 6C-6D show, respectively, duration of freezing periods and the number of dopaminergic neurons positive for Tyrosine hydroxylase (Th) in the control (non-6-OHDA treated), disease state (6-OHDA treated; disease induction p<0.05), and 6-OHDA treated larvae with 48.5 μM of tapentadol. As seen, recovery was observed with 48.5 μM tapentadol treatment (p<0.055). Each dot represents an individual n=6-7.

FIGS. 6E-6G show representative Z-projections of confocal stacks of whole-mount anti-TH immunohistochemistry in 6 days post-fertilization (dpf) of zebrafish larvae (age of the fish) control (FIG. 6E), 6-OHDA (FIG. 6F), and tapentadol treated-larvae (FIG. 6G). These results are indicative of disease-modifying properties of tapentadol.

Notably, the dose response curve indicated that the tapentadol therapeutic window is larger than that of stavudine.

Stavudine

For stavudine, 50 μM was considered the optimal concentration based on results obtained in several behavioral experiments and TH+ cell counts. The therapeutic window was 50-70 μM. Neuroprotective effect and recovery of freezing (i.e., reduction or elimination of number of freezing episodes and/or reduction in the frequency of freezing episodes, demonstrating a reduction in freezing episodes, was confirmed with the same concentration. Cell organization is similar to wt. The LD50>10,000 μM. Results are shown in FIGS. 7A-G.

FIG. 7A shows locomotor behavior of 6-OHDA treated zebrafish larvae with stavudine (n=8 fish). The total distance travelled (mm) was different between the larvae treated with 50 μM stavudine (p<0.0001) and the disease control (6-OHDA-treated) with a mean distance travelled of 400 mm between both groups. FIG. 7B shows that, for the number of jumps, the same concentration of 50 μM stavudine was validated as recovering the 6-OHDA induced behavior. FIG. 7C shows duration of freezing periods also was recovered with the 50 μM concentration of stavudine, whereas L-Dopa treatment showed no recovery of this phenotype, when compared with 6-OHDA-treated larvae (disease was induced with p<0.01). The positive control used was methylphenidate.

FIGS. 7C-7D show, respectively, duration of freezing periods and the number of dopaminergic neurons positive for Tyrosine hydroxylase (Th) in the control (non-6-OHDA treated), disease state (6-OHDA treated; disease induction p<0.05), and 6-OHDA treated larvae treated with 30 and 50 μM of stavudine. As seen, recovery only was observed with the 50 μM stavudine dose (p<0.09). Each dot represents an individual n=3-5.

FIGS. 7E-7G show representative Z-projections of confocal stacks of whole-mount anti-TH immunohistochemistry in 6 dpf control (FIG. 7E), 6-OHDA (FIG. 7F), and stavudine treated-larvae (FIG. 7G). These results are indicative of disease-modifying properties.

Nabumetone

For nabumetone, 0.9 μM was considered the optimal concentration based on results obtained in several behavioral experiments and TH+ cell counts. Neuroprotective effect was confirmed with the same concentration. At 18 μM, there were no dead embryos but at 27 μM all of the embryos were dead (data not shown); therefore we could not determine with precision the LD50. Notably, nabumetone rescued disease phenotype in larvae where the disease was strongly induced. Results are shown in FIGS. 8A-8G.

FIG. 8A shows locomotor behavior of 6-OHDA treated zebrafish larvae with nabumetone (n=8 fish). The total distance travelled (mm) was different between the larvae treated with 0.456 and 0.91 μM nabumetone (**=p<0.01) and the disease control (6-OHDA-treated) with a mean distance travelled of ~200 mm amongst the groups. FIG. 8B shows, for the number of jumps, only the 0.456 μM nabumetone concentration was validated as recovering the 6-OHDA induced behavior.

As FIG. 8C shows, duration of freezing periods was not recovered with 0.91 μM of nabumetone, when compared with the 6-OHDA treated larvae (disease induction p<0,01). The positive control used was Methylphenidate. As FIG. 8D shows, the number of dopaminergic neurons positive for Tyrosine hydroxylase were quantified in the control (non-6-OHDA treated), disease state (6-OHDA treated, disease induction p<0.05) and 6-OHDA larvae treated with 0.456 and 0.91 μM of nabumetone. Recovery was observed with 0.91 μM (p<0.05) and with 0.456 μM nabumetone (p<0.17). Each dot represents an individual n=4-6.

FIGS. 8E-8G show representative Z-projections of confocal stacks of whole-mount anti-TH immunohistochemistry in 6 dpf control (FIG. 8E), 6-OHDA (FIG. 8F), and nabumetone treated-larvae (FIG. 8G). These results are indicative of disease-modifying properties for nabumetone.

In sum, dose response curves were very useful for validating the importance of concentration of candidate molecules in terms of their effect on parkinsonian behavior, and showing that an increase in concentration does not necessarily correspond to an increase in effect.

Example 3—Identification of Compounds that Correct Freezing of Gait

In the zebrafish model, the locomotor impairment was measured and related with bradykinesia in patients. Tests included evaluating 'freezing_ in response to a light/dark stimulus. 6-OHDA induced larvae had fewer freezing episodes but spent longer periods in the frozen state. In previous studies, the duration of freezing episodes has been analyzed in PD patients. The 7 selected molecules were tested using their respective optimal concentrations, and positive results were obtained with tapentadol and stavudine. Methylphenidate also was found to exhibit more consistent freezing recovery. Nonetheless, it is an inhibitor of the neuronal dopamine transporter and since 6-OHDA needs DAT to enter the neuron and induce the disease, methylphenidate may be a false positive. Results are shown in FIGS. 9A-9D.

As FIG. 9A shows, none of the control molecules tested can revert the freezing phenotype.

As FIGS. 9B-9C show, freezing recovery was tested using 7 candidate molecules at optimal concentrations, in an exemplary experiment with n=8 fish, and methylphenidate and amantadine at 25 μM.

For stavudine and tapentadol, several experiments were repeated. FIG. 9D shows results using stavudine, tapentadol, and a combination thereof at optimal concentrations. As seen in FIG. 9D, stavudine reverted freezing in n=4 different experiments, whereas tapentadol and the combination (stavudine and tapentadol) did not revert freezing phenotype in these experiments.

Example 4—Analysis of Interaction with L-Dopa in Total Distance 6-OHDA Larvae Move In addition, the effect of the co-administration with L-Dopa also was evaluated, for various candidates. Since in clinical trials, the majority of the patients are already taking L-Dopa, it made sense to evaluate the effect of candidate molecules with L-Dopa. Initially, effect of L-Dopa was measured in ON periods and without any candidate molecule for 24 h.

This test aimed to see whether there was a decrease in the L-Dopa effect when used in combination with a candidate molecule. Rasagiline with L-Dopa had an increased effect when compared with rasagiline alone, an optimal outcome. However, with isradipine, the reverse is true—isradipine in conjunction with L-Dopa lost its effect. For nabumetone, the effect was the same with or without L-Dopa.

For tapentadol, stavudine, and the combination thereof, several experiments were conducted. The conclusions were that stavudine's activity was not affected (more or less the same), with better results obtained when L-dopa was less concentrated.

Experiments were performed with stavudine and L-dopa at two different concentrations, 250 μM and 125 μM. In this experiment, stavudine was least effective in conjunction with L-dopa. Testing using a lower L-Dopa concentration (125 μM) provides results indicating that the candidate compounds do not compensate for a decrease of L-Dopa concentration, i.e., cannot completely substitute for the L-Dopa effect.

Experimental details of further tests conducted with tapentadol and L-Dopa are provided in Table 4.

TABLE 4

| Drugs | L-DOPA alone | Tapentadol w L-Dopa |
|---|---|---|
| Tapentadol HCl | 250 p < 0.01 125 ns | Alone p < 0.06 L-Dopa 250 μM less effective than with 125 μM tapentadol (ns) |
| Tapentadol HCl | 250 p < 0.07 125 ns | Alone p < 0.05 L-Dopa 250 μM equally effective as 125 μM tapentadol ns | ns = not significant

Tapentadol's activity also was not affected (more or less the same) by co-administration with L-Dopa. However there are many other candidates where the effect was reduced in conjunction with L-Dopa. Further data regarding tapentadol is provided in FIG. 10.

Figure 10:
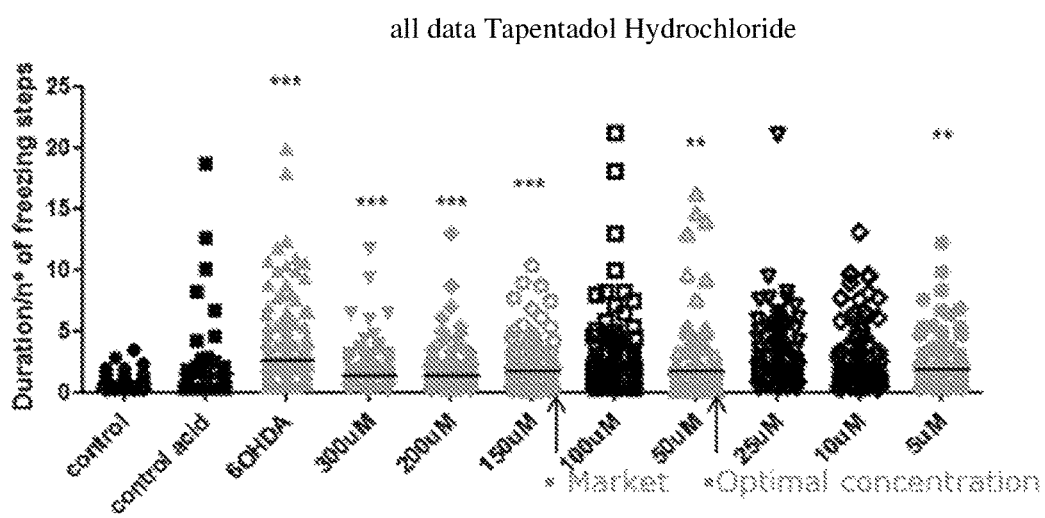
FIG. 10: Results testing tapentadol, at different concentrations, with L-Dopa, for duration of freezing steps.

As FIG. 10 shows, tapentadol can revert the freezing phenotype over a range of concentrations, specifically, from about 300 to about 150 μM, at about 50 μM and at about 5 μM.

In sum, preliminary results indicated that the recovery effect of stavudine on locomotor behavior is not influenced by the presence of L-Dopa. Moreover, stavudine showed improved efficacy in the presence of lower concentration of L-Dopa. In the case of tapentadol hydrochloride, locomotor recovery effect was the same or improved in the presence of L-Dopa, including higher concentrations of L-Dopa. In conclusion, L-Dopa causes no major changes in the activities of stavudine or tapentadol hydrochloride when co-administered at the same time in this model system using 6-OHDA zebrafish.

Regarding nabumetone, zebrafish data indicate that this molecule can revert the locomotor phenotype and has a potential disease modifying effect. Initial results, however, do not show an ability to recover freezing phenotype. Of note, the effective concentration was far below the dose tested during the screen, which might indicate a different stability of the compound in different solvents.

In sum, the following conclusions arise from the zebrafish results:

Stavudine, tapentadol hydrochloride, and nabumetone were demonstrated to have activity in recovering locomotor behavior, which parallels bradykinesia in patients with Parkinson's. Stavudine, tapentadol hydrochloride, and nabumetone thus show prospective neuro-restorative or disease-modifying capacities. Further, both tapentadol and stavudine demonstrate the ability to rescue freezing. Further still, both stavudine and tapentadol hydrochloride retain the ability to recover locomotor behavior, when each was co-administered with L-Dopa. Moreover, these three candidates do not seem to be toxic at the concentrations administered and the effective concentrations are far from the respective LD50 doses.

Example 5—Pre-Clinical Efficacy of Candidate Compounds

Stavudine and tapentadol hydrochloride were selected for pre-clinical testing in a 6-OHDA mouse model. These two molecules were able to recover locomotor behavior and neuronal loss (disease-modifying properties).

Dose concentrations were converted from zebrafish to mice.

The unilateral striatal 6-OHDA mice model was used in this study to test pre-clinical efficacy of candidate compounds for use in treatment of Parkinson's disease. Animals were injected with 10 μg of 6-OHDA or ascorbic acid (sham/vehicle control) to induce the disease. Specifically, 12 week old (1wo_) CD-1 male mice received an intracranial injection of the neurotoxin 6-OHDA at the following coordinates: AP +0.9 mm, ML +2.0 mm, DV −3.2 mm (corresponding to the spatial coordinates Anterior-Posterior (AP), Medial-Lateral (ML), and Dorsal-Ventral (DV)). Disease was induced for 7 days and treatment started at this time point.

Animals were treated on a daily basis through intraperitoneal injection, as shown in Table 5 below, summarizing the experimental design.

TABLE 5

| Administration route | intraperitoneal injection |
|---|---|
| Administration frequency | every day, once a day |
| Treatment initiation | 7 days post-injection (dpi) |
| Treatment duration | 21 days |
| Treatment end | 28 days post injection (dpi) |

Sham (vehicle) group and disease control group received saline injections while positive control group received 18 mg/kg/day of levodopa after a 12 mg/kg/day injection of benserazide (to inhibit decarboxylation of levodopa before it reaches the brain).

Figure 11:
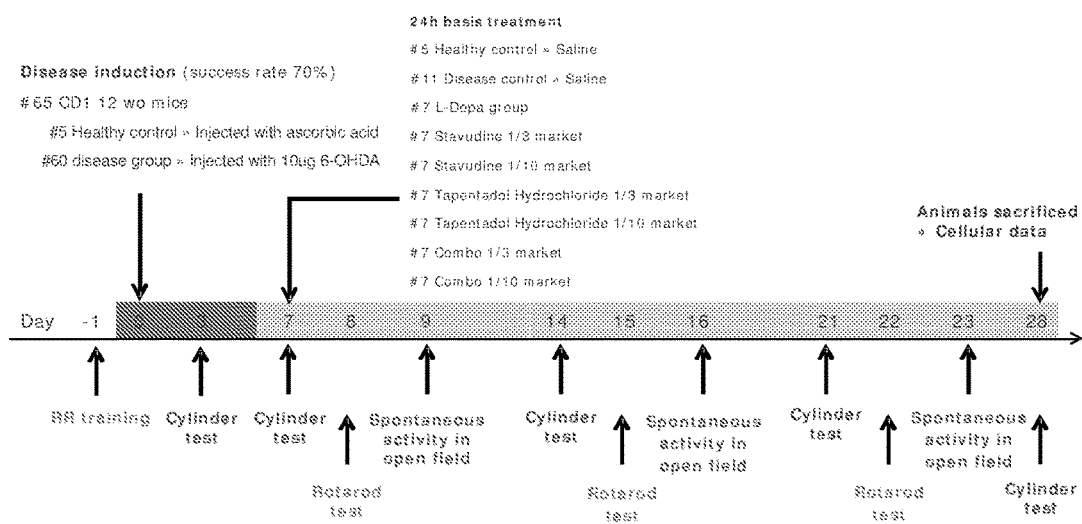
FIG. 11: Experimental design for tapentadol hydrochloride and stavudine pre-clinical testing in a 6-OHDA mouse model.

Tapentadol hydrochloride was tested at 2.8 mg/kg/day (concentration 1 (C1), equivalent to ⅓ of the lowest dose currently on the market) and 0.9 mg/kg/day (concentration 2 (C2), equivalent to 1/10 of the lowest dose currently on the market). Stavudine was tested at 0.9 mg/kg/day (concentration 1 (C1), equivalent to ⅓ of the lowest dose currently on the market) and 0.3 mg/kg/day (concentration 2 (C2), equivalent to 1/10 of the lowest dose currently on the market). Both molecules also were tested in combination at the low and high concentrations (C1 and C2, respectively). The mice were treated for 21 days, where behavioral tests were performed. On the 28th day after intracranial injection, animals were sacrificed and brain dissected for histology analyses. The experimental design is shown in FIG. 11.

Behavioral tests were used to evaluate the efficacy of stavudine and tapentadol hydrochloride, at the various concentrations, as well as the efficacy of the combination of the two candidates (Combo). The behavioral tests used included: Rotarod test, cylinder test, and open field tests. In each test, different parameters were analyzed, with the focus being on evaluating locomotor behavior recovery. Stavudine and tapentadol hydrochloride were administered 30 min before testing; L-Dopa was given 30 min before the cylinder test and at the end of the Rotarord test. Other parameters also evaluated included tremors and abnormal involuntary movements (AIMs).

Results

Animals˜ welfare and weight were monitored on a daily basis. There was no significant difference in animals˜ weight among groups with time (data not shown).

Rotarod Test

The Rotarod test is a performance test based on a rotating rod with forced motor activity being applied. This test evaluates motor performance and equilibrium. For the Rotarod test, the parameters speed and latency to fall were analyzed for each group. Three independent trials were done and data shown is the mean of the trials for each animal. Trials started 30 minutes post therapeutic administration, with the exception of L-Dopa (which was measured 24 hours post-treatment, L-Dopa OFF period), and animals were allowed to rest for 30 minutes between trials.

The L-Dopa group did not behave as expected, possibly because the dosage applied induced abnormal involuntary movements (AIMs). Animals under L-Dopa treatment showed involuntary and unstoppable left turns, which made it impossible to test them correctly using the Rotarod behavioral test. The trial was valid for 8 and 15 days post lesion, but not for 22 days post lesion, because only at these two timepoints was there a significant motor impairment in the 6-OHDA group compared to the healthy group. The group of animals treated with tapentadol hydrochloride at C1 showed the best recovery between groups, although not significant when compared to the 6-OHDA (untreated) group, for the two parameters evaluated. For all the other groups, the recovery was null or mild (FIGS. 12A-12F).

As shown, tapentadol hydrochloride-treated animals presented behavioral recovery over time, visible in the results regarding both latency to fall (FIG. 12A) and speed (FIG. 12B). Stavudine and Combo, at both dosages tested, did not have an effect on mice behavior, as shown in the results for latency to fall (FIGS. 12C and 12E, respectively) and speed (FIGS. 12D and 12F, respectively). Values mean ě SEM (n=5-8). A two-way ANOVA test with Bonferroni post-test was performed to compare group means at each timepoint ('ns_, not significant, *p<0.05).

Cylinder Test

The Cylinder test evaluates spontaneous and exploratory activity, as well as the extension of the lesion caused by 6-OHDA injection. This test involves placing the animal in a clear cylinder and recording its behavior for 5 minutes. Results are shown in FIGS. 13A-13D. The parameters evaluated were: percentage of contralateral paw use (FIG. 13A), number of right turns (FIG. 13B), number of rearings (FIG. 13C), and percentage of animals with tremor (FIG. 13D) per group.

Among these parameters, contralateral paw use and number of right turns were observed most frequently. The test was done 30 minutes after therapeutic administration (for all therapeutics including during the 'ON period_ following L-Dopa administration) and video recorded for 5 minutes to permit further analyses. The 3 and 7 days results shown were prior to any therapeutic initiation.

For percentage of contralateral paw use and number of rearings, animals treated with 6-OHDA showed significant motor impairments compared to vehicle treated animals, at 3 and 7 days post lesion (FIGS. 13A and 13C). Concerning the number of right turns, the 6-OHDA treated group had significantly higher numbers than healthy animals at 7 days post lesion (FIG. 13B). On the other hand, the percentage of animals with tremor was not significantly different between the 6-OHDA treated and healthy groups, at both timepoints (FIG. 13D). This last parameter may not be very robust, so it must be analyzed carefully.

For the percentage of contralateral paw use, the 6-OHDA group had significant motor impairments compared to healthy controls at 14 and 21 days post lesion. As at 28 days post lesion, motor impairments of the 6-OHDA group were not significant for this parameter, this timepoint was not further considered. For the number of right turns, the 6-OHDA group had no significant motor impairments compared to healthy controls at all timepoints evaluated. As such, this parameter also was disregarded for further analyses. Concerning the number of rearings, 21 days post lesion was the only timepoint considered for further analyses, as it was the timepoint where the 6-OHDA group had significant motor impairments compared to healthy controls. For the percentage of animals with tremor, 28 days post lesion timepoint was considered further, because it had a p value very close to what would be considered a significant p value.

Cylinder test results following treatment with L-Dopa or tapentadol hydrochloride, at two different concentrations, are shown in FIGS. 14A-14D, again based on evaluating percentage of contralateral paw use (FIG. 14A), number of right turns (FIG. 14B), number of rearings (FIG. 14C), and percentage of animals with tremor (FIG. 14D) per group.

The L-Dopa group showed results consistent with the literature. For percentage of contralateral paw use and percentage of animals with tremor, motor recovery was observed for animals treated with L-Dopa compared to the 6-OHDA group. For number of rearings there was no difference between the L-Dopa treated and 6-OHDA groups.

The group of animals treated with tapentadol, at concentration 1, on the whole, showed a recovery based on the parameters analyzed, with a significant difference in percentage of animals with tremor at 28 days compared with the 6-OHDA group (FIG. 14D, asterisk). This is indicative of locomotor recovery. Regarding tapentadol at concentration 2, the results did not show significant recovery.

Cylinder test results following treatment with L-Dopa or stavudine, at two different concentrations, are shown in FIGS. 15A-15D. The group of animals treated with stavudine did not show recovery in terms of contralateral paw use, number of rearings, or tremor, when compared with the 6-OHDA group (FIGS. 15A, 15C, and 15D). For the number of right turns (although disregarded), stavudine, at concentration 1, showed phenotypic recovery in a very similar way to L-Dopa (FIG. 15B, comparing blue bars with vertical striped bars).

Cylinder test results following treatment with L-Dopa or a combination of tapentadol hydrochloride and stavudine ('Combo_), each at two different concentrations, are shown in FIGS. 16A-16D. The Combo treated groups showed no difference in the contralateral paw use parameter when compared with the 6-OHDA group (FIG. 16A). For parameters regarding the number of right turns and rearings, the Combo treated animals, using concentration 2, showed mild recovery compared to the 6-OHDA group (FIGS. 16B and 16C, pink bars), while for the tremor parameter, best results were obtained with concentration 1 (FIG. 16D, asterisk).

In sum, FIGS. 14A-14D, 15A-15D, and 16A-16D show Cylinder test results. As seen, 6-OHDA treated mice showed significant motor impairments in the four parameters evaluated at 3 and 7 days post lesion: percentage of contralateral paw use (FIGS. 14A, 15A, and 16A), number of right turns (FIGS. 14B, 15B, and 16B), number of rearings (FIGS. 14C, 15C, and 16C), and percentage of animals with tremor (FIGS. 14D, 15D, and 16D); and results following treatment with tapentadol, stavudine, and combinations thereof are shown. Values mean ě SEM (n=5-8). A two-way ANOVA test with Bonferroni post-test was performed to compare group means at each timepoint (ns, not significant, $*p<0.05$).

In conclusion, the group of animals treated with tapentadol concentration 1 showed strongest recovery compared to the other groups.

Abnormal Involuntary Movements

L-Dopa treatment induces dyskinesia. This condition results in a range of involuntary movements that can be evaluated by video tracking analyses. Data shown in FIGS. 17A-17F demonstrate that, as expected, L-Dopa induced these involuntary movements in mice. Evaluations were performed during two independent trials, 30 and 90 minutes after treatment administration. Scores range from 0 to 4, depending on the severity of the involuntary movements, and scores from both trials were summed. Nonetheless, forelimb and orofacial involuntary movements are extremely hard to detect, and reading errors occur, considering the size of the animals. Total abnormal involuntary movements are the sum of all 4 different involuntary movements evaluated and is the parameter often reported in the literature.

As FIGS. 17A-17F show, abnormal involuntary movements were evaluated using the cylinder test 28 days post injection. Parameters tested included: hyperkinetic and/or dystonic movements of the contralateral forelimb on the sagittal or frontal plane (FIG. 17A), twisted posture of the neck and upper body towards the side contralateral to the lesion (FIG. 17B), twitching of orofacial muscles, empty jaw movements and contralateral tongue protrusion (FIG. 17C), circular locomotion with contralateral side bias (FIG. 17D), total involuntary movements (FIG. 17E), and number of left turns (FIG. 17F). Values mean ě SEM (n=5-8). A one-way ANOVA test with Bonferroni post-test was performed to compare group means at each timepoint ($p<0.01$, $**p<0.0001$). None of the treatments, tapentadol or stavudine of the combination, induced involuntary movements in mice (FIGS. 17A-17F).

Open Field Test

Open field testing evaluates mainly spontaneous activity. For this evaluation, animals were placed in a square box and their activity was recorded following administration of L-Dopa, tapentadol hydrochloride, at two different concentrations (FIGS. 18A-18D), stavudine, at two different concentrations (FIGS. 19A-19D), or the combination thereof (FIGS. 20A-20D). Four different parameters were recorded: maximum velocity (FIGS. 18A, 19A, and 20A), total distance moved (FIGS. 18B, 19B, and 20B), mean velocity (FIGS. 18C, 19C, and 20C), and latency to first reach the walls (FIGS. 18D, 19D, and 20D). All parameters were determined by the analysis of a 5 minute video, recorded 30 minutes after therapeutic administration. Values mean ě SEM (n=3-8). A two-way ANOVA test with Bonferroni post-test was performed to compare group means at each timepoint (ns, not significant, $*p<0.05$, $p<0.01$, $*p<0.001$, $****p<0.0001$).

For total distance moved (FIGS. 18B, 19B, and 20B) and mean velocity (FIGS. 18C, 19C, and 20C), an hour video also was analyzed for an animal per group, to evaluate the effect of the drug with time. For these analyses, a 5 minute video prior to therapeutic administration also was taken. Notably, because this analyses was performed at the 2nd day of therapy, animals may already have been under the influence of the therapeutic. Ethovision V10 system was used for making the videos for analysis.

For maximum velocity (FIGS. 18A, 19A, and 20A), total distance moved (FIGS. 18B, 19B, and 20B), and mean velocity (FIGS. 18C, 19C, and 20C), the 6-OHDA group showed no significant motor impairments compared to healthy controls, at all timepoints evaluated. As such, these parameters were disregarded for further analyses. For latency to walls parameter (FIGS. 18D, 19D, and 20D), at 9 days post lesion, the 6-OHDA group presented significant motor impairments compared to healthy controls. For the other two timepoints, there were no significant motor impairments in the 6-OHDA group compared to healthy controls. At 9 days post lesion, all groups receiving therapy had significant motor improvement compared to the 6-OHDA group and none stood out from others (FIGS. 18D, 19D, and 20D). At this timepoint, the L-Dopa group did not show motor improvement because only two animals were included for the analyses. At this timepoint, animals from each group were removed to make the 1 h video tracking. These analyses could not be included in the 5 minute analyses.

The results from the 1 hour trial were not conclusive (results not shown). This may have occurred for several reasons. For example, the animals had already started therapy 2 days before the trial and might already have been affected by the therapeutic. As such, the 5 minute analysis before therapeutic administration did not represent a true baseline, without therapeutic influence. Another reason for the inconclusive results may be the fact that only one animal per group was used for each of these analyses, which was not representative of the group.

Histological Evaluation of the Disease Model

The disease model itself was evaluated, by evaluating the level of neurodegeneration induced by the administered neurotoxin. Results are shown in FIGS. 21A-21F.

FIGS. 21A-21F show cell loss induced by unilateral intracranial injection of 6-OHDA, evaluated by TH-positive cell counts in the ipsilateral (left) and contralateral (right) side of injection, as seen in microscope images of TH-stained sections of the substantia nigra pars Compacta from healthy control mouse (FIG. 21A) and disease induced mice that are not treated (FIG. 21B) or that are treated with L-Dopa (FIG. 21C), tapentadol hydrochloride (FIG. 21D), or stavudine (FIG. 21E) (scale bar=600 ׀ m); as well as in terms of the percentage of TH-positive cells in the ipsilateral versus contralateral side of injection in each of these groups (FIG. 21F). Mean ě SEM are represented (n=5-8 mice per condition). A n unpaired t test with Welch˜s correction was performed to compare group means (ns, not significant, $p<0.01$, $*p<0.001$, $****p<0.0001$).

Specifically, dopaminergic neurons positive for Tyrosine hydroxylase (TH) were observed and counted in the substantia nigra pars Compacta of 20 ~m coronal cryosections of mouse brain from each test group (FIGS. 21A-21E). In the vehicle control (ascorbic acid), the number of TH+ cells on both sides was the same (as expected) (FIG. 21A), whereas in the 6-OHDA (FIG. 21B) and therapeutic groups (FIGS. 21C-21E), there is a loss of TH+ cells in the ipsilateral side when compared with the contralateral uninjected side, indicating that neurodegeneration took place. The TH+ cells loss was significant for all groups induced with 6-OHDA when compared with the vehicle group and there was no difference among the disease induced groups (FIG. 21F). These results validated the assay and ascertained that all test animals exhibited induced disease. Histological data from Combo groups were not analyzed as some behavioral tests results were not satisfactory.

Conclusion

The aim of this assay was to test two leads selected in the zebrafish screen in a rodent model. Tapentadol, stavudine, and a combination of both at two different dosages were tested in the 6-OHDA mouse model. Motor improvement was evaluated with several behavioral tests. Overall, the tapentadol-treated group showed improved motor behavior when compared to the 6-OHDA group.

Disease induction with 10 μg of 6-OHDA was enough to produce significant TH cell loss in the side of injection when compared to the contralateral side. This cell loss also was enough to induce motor impairments.

Initial evaluations provided positive results for both candidates, stavudine and tapentadol hydrochloride. Particularly, promising results were obtained for tapentadol hydrochloride at 2.8 mg/kg/day (C1, equivalent to ⅓ of the lowest dose currently on the market).

Example 6—Toxicity Assay

The aim of this assay was to test toxicity of tapentadol and tramadol, an analog of tapentadol, in association with L-Dopa treatment. To this end, high doses of both compounds were administered in association with L-Dopa in healthy wild type mice. Their behavior was evaluated with open field tests for 1 h after i.p. injection. After 24 h, animals were sacrificed and necropsy was performed Brief Description of the Methods 9 week old NMRI female mice were used for this assay. Animals were tested for their welfare after two intraperitoneal injections of the test agents using the open field test. Necropsy was done after cervical dislocation. Five groups were used, with 3 animals per group: saline, L-Dopa at 18 mg/kg, tapentadol at 8.3 mg/kg (concentration 1—C1) in combination with L-Dopa, tapentadol at 15 mg/kg (concentration 3—C3) in combination with L-Dopa, and tramadol at 10 mg/kg in combination with L-Dopa. Benserazide at 12 mg/kg was administered 30 minutes prior to administration of these compounds, in all groups. Saline was given to the control group.

After benserazide administration, animals were monitored in the open field for 30 minutes for habituation. The compounds being tested then were administered and the animal's behavior was observed and noted for a 1-hour period in the open field. 24 hours after administration of the compounds, the animals were sacrificed and necropsy performed.

Results—Open Field Test

Animals' behavior was monitored with the open field test. Open field test results are shown in FIGS. 22A-22F.

Six different parameters were recorded: maximum velocity (FIG. 22A), mean velocity (FIG. 22B), total distance moved (FIG. 22C), time spent resting (FIG. 22D), time spent moving slow (FIG. 22E), and time spent moving fast (FIG. 22F), and results provided for tapentadol, tramadol, and L-Dopa treated animals. Values mean ě SEM (n=3). A two-way ANOVA test with Bonferroni post-test was performed to compare group means at each timepoint.

Overall, animals had similar behavior in all parameters recorded. Animals treated with tapentadol at C1 concentration had slightly different behavior in three out of the four parameters analyzed, but the difference was statistically significant only for the mean velocity parameter, at 25 minutes after compound administration (FIG. 22B).

Welfare and Necropsy Results

For administration of the various agents to the animals, two 700 μL injections were administered 30 minutes apart. This injection strategy reduced discomfort to the animals.

Two of the three animals treated with tapentadol C1 concentration had a slight hyperemia in the small intestine. The remaining abdominal organs were normal. One of the three animals treated with tapentadol C3 concentration had an intestinal congestion, which was not considered relevant by two veterinarians. The remaining abdominal organs were normal. All animals treated with tramadol had normal abdominal organs, with the exception of one that had a slight hyperemia in the small intestine. L-Dopa treated mice all had normal abdominal organs.

The differences found in mice were not considered relevant for histopathology analysis.

Results

Overall, animals had no signs of toxicity and their behavior was normal. Nevertheless, it is noteworthy that animals from one cage presented a strange posture after i.p. administration and behavior testing.

Example 7—Pre-Clinical Efficacy of Tapentadol During ON/OFF Periods of L-Dopa Treatment The unilateral striatal 6-OHDA mice model was used in this study. Specifically, 12 week old CD-1 male mice received an injection of 6-OHDA neurotoxin at the following coordinates: AP +0.9 mm, ML +2.0 mm, DV −3.2 mm, as in the Example outlined above. Animals were injected with 10 μg of 6-OHDA or ascorbic acid (vehicle control) to induce the disease. Disease was induced for 7 days and treatment then was initiated at this time point.

Figure 23:
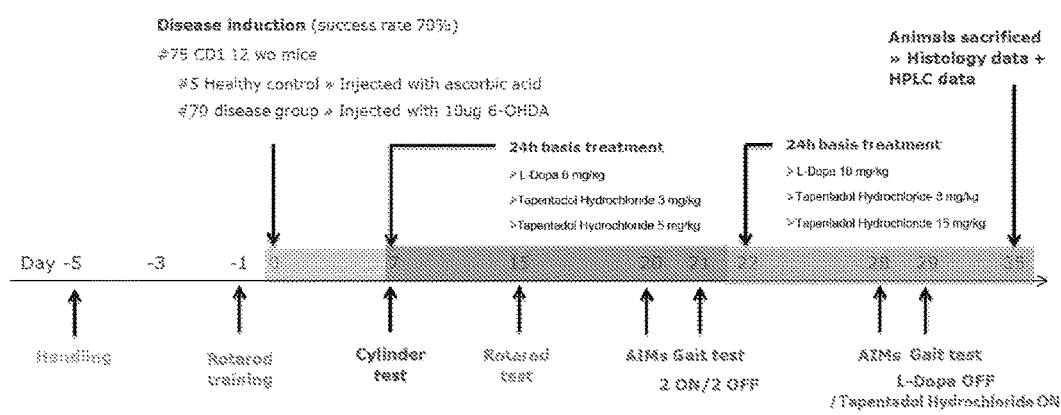
FIG. 23: Experimental design for testing efficacy of tapentadol hydrochloride in 6-OHDA mice during ON and OFF periods of L-Dopa treatment.

Animals were treated on a daily basis through intraperitoneal injection, in accordance with Table 6, below, and FIG. 23, summarizing the experimental design.

TABLE 6

| Administration route | intraperitoneal injection |
| --- | --- |
| Administration frequency | every day, once a day |
| Treatment initiation | 7 days post-injection (dpi) |
| Treatment duration | 28 days |
| Treatment end | 35 dp induction |

Specifically, vehicle and disease control groups received saline injections while the positive control group received 6 mg/kg/day of levodopa (L-DOPA) from day 7 to say 21 post disease induction and 18 mg/kg/day from day 22 to 35 post disease induction. All groups treated with levodopa also received, 30 minutes prior to L-dopa administration, 6 or 12 mg/kg/day benserazide to inhibit peripheral decarboxylation of the levodopa.

The cylinder test was given before therapeutic application to evaluate disease induction. The Rotarod test was given at 15 days post injection (dpi) with tapentadol hydrochloride tested at 2.8 mg/kg/day (concentration 1—C1) and 5 mg/kg/day (concentration 3—C3). The test was given 60 min after therapeutic administration.

The first gait test was given to groups treated with L-Dopa at 6 mg/kg/day, and with both tapentadol hydrochloride C1 and C3 and L-DOPA, and motor effects were evaluated 60 minutes (ON period) after administration. For the second gait test, L-Dopa concentration was increased to 18 mg/kg/day to induce moderate AIMs and tapentadol was increased in the same proportion (3x). That is, tapentadol hydrochloride C1 concentration dosage was increased to 8 mg/kg/day and tapentadol hydrochloride C3 concentration dosage was increased to 15 mg/kg/day. The gait test plan is illustrated in FIGS. 24A-24B.

Motor effects were evaluated at 30 minutes (ON period) and 150 minutes (OFF period) after tapentadol hydrochloride and L-dopa administration, respectively. The assay was designed to measure tapentadol hydrochloride motor effects during its peak action and after L-dopa effects wear off (since 150 minutes is described as the time after L-dopa administration that no longer induces rotational behavior in AIMs test).

On the 35th day after intracranial injection, animals were sacrificed and the animal brains dissected for histology analysis.

Results

Animals' welfare and weight were monitored on a daily basis. There was no significant difference in animal weights between groups with time (data not shown).

To address the efficacy of tapentadol hydrochloride alone or in combination with L-Dopa, several behavioral tests were used, including the cylinder test and the gait test. In each test, different parameters were analyzed but all mainly focused on assessing locomotor behavior recovery. Animals were trained for the gait test before initiation of the assay.

Cylinder Test Results

The Cylinder test mostly is used to evaluate spontaneous and exploratory activity and to determine the extension of the lesion caused by 6-OHDA injection. As noted above, this test consists of placing an animal in a clear cylinder and observing its behavior for 5 minutes. Results are shown in FIGS. 25A-25B. For the Cylinder test in these experiments, the parameters evaluated were: percentage of contralateral paw use (FIG. 25A) and number of right turns (FIG. 25B). The test was given prior to therapeutic initiation (7 days post disease induction).

As seen in FIGS. 26A-26B, 6-OHDA treated mice showed significant motor impairments in the two parameters evaluated at 7 days post lesion, that is, in both the percentage of contralateral paw use (FIG. 26A) and the number of right turns (FIG. 26B), compared to the vehicle treated animals at 7 days post lesion. Values mean ě SEM (n=5-51). A t-student test was performed to compare group means (ns, not significant, *p<0.001, **p<0.0001).

Based on these results, test animals were distributed equally and randomly among therapeutic groups, which was confirmed in that no significant difference in disease induction among the different groups was observed (see, e.g., FIGS. 26A-26B). Animals were treated blindly as well when results were analyzed.

Cylinder test results for different therapeutic groups are shown in FIGS. 26A-26B. As seen, 6-OHDA, L-Dopa, tapentadol hydrochloride C1, tapentadol hydrochloride C1+L-Dopa, tapentadol hydrochloride C3, and tapentadol hydrochloride C3+L-Dopa treated mice showed significant motor impairments in the two parameters evaluated at 7 days post lesion, that is, in percentage of contralateral paw use (FIG. 26A) and number of right turns (FIG. 26B). Values mean ě SEM (n=5-10). A t-student test was performed to compare group means (ns, not significant, p<0.05).

The main conclusion from this test was that disease was well induced and in a similar manner between all treated groups.

Histology Results

To determine the degree of disease induction at the cellular level, dopaminergic neurons positive for Tyrosine hydroxylase (TH) were counted in the substantia nigra pars compacta (SNpc) of sacrificed animals. In the striatum, axons intensity also was measured for TH and Dopamine transporter (DAT) immunoreactivity to evaluate striatum axonal degeneration. Coronal cryosections (20 ǀ m) of mouse brain from each test group were processed for immunostaining and microscope images of TH-stained sections of the substantia nigra pars Compacta were obtained from healthy control mice and disease induced mice. Results are shown in FIGS. 27A-27G (sale bar=20 ǀ m).

Specifically, FIGS. 27A-27G show microscope images of Tyrosine hydroxylase (TH in red) and Dopamine transporter (DAT in green)-stained sections of the striatum from healthy control mice (FIG. 27A), 6-OHDA disease induced mice (FIG. 27B), and disease-induced groups treated with L-Dopa (FIG. 27C), tapentadol hydrochloride at two different concentrations (FIGS. 27D-27E), and a combination of L-Dopa and tapentadol hydrochloride at two different concentrations (FIGS. 27F-27G). Yellow labelling indicates the co-localization of TH and DAT markers. Scale bar=20 ǀ m.

As seen, in the vehicle control (ascorbic acid) group, the number of TH+ cells on both sides was the same (as expected) (FIG. 27A). In the 6-OHDA and therapeutic groups, there was a loss of TH+ cells in the ipsilateral side when compared with the contralateral uninjected side, which indicates that neurodegeneration took place, again as expected (FIGS. 27B-27G). The TH+ cells loss was significant for all groups induced with 6-OHDA when compared with the vehicle group and there was no difference between the disease-induced groups. Animals with more than 80% TH+ cells were excluded (corresponding to less than 20% cell death in SNpc). Typically, cell death was around 40% in SNpc; and axon degeneration was around 50% in Striatum.

FIGS. 28A-28C show a correlation between the TH-positive cell death in the SNpc and the induced axon degeneration in striatum. Specifically, FIGS. 28A-28C show cell loss induced by unilateral intracranial injection of 6-OHDA evaluated by TH-positive cell counts in the ipsilateral (left) and contralateral (right) side of injection (FIG. 328A) and by TH-DAT double positive axons in the striatum (FIG. 28B), as well as a Pearson's correlation between TH-positive cell counts and TH-DAT double positive axons in the striatum (FIG. 28C). Values mean ě SEM (n=5-9). A 1 way ANOVA test was performed to compare group means (ns, not significant, ****p<0.0001).

Overall, these results validated disease induction and ascertained that in all animals, the disease was well induced. This level of partial dopaminergic depletion (60% of dopaminergic reduction) is considered a good model of early and moderate stages of PD.

Results Regarding Abnormal Involuntary Movements—AIMs

As noted above, L-Dopa treatment induces dyskinesia. This condition results in a range of involuntary movements that can be evaluated by the AIMs test. Data shown demonstrate that, as expected, L-Dopa treated groups presented involuntary movements whereas the group treated with tapentadol hydrochloride alone did not. These results may indicate that tapentadol hydrochloride has a different mechanism of action from L-Dopa and a safer profile.

Abnormal involuntary movements were evaluated during the cylinder test, 20 days post injection, at 4 different time points after L-dopa administration (30, 60, 90, and 120 minutes), and results are shown in FIGS. 29A-29F. The following parameters were evaluated: hyperkinetic and/or dystonic movements of the contralateral forelimb on the sagittal or frontal plane (forelimb involuntary movements; FIG. 29A), twisted posture of the neck and upper body towards the side contralateral to the lesion (upper body involuntary movements; FIG. 29B), twitching of orofacial muscles, empty jaw movements and contralateral tongue protrusion (orofacial involuntary movements; FIG. 29C), circular locomotion with contralateral side bias (circular involuntary movements; FIG. 29D), total involuntary movements (FIG. 29E), and total involuntary movement along the different timepoints (FIG. 29F). Scores ranged from 0 to 4, depending on the severity of the involuntary movements, and scores from all time points were summed. Total abnormal involuntary movements (FIGS. 29E-329F) were the sum of all 4 different involuntary movements evaluated. Values mean ě SEM (n=5-9). A one-way A NOVA test with Bonferroni post-test was performed to compare group means at each timepoint. *p<0.05, ****p<0.0001.

Regarding FIGS. 29A and 29C, forelimb and orofacial involuntary movements were difficult to detect in mice, considering the animal˘s size, leading to possible errors. Accordingly, these measurements were not statistically significant. Nonetheless, these two abnormal involuntary movements were more evident in higher L-dopa doses. Moreover, analyses of total AIMS at 20 days post injection (dpi) indicated that L-Dopa at 6 mg/Kg/day produces peak action at 30 min after administration, which then quickly decreased to have no effect 60 minutes after administration. This response was maintained in the presence of tapentadol hydrochloride C1 and C3.

These tests were repeated using higher concentrations of L-dopa and results are shown in FIGS. 30A-30F. Specifically, at 28 days post injection (dpi), L-Dopa concentration was increased to 18 mg/Kg/day and the AIMS tests repeated. Results revealed a longer L-Dopa effect, with AIMs present until 90 min after administration. These effects were not reverted by the concomitant administration of tapentadol hydrochloride. The same parameters were analyzed as for 20 days post injection (dpi). Values mean ě SEM (n=5-9). A one-way ANOVA test with Bonferroni post-test was performed to compare group means at each timepoint. *p<0.05, ****p<0.0001.

As FIG. 30A shows, forelimb involuntary movements became evident. Further, as FIG. 30E shows, severity of total AIMs increased and severity was prolonged after administration.

A correlation between total abnormal involuntary movements and cell loss or axonal degeneration was established for L-dopa treated groups and results are shown in FIGS. 31A-31B. Specifically, FIGS. 31A-31B show a Pearson˘s correlation between the number of TH-positive cells (FIG. 31A) or the TH-DAT axons (FIG. 31B) with total AIMs in the L-dopa treated groups. For both groups, there was a significant correlation between cell death or axonal degeneration and total abnormal involuntary movements. Overall, these results indicated that tapentadol hydrochloride alone does not induce AIMs, therefore providing a safer profile than L-dopa; nonetheless, tapentadol hydrochloride did not revert L-Dopa induced AIMs in this model.

Cell Loss and Gait Test Results Evidence OFF Period Model

During administration of levodopa in patients, motor fluctuations oscillate between OFF times, a state of decreased mobility, and ON times, periods when the medication is working and symptoms are controlled. The goals of therapy are obvious: to reduce OFF time; to make OFF times more predictable; and to be able to treat such periods with lower amounts of medication (so as to avoid side effects such as dyskinesia).

It has been postulated that chronic L-Dopa treatment in humans may be detrimental, inducing motor complications (postural abnormalities, freezing episodes, and speech impairment), as well as 'dopa-resistant_ non-motor signs (autonomic dysfunction, mood, and cognitive impairment) and/or drug-related side effects (especially psychosis, motor fluctuations, and dyskinesias). Such occurrences, along with cell culture data indicating that L-Dopa has a neurotoxic effect, have led to the strategy of delaying levodopa treatment for as long as possible to avoid eventual side effects and, when treatment is initiated, attempting to deliver L-Dopa to the brain continuously, rather than in a pulsatile fashion (e.g., using controlled release formulations and/or adjunctive therapies). However, there is little firm evidence to suggest that L-dopa is toxic in vivo.

The present studies show no evidence of L-dopa neurotoxicity in vivo¯the number of TH+ cells in the L-dopa treated group was similar to the 6-OHDA treated group. Results are shown in FIGS. 32A-32B.

As FIGS. 32A-32B show, cell loss induced by unilateral intracranial injection of 6-OHDA was evaluated by TH-positive cell counts in the ipsilateral (left) and contralateral (right) side of injection (FIG. 32A) and by TH-DAT double positive axons in the striatum (FIG. 32B). Values mean ě SEM (n=5-9). A 1 way ANOVA test was performed to compare group means (ns, not significant, ****p<0.0001).

Gait Test Results

To better observe the movement pattern of mice˘s limbs, a new device was engineered similar to that used in a beam test, but with a closed corridor and a door. The apparatus was transparent with two home-cages at the extremities, one at the entrance that is transparent and another on the opposite end that is black. Each test was repeated 5 times and the 3 more consistent trials were selected for paw placement analysis. Data was recorded by 3 different cameras: on the bottom, top, and side of the corridor. Each camera allowed measurement of a different gait parameter. Specifically, the bottom camera allowed measurement, through the base of the support, of the hind paw distance and hind paw angle. The top camera allowed measurement of different parameters at distinct zones¯in the green area (most of the length of the apparatus), maximum and mean velocity, percentage of time resting/moving slow/moving fast, and time to the door were measured; the dark blue area provided a lag zone; and in the yellow area (area in front of the door), the permanence time before the door, mean velocity before the door, and latency to cross the door were measured. The side camera was used to analyze mice posture.

To mimic ON and OFF L-dopa periods, the gait test was conducted at 20 days post injection (dpi), 60 min after L-Dopa administration, mimicking ON; and at 28 days post injection, 150 min after L-Dopa administration, mimicking OFF. Tapentadol hydrochloride, as always ON, was administered at the same time as L-DOPA and measured after 60 min, at 20 days post injection; at 28 days post injection, it was measured after 30 min post administration, when L-Dopa is already OFF (see Gait test plan, FIGS. 24A-24B).

At 21 days post injection (dpi), all the parameters measured showed no significant improvement after tapentadol hydrochloride treatment (data not shown).

Nonetheless, improvements were observed during the mimicked L-Dopa OFF periods. Animals chronically treated with L-Dopa, at 29 days post injection (dpi) after 150 min, showed locomotor deficits regarding the parameters mean velocity, percentage of time resting, and percentage of time moving fast. Critically, however, this phenotype was ameliorated for animals also treated with tapentadol hydrochloride. Results are shown in FIGS. 33A-33E.

FIGS. 33A-33E show gait test results at 29 days post injection (dpi). Tapentadol hydrochloride treated animals exhibited behavioral recovery in maximum velocity (FIG. 33A), mean velocity (FIG. 33B), and percentage of time resting or moving fast (FIG. 33C), whereas moving slow was similar in all the groups (FIG. 33D, showing decomposition of the plot in FIG. 33C), as was the time that the animal took to reach the door (FIG. 33E). Values mean ě SEM (n=5-9). A t-student test was performed to compare group means at each timepoint (ns, not significant, *p<0.05, p<0.01, *p<0.001).

Accordingly, in the animal model used in this study, motor impairments were evident in L-dopa treated animals after L-dopa withdrawal, when compared to a disease group (see again FIGS. 33A-33E). This state of hypomobility resembles the OFF motor state of parkinsonian patients, when L-Dopa wears off and its therapeutic effects stop, in the sense that L-Dopa treated mice show worse locomotor behavior than 6-OHDA treated mice at 29 days post injection (dpi).

Gait test results at 29 days post injection (dpi) for parameters evaluating behavior 'close to the door_ are shown in FIGS. 34A-34C, and evidence the same trends. Specifically, parameters analyzing the behavior close to the door, that is, permanence time before the door, latency to cross the door, and mean velocity before the door, all further evidence the trends of L-Dopa chronic administration leading to worse behavior (during OFF periods) than 6-OHDA treated animals without L-Dopa treatment, as well as showing recovery with the administration of tapentadol hydrochloride along with L-Dopa.

As FIGS. 34A-34C show, amongst different treatment groups, tapentadol hydrochloride-treated animals exhibited behavioral recovery in terms of permanence time before the door (FIG. 34A), latency to cross the door (FIG. 34B), and mean velocity before the door (FIG. 34C). Values mean ě SEM (n=5-9). A t-student test was performed to compare group means at each timepoint (ns, not significant, *p<0.05, p<0.01, *p<0.001).

Linear regressions were calculated for behavioral test results and the nigral TH+ cell loss or striatal axonal denervation. Results are shown in FIGS. 35A-35L.

As FIGS. 35A-35L show, correlations between the number of SNpc TH-positive cells and behavioral impairment was verified for mean velocity (FIG. 35A), percentage of time moving fast (FIG. 35C), percentage of time moving slow (FIG. 35E), and time to the door (FIG. 35G). Correlations between striatum axon projections and behavioral impairments was observed only for percentage of time moving slow (FIG. 35F).

These correlations indicate that mean velocity, percentage of time moving fast, percent of time moving slow, and time to the door are motor-affected behaviors dependent of dopaminergic brain regions and, further, it is possible that parameters related with the door, such as mean velocity before the door and permanence time before the door, might be related to non-motor effects and/or activation of other brain regions, besides the dopaminergic region. Most likely, the decreased motor performance in the OFF phase, only seen in animals receiving L-Dopa alone, might be due to a combined motor and non-motor effect of L-Dopa withdrawal. In agreement with this theory, studies of non-motor manifestations in PD patients have shown that chronic L-Dopa treatment may promote mood fluctuations, as well as motor fluctuations. For example, significant mood changes have been associated with ON/OFF phenomena in patients with PD.

CONCLUSION

The aim of this assay was to test the efficacy of tapentadol hydrochloride on a unilateral mice model of PD and to search for interactions between tapentadol hydrochloride and L-DOPA. Two different tapentadol hydrochloride concentrations were used in a concentration incremental model, by the same proportion as L-DOPA was increased (dose escalation). Motor improvement was evaluated with several behavioral tests. Results support a pro-motor symptomatic effect for treating effects of long-term use of L-dopa, including during OFF periods. Thus, tapentadol hydrochloride can provide patients already taking high doses of L-dopa with a protective effect from L-DOPA motor impairment. Noteworthy, tapentadol hydrochloride did not increase dyskinesia in co-treatment with L-DOPA.

We claim:

1. A method of treating a side effect of levodopa or a derivative thereof administered to a subject suffering from Parkinson's disease, comprising
    administering an effective amount of a pharmaceutical composition to said subject, said pharmaceutical composition comprising tapentadol or a derivative thereof and a pharmaceutically acceptable carrier, but not comprising an opioid antagonist;
    wherein treatment comprises a reduction in duration and/or frequency of an OFF period of said disease; and delaying or reducing during said OFF periods at least one of dyskinesia, dystonia, chorea, athetosis, motor fluctuation, postural abnormality, bradykinesia, freezing of gait, shaking, rigidity, slowness of movement, difficulty with walking and gait, autonomic dysfunction, or cognitive impairment.

2. The method of claim 1, wherein the pharmaceutical composition comprises tapentadol hydrochloride in an amount providing an effective dose of about 100-250 mg/day.

3. The method of claim 1, wherein said subject has an advanced stage of Parkinson's disease or a stage of Parkinson's disease that is less responsive to said levodopa or derivative thereof than an earlier stage.

4. The method of claim 2, wherein the pharmaceutical composition comprises tapentadol hydrochloride in an amount providing an effective dose of about 126 mg/day.

5. The method of claim 1, wherein tramadol is not used.

6. The method of claim 1, wherein the composition is administered orally.

7. The method of claim 1, wherein the pharmaceutical composition is administered in combination with levodopa or a derivative thereof.

8. The method of claim 7, wherein the pharmaceutical composition further is administered in combination with carbidopa.

9. The method of claim 7, wherein said levodopa is in an amount suitable for administration to said subject having an advanced stage of Parkinson's disease or a stage of Parkinson's disease that is less responsive to levodopa than an earlier stage.

10. The method of claim 9, wherein said less responsive stage is an OFF period in levodopa treatment and wherein administration of said pharmaceutical composition is effective to reduce the duration, or frequency, or both, of the OFF periods.

11. The method of claim 1, wherein the side effect is a levodopa side effect.

12. The method of claim 11, wherein the levodopa is administered two or more times a day to provide a daily dose of about 300-600 mg/day.

13. The method of claim 11, wherein the levodopa is administered two or more times a day to provide a daily dose of about 700-1,000 mg/day.

14. A method of treating a subject suffering from Parkinson's disease and having a side effect of OFF periods to levodopa therapy, comprising
- administering a pharmaceutical composition to said subject, said pharmaceutical composition comprising a pharmaceutically acceptable carrier and tapentadol hydrochloride in an amount to provide an effective dose of about 100-250 mg/day;
- wherein treatment comprises reducing duration and/or frequency of said OFF periods; and delaying or reducing during said OFF periods at least one of dyskinesia, dystonia, chorea, athetosis, motor fluctuation, postural abnormality, bradykinesia, freezing of gait, shaking, rigidity, slowness of movement, difficulty with walking and gait, autonomic dysfunction, or cognitive impairment.

15. The method of claim 14, wherein the pharmaceutical composition is administered in combination with carbidopa.

16. The method of claim 14, wherein said pharmaceutical composition does not comprise an opioid antagonist.

17. The method of claim 14, wherein said subject has an advanced stage of Parkinson's disease or a stage of Parkinson's disease that is less responsive to levodopa or a derivative thereof than an earlier stage.

18. The method of claim 17, wherein said less responsive stage is an OFF period in levodopa treatment.

19. The method of claim 14, wherein the pharmaceutical composition comprises tapentadol hydrochloride in an amount providing an effective dose of about 126 mg/day.

20. The method of claim 14, wherein tramadol is not used.

21. The method of claim 14, wherein the composition is administered orally.

22. The method of claim 14, wherein levodopa is administered two or more times a day to provide a daily dose of about 300-600 mg/day.

23. The method of claim 14, wherein levodopa is administered two or more times a day to provide a daily dose of about 700-1,000 mg/day.

* * * * *